(12) United States Patent
Seyedi

(10) Patent No.: US 11,873,296 B2
(45) Date of Patent: Jan. 16, 2024

(54) SOLID FORMS OF A DUAL RAF/MEK INHIBITOR

(71) Applicant: Verastem, Inc., Needham, MA (US)

(72) Inventor: Farzaneh Seyedi, Mansfield, MA (US)

(73) Assignee: VERASTEM, INC., Needham, MA (US)

( * ) Notice: Subject to any disclaimer, the term of this patent is extended or adjusted under 35 U.S.C. 154(b) by 0 days.

(21) Appl. No.: 18/147,921

(22) Filed: Dec. 29, 2022

(65) Prior Publication Data

US 2023/0391759 A1    Dec. 7, 2023

Related U.S. Application Data

(60) Provisional application No. 63/349,815, filed on Jun. 7, 2022.

(51) Int. Cl.
*C07D 405/12* (2006.01)
*A61K 9/00* (2006.01)

(52) U.S. Cl.
CPC .......... *C07D 405/12* (2013.01); *A61K 9/0053* (2013.01); *C07B 2200/13* (2013.01)

(58) Field of Classification Search
CPC ............................ C07D 405/14; C07D 405/12
See application file for complete search history.

(56) References Cited

U.S. PATENT DOCUMENTS

| | | | |
|---|---|---|---|
| 7,897,792 B2 | 3/2011 | Iikura et al. | |
| 7,928,109 B2 | 4/2011 | Luzzio et al. | |
| 8,247,411 B2 | 8/2012 | Luzzio et al. | |
| 8,278,465 B2 | 10/2012 | Iikura et al. | |
| 8,440,822 B2 | 5/2013 | Luzzio et al. | |
| 8,569,378 B2 | 10/2013 | Sakai et al. | |
| 9,133,174 B2 | 9/2015 | Murakata et al. | |
| 9,962,385 B2 | 5/2018 | Pachter et al. | |
| 10,406,158 B2 | 9/2019 | Pachter et al. | |
| 10,450,297 B2 | 10/2019 | Luzzio et al. | |
| 10,532,056 B2 | 1/2020 | Pachter et al. | |
| 11,400,090 B2 | 8/2022 | Banerji | |
| 11,517,573 B2 | 12/2022 | Banerji | |
| 2010/0004233 A1 | 1/2010 | Iikura et al. | |
| 2011/0086837 A1 | 4/2011 | Belvin et al. | |
| 2011/0092700 A1 | 4/2011 | Iikura et al. | |
| 2012/0214828 A1 | 8/2012 | Hatzivassiliou et al. | |
| 2013/0005964 A1 | 1/2013 | Luzzio et al. | |
| 2013/0217710 A1 | 8/2013 | Alves-Aivado et al. | |
| 2014/0024653 A1 | 1/2014 | Debussche et al. | |
| 2014/0113930 A1 | 4/2014 | Gately | |
| 2014/0194442 A1 | 7/2014 | Solca et al. | |
| 2014/0213786 A1* | 7/2014 | Murakata ............ | C07D 405/14 544/316 |
| 2015/0111904 A1 | 4/2015 | Dumble et al. | |
| 2015/0190346 A1 | 7/2015 | Padval et al. | |
| 2016/0310476 A1 | 10/2016 | Saha et al. | |
| 2016/0346282 A1 | 12/2016 | Pachter et al. | |
| 2017/0020884 A1 | 1/2017 | Lichenstein et al. | |
| 2017/0112865 A1 | 4/2017 | Morrison et al. | |
| 2017/0281624 A1 | 10/2017 | Peters et al. | |
| 2018/0135058 A1 | 5/2018 | Niitsu et al. | |
| 2018/0289683 A1 | 10/2018 | McCormick et al. | |
| 2019/0136212 A1 | 5/2019 | Raines et al. | |
| 2019/0367964 A1 | 12/2019 | Izar et al. | |
| 2020/0038331 A1 | 2/2020 | Padval et al. | |
| 2020/0046749 A9 | 2/2020 | Bhattacharjee | |
| 2020/0147080 A1 | 5/2020 | Pachter et al. | |
| 2020/0222407 A1 | 7/2020 | Lipford et al. | |
| 2020/0330471 A1 | 10/2020 | Pachter et al. | |
| 2020/0368238 A1 | 11/2020 | Nichols et al. | |
| 2021/0154198 A1 | 5/2021 | Deng et al. | |
| 2021/0330670 A1 | 10/2021 | Banerji | |

FOREIGN PATENT DOCUMENTS

| | | | |
|---|---|---|---|
| EP | 1982982 A1 | 10/2008 | |
| EP | 2172198 A1 | 4/2010 | |
| WO | WO-2001017984 A1 | 3/2001 | |
| WO | WO-2007/091736 A1 | 8/2007 | |
| WO | WO-2009/014100 A1 | 1/2009 | |
| WO | WO-2009100159 A2 | 8/2009 | |
| WO | WO-2012/045194 A1 | 4/2012 | |
| WO | WO-2012/095505 A1 | 7/2012 | |
| WO | WO-2013/170066 A1 | 11/2013 | |
| WO | WO-2013/182668 A1 | 12/2013 | |
| WO | WO-2014/059095 A1 | 4/2014 | |
| WO | WO-2016115376 A1 | 7/2016 | |
| WO | WO-2017/004192 A1 | 1/2017 | |
| WO | WO-2019051084 A1 | 3/2019 | |
| WO | WO-2019051296 A1 | 3/2019 | |

(Continued)

OTHER PUBLICATIONS

Wada et al., "The dual RAF/MEK inhibitor CH5126766/R05126766 may be a potential therapy for RAS-mutated tumor cells." PLOS ONE, 2014, 9(11): e113217.

Martinez-Garcia et al., "First-in-human, phase I dose-escalation study of the safety, pharmacokinetics, and pharmacodynamics of R05126766, a first-in-class dual MEK/RAF inhibitor in patients with solid tumors," Clinical Cancer Research, 2012, 18(17):4806-4819.

Ishii et al., "Enhanced inhibiion of ERK signaling by a novel allosteric MEK inhibitor, CH5126766, that suppresses feedback reactivation of RAF activity," Cancer Res. 2013, 73(13): 4050-4060.

Honda et al., "Phase I and pharmacokinetic/pharmacodynamic study of R05126766, a first-in-class dual Raf/MEK inhibitor, in Japanese patients with advanced solid tumors," Cancer Chemotherapy Pharmacology, 2013, 72: 577-584.

Harris et al., "Updated efficacy and safety results from the phase I study of intermittent dosing of the dual MEK/RAF inhibitor, R05126766 in patients (pts) with RAS/RAF mutated advanced solid tumours," Journal of Clinical Oncology, 2016, 34(15_suppl): 2582.

(Continued)

*Primary Examiner* — Rei Tsang Shiao
(74) *Attorney, Agent, or Firm* — Goodwin Procter LLP

(57) ABSTRACT

Solid forms of a dual RAF/MEK inhibitor, pharmaceutical compositions thereof, oral dosage forms thereof, and methods of treating cancer are described herein. Also provided herein are processes for preparing solid forms of a dual RAF/MEK inhibitor and pharmaceutical compositions and oral dosage forms thereof.

27 Claims, 33 Drawing Sheets

(56) References Cited

FOREIGN PATENT DOCUMENTS

| WO | WO-2019/096397 A1 | 5/2019 |
| --- | --- | --- |
| WO | WO 2019/096449 * | 5/2019 |
| WO | WO-2020023851 A1 | 1/2020 |
| WO | WO-2021047783 A1 | 3/2021 |
| WO | WO-2021047798 A1 | 3/2021 |
| WO | WO-2021142144 A1 | 7/2021 |
| WO | WO-2021/154929 A1 | 8/2021 |
| WO | WO-2021/222278 A1 | 11/2021 |
| WO | WO-2022/015736 A1 | 1/2022 |
| WO | WO-2022/170060 A1 | 8/2022 |
| WO | WO-2023009572 A1 | 2/2023 |
| WO | WO-2023076991 A1 | 5/2023 |
| WO | WO-2023081676 A1 | 5/2023 |
| WO | WO-2023108110 A2 | 6/2023 |
| WO | WO-2023147297 A2 | 8/2023 |

OTHER PUBLICATIONS

Chenard-Poirier et al., "Results from the biomarker-driven basket trial of RO5126766 (CH5126766), a potent RAF/MEK inhibitor, in RAS- or RAF-mutated malignancies, including multiple myeloma" (2017) ASCO annual meeting, presentation slides, 9 pages.
Chenard-Poirier et al., "Meeting library results from the biomarker-driven basket trial of R05126766 (CH5127566), a potent RAF/MEK inhibitor, in RAS- or RAF-mutated malignancies including multiple myeloma," 2017, https://meetinglibrary.asco.org/record/144582/absract.
ClinicalTrials.gov NCT05608252 Study, "VS-6766+Abema+Fulv in Met HR+/HER-BC", first posted Nov. 8, 2022.
ClinicalTrials.gov NCT05375994 Study, "Study of Avutometinib (VS-6766) + Adagrasib in KRAS G12C NSCLC Patients (RAMP204)", first posted May 17, 2022, last updated Dec. 23, 2022.
ClinicalTrials.gov NCT05512208 Study, "A Phase 2 Study of VS-6766 Plus Defactinib", first posted Aug. 23, 2022.
ClinicalTrials.gov NCT05200442 Study, "A Study of VS-6766 and Cetuximab in Patients With Advanced Colorectal Cancer", first posted Jan. 20, 2022, last updated Oct. 4, 2022.
ClinicalTrials.gov NCT05187169 Study, "Food Effect of VS-6766 in Healthy Adult Subjects", first posted Jan. 11, 2022, last updated May 10, 2022.
ClinicalTrials.gove NCT04625270 Study, "A Study of Avutometinib(VS-6766) v. Avutometinib(VS-6766) + Defactinib in Recurrent Low-Grade Serous Ovarian Cancer With and Without a KRAS Mutation (RAMP-201)", first posted Nov. 12, 2020, last updated Dec. 30, 2022.
ClinicalTrials.gov NCT04720417 Study, "Defactinib and VS-6766 for the Treatment of Patients With Metastatic Uveal Melanoma", first posted Jan. 22, 2021, last updated Jan. 31, 2022.
ClinicalTrials.gov NCT05074810 Study, "Phase 1/2 Study of Avutometinib (VS-6766) + Sotorasib in G12C NSCLC Patients (RAMP203)", first posted Oct. 12, 2021, last updated Dec. 29, 2022.
ClinicalTrials.gov NCT02407509 Study, "Phase I Trial of VS-6766 Alone and in Combination With Everolimus (RAF/MEK)", first posted Apr. 3, 2015, last updated May 2, 2022.
ClinicalTrials.gov NCT04620330 Study, "A Study of Avutometinib (VS-6766) + Defactinib in Recurrent KRAS G12V, Other KRAS and BRAF Non-Small Cell Lung Cancer (RAMP202)", first posted Nov. 6, 2020, last updated Dec. 27, 2022.
ClinicalTrials.gov NCT03875820 Study, "Phase I Trial of Defatcinib and VS-6766. (FRAME)", first posted Mar. 15, 2019, last updated Mar. 31, 2022.
ClinicalTrials.gov NCT03681483 Study, "RO5126766 for Patients With Advanced KRAS-Mutant Lung Cancer", first posted Sep. 24, 2018, last updated Dec. 2, 2022.
International Search Report and Written Opinion for International Patent Application No. PCT/US2021/015401 dated Apr. 7, 2021, 10 pages.

Canon et al., "The Clinical KRAS(G12C) Inhibitor AMG 510 Drives Anti-Tumour Immunity", 34 Nature, vol. 575, Oct. 30, 2019 (Oct. 30, 2019), 6 pages.
Murray et al., "Repotrectinib Increases KRASG12C Inhibitor Effectiveness Via Simultaneous Inhibition of SRC, FAK, and JAK2," Turning Point Therapeutics. Abstract #147, Oct. 24, 2020 (Oct. 24, 2020), entire document.
Akinleye et al., "MEK and the inhibitors: from bench to bedside," Journal of Hematology & Oncology, 2013, 6(27): 1-11.
Aoki et al., "Optimizing the physicochemical properties of Raf/MEK inhibitors by nitrogen scanning," American Chemical Society Medicinal Chemistry Letters, May 2014: 309-314.
Barkan D. et al. "Beta1-Integrin: A potential therapeutic target in the battle against cancer recurrence." Clinical Cancer Research, 2011, vol. 17, No. 23, pp. 7219-7223.
Bhatt et al., "In silico docking studies of lupeol with MAPK pathway proteins-raf-1, MEK & ERK," Journal of Experimental Therapeutics and Oncology, Dec. 2017: 137-140.
Cole Jr. et al. "Suppression of Pro-metastasis phenotypes expression in malignant pleural mesothelioma by the PI3K inhibitor LY294002 or the MEK inhibitor UO126." Anticancer Research, 2006, vol. 26, No. 2A, pp. 809-821.
El Touny, L. H. et al. "Combined SFK/MEK inhibition prevents metastatic outgrowth of dormant tumor cells" Journal of Clinical Investigation, Jan. 2014, vol. 124, No. 1, pp. 156-168.
El-Khoueiry A. "Abstract B75: A first in-human phase I study to evaluate the MEK1/2 inhibitor GDC-0623 in patients with advanced solid tumors." Molecular Cancer Therapeutics, Nov. 2013, vol. 12, No. 11 Suppl., Abstract No. B75, doi:10.1158/1535-7163.TARG-13-B75.
English translation of the Official Action dated Nov. 5, 2018 for Japanese patent application No. 2016-550218.
European Search Report for EP15746033 dated Aug. 18, 2017.
Gerber et al., "Phase II study of defactinib in patients with KRAS mt NSCLC—phase II study of defactinib, VS-6063, a focal adhesion kinase (FAK) inhibitor, in patients with KRAS mutant non-small lung cancer (NSCLC)," 2015, 16th World Conference on Lung Cancer, International Association for the Study of Lung Cancer.
Heist R. S. "Combination of a MEK inhibitor, pimasertib (MSC1936369B), and a PI3K/mTOR inhibitor, SAR 245409, in patients with advanced solid tumors: Results of a phase lb dose-escalation trial." Journal of Clinical Oncology, 2013, vol. 31, No. 15, Suppl., Abstract No. 2530.
History of Changes for Study NCT00773526, "An open label dose-escalation study to evaluate safety, pharmacokinetics and anti-tumor activity of RO5126766, a dual raf and MEK inhibitor, administered orally as monotherapy in patients with advanced tumors," dated Nov. 2, 2016.
History of Changes for Study NCT02407509, "A phase I trial of RO5126766 (a dual RAF/MEK inhibitor) exploring intermittent, oral dosing regimens in patients with solid tumours or multiple myeloma, with an expansion to explore intermittent dosing in combination with everolimus," dated Nov. 1, 2018.
History of Changes for Study NCT03875820, "FRAME: A phase I trial of the combination of VS-6063 (FAK inhibitor) and RO5126766 (CH5126776) (a dual RAF/MEK inhibitor) in patients with advanced solid tumours," dated Apr. 9, 2020.
History of Changes for Study NCT03875820, "FRAME: A phase I trial of the combination of VS-6063 (FAK inhibitor) and RO5126766 (CH5126776) (a dual RAF/MEK inhibitor) in patients with advanced solid tumours," dated Feb. 28, 2020.
History of Changes for Study NCT03875820, "FRAME: A phase I trial of the combination of VS-6063 (FAK inhibitor) and RO5126766 (CH5126776) (a dual RAF/MEK inhibitor) in patients with advanced solid tumours," dated Jun. 25, 2020.
History of Changes for Study NCT03875820, "FRAME: A phase I trial of the combination of VS-6063 (FAK inhibitor) and RO5126766 (CH5126776) (a dual RAF/MEK inhibitor) in patients with advanced solid tumours," dated Mar. 15, 2019.
History of Changes for Study NCT03875820, "FRAME: A phase I trial of the combination of VS-6063 (FAK inhibitor) and RO5126766

(56) References Cited

OTHER PUBLICATIONS (CH5126776) (a dual RAF/MEK inhibitor) in patients with advanced solid tumours," dated Nov. 21, 2019.
History of Changes for Study NCT03875820, "FRAME: A phase I trial of the combination of VS-6063 (FAK inhibitor) and RO5126766 (CH5126776) (a dual RAF/MEK inhibitor) in patients with advanced solid tumours," dated Sep. 11, 2020.
International Search Report and Written Opinion for International Application No. PCT/EP2017/079506, dated Aug. 13, 2018.
International Search Report and Written Opinion for International Application No. PCT/EP2018/062805, dated Aug. 16, 2018.
International Search Report and Written Opinion for International Application No. PCT/EP2019/074565, dated Jun. 2, 2020.
International Search Report and Written Opinion for International Application No. PCT/EP2020/056642, dated Jun. 24, 2020.
International Search Report and Written Opinion for International Application No. PCT/EP2020/075455, dated Nov. 24, 2020.
International Search Report for PCT/US2015/14843 dated Apr. 21, 2015.
Jones et al., "A phase I study of VS-6063, a second-generation focal adhesion kinase inhibitor, in patients with advanced solid tumors," Investigational New Drugs, 2015, 33(5): 1100-1107.
Kolev, V. N. "Abstract A39: FAK inhibitors VS-6063 and VS-4718 preferentially target ovarian cancer stem cells." Clinical Cancer Research, Oct. 2013, vol. 19, No. 19 Suppl., Abstract No. A39.
Kraeber-Bodéré et al., "Differences in the biologic activity of 2 novel MEK inhibitors revealed by F-FDG PET: Analysis of imaging data from 2 phase I trials," The Journal of Nuclear Medicine, 2012, 53(12): 1836-1846.
Lito et al., "Disruption of CRAF-mediated MEK activation is required for effective MEK inhibition in KRAS mutant tumors," Cancer Cell. 2014, 25(5): 697-710.
Matsumoto, S. "Combination efficacy of mTOR and MEK inhibitor in malignant pleural mesothelioma (MPM)." Journal of Clinical Oncology, 2013, vol. 31, No. 15 Suppl., Abstract No. e18557, doi:10.1200/jco.2013.31.15_suppl.e18557.
Milella et al. "Beyond single pathway inhibition: MEK inhibitors as a platform for the development of pharmacological combinations with synergistic anti-leukemic effects," Current Pharmaceutical Design, Nov. 2005, 2779-2795.
Miller et al., "MEK1/2 inhibitors in the treatment of gynecologic malignancies," Gynecologic Oncology, 2014, 133: 128-137.
Miyoshi et al. "Antitumor activity of MEK and PI3K inhibitors against malignant pleural mesothelioma cells in vitro and in vivo." International Journal of Oncology, 2012, vol. 41, No. 2, pp. 449-456.
Pachter, J. A. "Sensitivity of malignant mesothelioma lacking merlin to the FAK inhibitor VS-6063: Evaluation of merlin/NF2 status in clinical samples." Journal of Clinical Oncology, Nov. 2013, vol. 31, No. 15 Suppl., Abstract No. e18541, doi:10.1200/jco.2013.31.15_suppl.e18541.
Patel, M. R. "Abstract A69: Phase 1/1b study of the FAK inhibitor defactinib (VS-6063) in combination with weekly paclitaxel for advanced ovarian cancer." Molecular Cancer Therapeutics, Nov. 2013, vol. 12, No. 11 Suppl., Abstract No. A69, doi:10.1158/1535-7163.TARG-13-A69.
Ring, J. E. "Abstract B283: Defactinib (VS-6063) targets cancer stem cells directly and through inhibition of tumor-associated macrophages and cytokine production." Molecular Cancer Therapeutics, Nov. 2013, vol. 12, No. 11 Suppl., Abstract No. B283, doi:10.1158/1535-7163.TARG-13-B283.
Shapiro, I. M. "Abstract C262: Malignant mesothelioma lacking merlin shows enhanced sensitivity to the FAK inhibitor defactinib (VS-6063): Elucidation of the merlin-FAK relationship." Molecular Cancer Therapeutics, Nov. 2013, vol. 12, No. 11 Suppl., Abstract No. C262, doi:10.1158/1535-7163.TARG-13-C262.
Shimzu et al., "A first-in-Asian phase 1 study to evaluate safety, pharmacokinetics and clinical activity of VS-6063, a focal adhesion kinase (FAK) inhibitor in Japanese patients with advanced solid tumors," Cancer Chemotherapy and Pharmacology, 2016, 77(5): 997-1003.
Sulzmaier et al., "FAK in cancer: mechanistic findings and clinical applications," Nature reviews, Cancer, 2014, 14(9): 598-610.
Tanaka et al., "MEK inhibitors as a novel therapy for neuroblastoma: Their in vitro effects and predicting their efficacy," Journal of Pediatric Surgery, 2016, 51: 2074-2079.
Tegnebratt et al., "[18F]FDG-PET imaging is an early non-invasive pharmacodynamic biomarker for a first-in-class dual MEK/Raf inhibitor, RO5126766 (CH5126766), in preclinical xenograft models," EJNMMI Research, 2013, 3(67): 1-11.
Ueyama et al., "Inhibition of MEK1 signaling pathway in the liver ameliorates insulin resistance," Journal of Diabetes Research, Jan. 13, 2016.
Van Dort et al., "Dual inhibition of allosteric mitogen-activated protein kinase (MEK) and phosphatidylinositol 3-kinase (PI3K) oncogenic targets with a bifunctional inhibitor," Bioorg Med Chem., 2015, 23(7): 1386-1394.
Vidal, Abstract C271: FAK inhibitor defactinib (VS-6063) enhances the efficacy of paclitaxel and preferentially targets ovarian cancer stem cells. Molecular Cancer Therapeutics, Nov. 2013, vol. 12, No. 11 Suppl., Abstract No. C271, doi:10.1158/1535-7163.TARG-13-C271.
Vu et al. "Green tea epigallocatechin gallate exhibits anticancer effect in human pancreatic carcinoma cells via the inhibition of both focal adhesion kinase and insulin-like growth factor—I receptor." Journal of Biomedicine and Biotechnology, Jan. 8, 2010.
Weaver, D. T. "Abstract A31: Merlin loss as a biomarker for defactinib (VS-6063) sensitivity: High frequency in malignant mesothelioma tumors." Molecular Cancer Therapeutics, Nov. 2013, vol. 12, No. 11 Suppl., Abstract No. A31, doi:10.1158/1535-7163.TARG-13-A31.
Xu, "Focal adhesion kinase (FAK) inhibitors VS-6063 and VS-4718 target cancer stem cells." Journal of Clinical Oncology, May 2013, vol. 31, No. 15 Suppl., Abstract No. e13523. doi:10.1200/jco.2013.31.15_suppl.e13523.
"History of Changes for Study NCT02407509, Phase I trial of RO5126766 (DDU RAF/MEK)," dated Apr. 3, 2015.
"History of Changes for Study NCT03681483, RO5126766 for patients with advanced KRAS-mutant lung cancer," dated Nov. 2, 2018.
"History of Changes for Study NCT04625270, A study of VS-6766 v. VS-6766 + defactinib in recurrent low-grade serous ovarian cancer with and without a KRAS mutation," dated Nov. 12, 2020.
"History of Changes for Study NCT04620330, A study of VS-6766 v. VS-6766 + defactinib in recurrent G12V or other KRAS-mutant non-small cell lung cancer," dated Nov. 6, 2020.
Monk et al., "MILO/ENGOT-ov11: Binimetinib Versus Physician's Choice Chemotherapy in Recurrent or Persistent Low-Grade Serous Carcinomas of the Ovary, Fallopian Tube, or Primary Peritoneum", Journal of Clinical Oncology, 38 (32): 3753-3770, Aug. 21, 2020.
Shapiro et al., "Phase Ib study of the MEK inhibitor cobimetinib (GDC-0973) in combination with the PI3K inhibitor pictilisib (GDC-0941) in patients with advanced solid tumors", Invest. New Drugs (2020) 38:419-432.
Gershenson et al., "Trametinib versus standard of care in patients with recurrent low-grade serous ovarian cancer (GOG 281/LOGS): an international, randomised, open-label, multicentre, phase 2/3 trial", www.thelancet.com, vol. 399: 541-553, Feb. 5, 2022.
Mak et al., "A phase Ib dose-finding, pharmacokinetic study of the focal adhesion kinase inhibitor GSK2256098 and trametinib in patients with advanced solid tumours", British Journal of Cancer (2019) 120:975-981.
Shapiro et al., "A phase Ib open-label dose escalation study of the safety, pharmacokinetics, and pharmacodynamics of cobimetinib (GDC-0973) and ipatasertib (GDC-0068) in patients with locally advanced or metastatic solid tumors", Invest. New Drugs (Feb. 2021.) 39(1):163-174.
Weekes et al., "A Phase Ib Study to Evaluate the MEK Inhibitor Cobimetinib in Combination with the ERK1/2 Inhibitor GDC-0994 in Patients with Advanced Solid Tumors", The Oncologist (2020); 25:833-e1438.

(56) References Cited

OTHER PUBLICATIONS

Aung et al., "A phase II trial of GSK2256098 and trametinib in patients with advanced pancreatic ductal adenocarcinoma (PDAC)(MOBILITY-002 Trial, NCT02428270)", Journal of Clinical Oncology, 36, No. 4 suppl. (Feb. 1, 2018), 409-409.

Algazi et. al., "Continuous versus intermittent BRAF and MEK inhibition in patients with BRAF mutated melanoma: a randomized phase 2 trial", Nat Med. (Oct. 2020); 26(10): 1564-1568.

Gonzalez-Cao et al., "Intermittent BRAF inhibition in advanced BRAF mutated melanoma results of a phase II randomized trial", Nature Communications (2021), 12:7008, 6 pages.

Stewart et al., "KRAS genomic status predicts the sensitivity of ovarian cancer cells to decitabine", Cancer Res. Jul. 15, 2015 ; 75(14): 2897-2906.

Understanding Chemotherapy [online]. Cancer.Net Oct. 10, 2017 [retrieved on Feb. 25, 2022]. Retrieved from the internet: <http://www.cancer.net/navigating-cancer-care/how-cancer-treated/chemotherapy/understanding-chemotherapy> (Year: 2017), 4 pages.

Fernandez et al., "Differences in MEK inhibitor efficacy in molecularly characterized low-grade serous ovarian cancer cell lines", Am J Cancer Res., 6(1) pp. 2235-2251. (Year: 2016).

Molnar et al., "Pan-RAF and MEK vertical inhibition enhances therapeutic response in non-V600 BRAF mutant cells", BMC Cancer, May 8, 2018, vol. 18, Art. No. 542, pp. 1-11.

International Search Report and Written Opinion for International Patent Application No. PCT/US2021/029435 dated Aug. 3, 2021, 9 pages.

Hamid et al., "Safety, Clinical Activity, and Biological Correlates of Response in Patients with Metastatic Melanoma: Results from a Phase I Trial of Atezolizumab", Clinical Cancer Research, Oct. 15, 2019, vol. 25, No. 20, p. 6061-6072.

Institute of Cancer Research, United Kingdom, Frame: "A Phase I Trial of the Combination of VS-6063 (FAK Inhibitor) and RO5126766 (CH5126776) (a Dual RAF/MEK Inhibitor) in Patients With Advanced Solid Tumours", Jun. 24, 2020 [online]. [Retrieved on Sep. 30, 2021). Retrieved from the Internet <URL: https://clinicaltrials.gov/ct2/history/NCT03875820?V_6=View#StudyPageTop>, p. 1-9.

International Search Report and Written Opinion for International Patent Application No. PCT/US2021/041439 dated Nov. 12, 2021, 9 pages.

International Search Report and Written Opinion for International Patent Application No. PCT/US2022/015262 dated Jul. 7, 2022, 16 pages.

International Search Report and Written Opinion for International Patent Application No. PCT/US2022/079109 dated Mar. 10, 2023, 11 pages.

International Search Report and Written Opinion for International Patent Application No. PCT/US2022/038434, dated Oct. 6, 2022, 10 pages.

Guo et al. "Intermittent schedules of the oral RAF-MEK inhibitor CH5126766/NS-6766 in patients with RAS/RAF-mutant solid tumours and multiple myeloma: a single-centre, open-label, phase 1 dose-escalation and basket dose-expansion study," The Lancet Oncology, Oct. 28, 2020 (Oct. 28, 2020), vol. 21, Issue 11, pp. 1478-1488.

International Search Report and Written Opinion for International Application No. PCT/US2022/078771, dated Mar. 15, 2023, 13 pages.

Asati et al., "PI3K/Akt/mTOR and Ras/Raf/MEK/ERK signaling pathways inhibitors as anticancer agents: Structural and pharmacological perspectives", European Journal of Medicinal Chemistry 109 (2016) 314-341.

Tolcher et al., "Rational Approaches for Combination Therapy Strategies Targeting the MAP Kinase Pathway in Solid Tumors", Molecular Cancer Therapies, 17(1), Jan. 2018, 14 pages.

International Search Report and Written Opinion for International Patent Application No. PCT/US2023/023932, dated Jul. 7, 2023, 7 pages.

International Search Report and Written Opinion for International Patent Application No. PCT/US2022/081248, dated Jun. 15, 2023, 13 pages.

International Search Report and Written Opinion for International Patent Application No. PCT/US23/61150 dated Jul. 27, 2023, 20 pages.

Holck. "Phospho-ERK levels as predictors for chemotherapy of rectal carcinoma" Oncotarget, Online, Mar. 1, 2019; Figure 1; p. 1746, 1st column, 1st paragraph; p. 1753, 2nd column, 3rd paragraph.

International Preliminary Report on Patentability ("IPRP") for International Patent Application No. PCT/US2022/015262, dated Aug. 17, 2023, 8 pages.

* cited by examiner

SOLID FORMS OF A DUAL RAF/MEK INHIBITOR

CROSS-REFERENCE TO RELATED APPLICATIONS

This application claims priority to U.S. Provisional Application No. 63/349,815 filed Jun. 7, 2022, which is incorporated herein by reference in its entirety.

BACKGROUND

Components of the RAS/RAF/MEK/ERK (MAPK) signal transduction pathway represent opportunities for the treatment of abnormal cell growth, e.g., cancer. For example, mutations in RAS/RAF/MEK/ERK are frequently found in human cancers. These mutants result in a constitutively active MAPK kinase cascade, leading to tumor cell proliferation, differentiation, survival, and migration. Selective inhibitors of certain components of the RAS/RAF/MEK/ERK signal transduction pathway, such as RAS, RAF, MEK and ERK, are useful in the treatment of abnormal cell growth, in particular cancer, in mammals.

Due to the severity and breadth of diseases and disorders associated with abnormal cell growth, e.g., cancer, there is a need for effective therapeutic means and methods for treatment. The present disclosure relates to solid forms of compounds of Formula I, or a pharmaceutically acceptable salt thereof (e.g., a compound of Formula II), their pharmaceutical compositions and oral dosage forms, processes for their preparation, and methods for their use, which address the needs and provide exemplary advantages.

SUMMARY

Described herein, in part, are solid forms of a dual RAF/MEK inhibitor (e.g., a compound of Formula II), pharmaceutical compositions and oral dosage forms thereof, methods of treating cancer, and processes for preparing solid forms of a dual RAF/MEK inhibitor (e.g., a compound of Formula II) and pharmaceutical compositions and oral dosage forms thereof.

In an aspect, provided herein is crystalline Form 1 of a compound of Formula II:

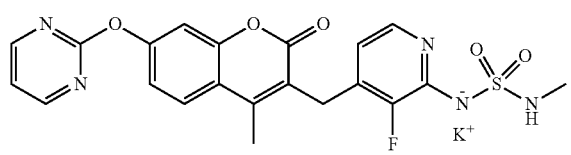

(II)

wherein Form 1 is substantially free of other form or pattern of the compound of Formula II.

In another aspect, provided herein is crystalline Form 1 of a compound of Formula II:

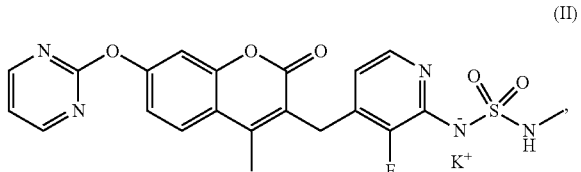

(II)

wherein Form 1 is substantially free of an impurity.

In another aspect, provided herein is crystalline Form 1 of a compound of Formula II:

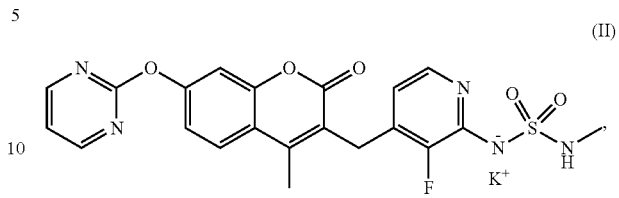

(II)

wherein Form 1 exhibits an X-ray power diffraction pattern comprising a characteristic XRPD peak at the following diffraction angle (2θ (degrees))=9.0±0.2. In some embodiments, the X-ray power diffraction pattern of Form 1 further comprises at least one peak selected from the following diffraction angles (2θ (degrees))=4.5±0.2, 14.7±0.2, 18.1±0.2, and 22.7±0.2.

In another aspect, provided herein is crystalline Form 8 of a compound of Formula II:

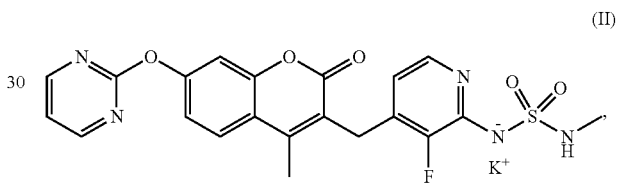

(II)

wherein Form 8 exhibits an X-ray power diffraction pattern comprising a characteristic XRPD peak at the following diffraction angle (2θ (degrees))=9.9±0.2. In some embodiments, Form 8 exhibits an X-ray power diffraction pattern comprising peaks at the following diffraction angles (2θ (degrees))=9.9±0.2, 16.8±0.2, and 20.2±0.2.

In another aspect, provided herein is crystalline Form 10 of a compound of Formula II:

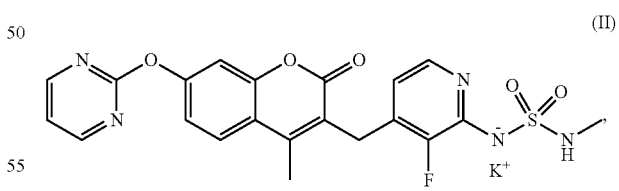

(II)

wherein the Form 10 exhibits an X-ray power diffraction pattern comprising a characteristic XRPD peak at the following diffraction angle (2θ (degrees))=11.7±0.2. In some embodiments, Form 10 exhibits an X-ray power diffraction pattern comprising peaks at the following diffraction angles (2θ (degrees))=11.7±0.2, 12.5±0.2, and 25.5±0.2, wherein the compound is a hydrate.

In an aspect, provided herein is a method of preparing crystalline Form 1 of a compound of Formula II:

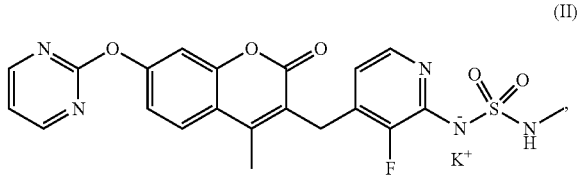 [SMILES: CNS(=O)(=O)Nc1nccc(Cc2c(C)c3ccc(Oc4ncccn4)cc3oc2=O)c1F ; [K+]]

(II)

comprising: (i) contacting a solution comprising a compound of Formula I:

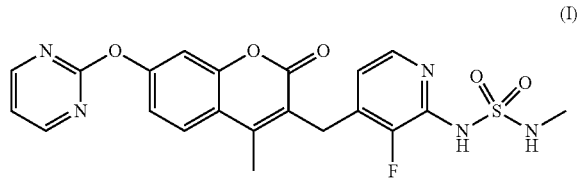 [SMILES: CNS(=O)(=O)Nc1nccc(Cc2c(C)c3ccc(Oc4ncccn4)cc3oc2=O)c1F]

(I)

in one or more solvent, with potassium hydroxide to form a mixture; (ii) heating the mixture prepared according to step (i) to about 40° C. to about 60° C.; (iii) cooling the heated mixture of step (ii) to about −10° C. to about 5° C. to form a precipitate; (iv) filtering the precipitate of step (iii) to isolate a solid; and (v) drying the solid from step (iv), to give Form 1. In some embodiments, the drying comprises drying the solid under reduced pressure at elevated temperature.

In an aspect, provided herein is a pharmaceutical composition comprising crystalline Form 1 of a compound of Formula II described herein and a pharmaceutically acceptable carrier.

In an aspect, provided herein is a method of treating cancer in a subject in need thereof, comprising administering to the subject a therapeutically effective amount of crystalline Form 1 of a compound of Formula II described herein or a pharmaceutical composition or an oral dosage form described herein.

DETAILED DESCRIPTION

Figure 1A:
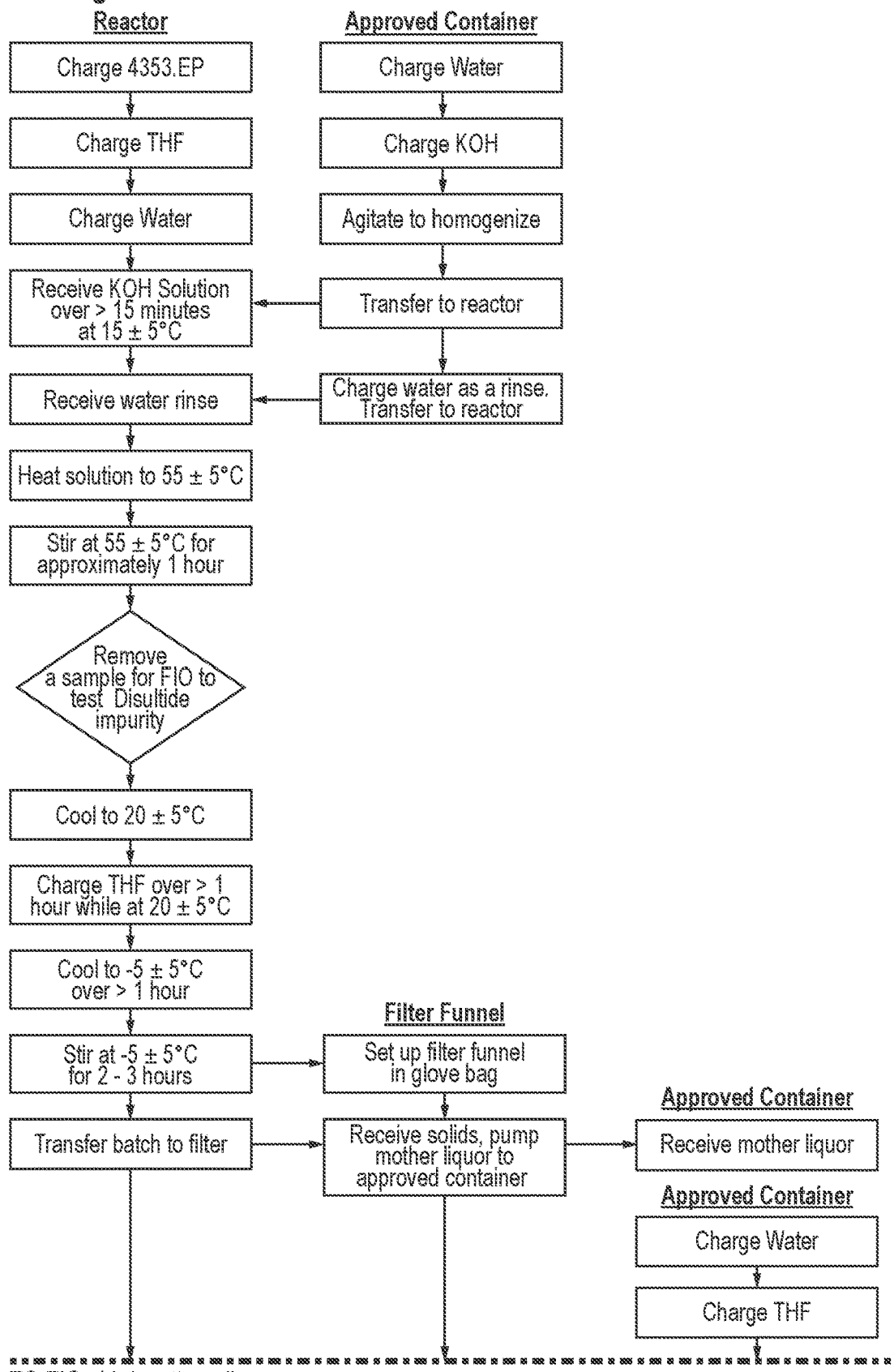
FIG. 1A shows a flow chart of an exemplary manufacturing process of VS-6766.
Figure 1A:
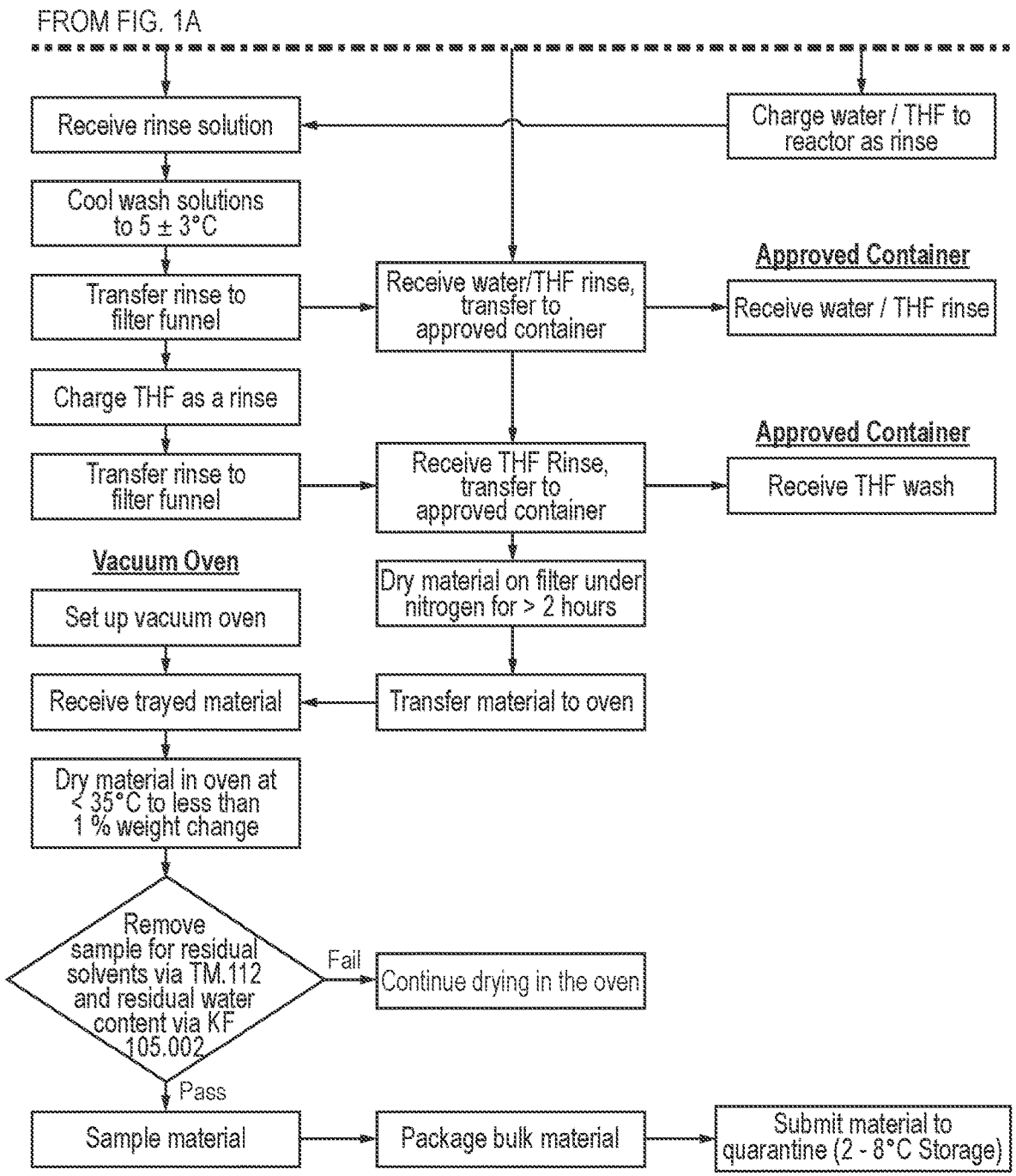

The present disclosure, in part, provides solid forms of a dual RAF/MEK inhibitor (e.g., a compound of Formula II), pharmaceutical compositions and oral dosage forms thereof, methods of treating cancer, and processes for preparing solid forms of a dual RAF/MEK inhibitor (e.g., a compound of Formula II) and pharmaceutical compositions and oral dosage forms thereof.

Definitions

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

As used herein, a "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) or a non-human animal, e.g., a mammal such as primates (e.g., cynomolgus monkeys, rhesus monkeys), cattle, pigs, horses, sheep, goats, rodents, cats, or dogs. In some embodiments, the subject is a human. In some embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (also "therapeutic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, "prophylactic treatment" contemplates an action that occurs before a subject begins to suffer from the specified disease, disorder or condition.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

The term, "oral dosage form," as used herein, refers to a composition or medium used to administer an agent to a subject. Typically, an oral dosage form is administered via the mouth, however, "oral dosage form" is intended to cover any substance which is administered to a subject and is absorbed across a membrane, e.g., a mucosal membrane, of the gastrointestinal tract, including, e.g., the mouth, esophagus, stomach, small intestine, large intestine, and colon. For example, "oral dosage form" covers a solution which is administered through a feeding tube into the stomach.

A "cycle", as used herein in the context of a cycle of administration of a drug, refers to a period for which a drug is administered to a patient. In some embodiments, one cycle is four weeks.

As used herein, the term "isolation" or "isolating" includes, but is not limited to, the action of obtaining one or more compounds by collection during or after a process step as disclosed herein, and the action of obtaining one or more compounds by separation of one or more compounds from one or more other chemical entities during or after a process step as disclosed herein.

The term "collection" or "collecting" refers to any action(s) known in the art for this purpose, including, but not limited to, decanting a mother liquor from a solid to obtain one or more compounds, and evaporation of liquid media in a solution or other mixture to afford a solid, oil, or other residue that includes one or more compounds. The solid can be crystalline, partially crystalline, amorphous, containing one or more solid forms, a powder, granular, of varying particle sizes, of varying surface areas, of uniform particle size, among other characteristics known in the art. An oil can vary in color and viscosity, and include one or more solid forms as a heterogeneous mixture, among other characteristics known in the art.

The term "separation" or "separating" refers to any action(s) known in the art for this purpose, including, but not limited to, isolating one or more compounds from a solution or mixture using, for example, seeded or seedless crystallization or other precipitation techniques (e.g., adding an anti-solvent to a solution to induce compound precipitation; heating a solution, then cooling to induce compound precipitation; scratching the surface of a solution with an implement to induce compound precipitation), and distillation techniques.

Isolating one or more compounds can involve preparation of a salt, solvate, or a hydrate of the compounds thereof, of a mixture thereof, then collecting or separating as described above.

As used herein, and unless otherwise specified, a "polymorph" describes a crystalline material, e.g., a crystalline form, of a compound that can exist in two or more crystalline structures.

Compounds of the present disclosure include crystalline and amorphous forms of the compounds, including, for example, solvates, hydrates, co-crystals, unsolvated forms (including anhydrates), conformational forms, tautomeric forms, or disordered crystalline forms thereof, as well as mixtures thereof.

As used herein, and unless otherwise specified, a particular form of a compound of Formula II described herein is meant to encompass a solid form of a compound of Formula II, or a salt, solvate, or hydrate thereof, among others.

As used herein, and unless otherwise specified, the term "crystalline," when used to describe a substance, component, or product, means that the substance, component, or product is substantially crystalline as determined, for example, by X-ray diffraction. See, e.g., Remington: The Science and Practice of Pharmacy, Lippincott Williams & Wilkins, $21^{st}$ ed. (2005). The crystalline substance, component, or product has a highly regular chemical structure. The molecules are arranged in a regular, periodic manner in the 3-dimensional space of the crystalline lattice.

As used herein, and unless otherwise specified, the term "crystalline form," "crystal form," and related terms herein refer to the various crystalline material comprising a given substance, including single-component crystal forms and multiple-component crystal forms, and including, but not limited to, polymorphs, solvates, hydrates, co-crystals and other molecular complexes, as well as salts, solvates of salts, hydrates of salts, other molecular complexes of salts, and polymorphs thereof. In some embodiments, a crystal form of a substance can be substantially free of amorphous forms or other crystal forms. In other embodiments, a crystal form of a substance can contain about 1%, about 2%, about 3%, about 4%, about 5%, about 10%, about 15%, about 20%, about 25%, about 30%, about 35%, about 40%, about 45% or about 50% of one or more amorphous form(s) or other crystal form(s) on a weight or molar basis.

Certain crystal forms of a substance can be obtained by a number of methods, such as, without limitation, melt recrystallization, melt cooling, solvent recrystallization, recrystallization in confined spaces, such as, e.g., in nanopores or capillaries, recrystallization on surfaces or templates, such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, solvent-drop grinding, microwave-induced precipitation, sonication-induced precipitation, laser-induced precipitation, or precipitation from a supercritical fluid, or a combination thereof. In some embodiments, the term "isolating" also encompasses purifying.

As used herein, "XRPD" refers to X-ray powder diffraction.

Techniques for characterizing crystal forms and amorphous forms can include, but are not limited to, thermal gravimetric analysis (TGA), differential scanning calorimetry (DSC), X-ray powder diffractometry (XRPD), single crystal X-ray diffractometry, vibrational spectroscopy, e.g., infrared (IR) and Raman spectroscopy, solid-state nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies.

As used herein, and unless otherwise specified, the term "peak," when used in connection with the spectra or data presented in graphical form (e.g., XRPD, IR, Raman, and NMR spectra), refers to a peak or other special feature that one skilled in the art would recognize as not attributable to background noise. The term "significant peak" refers to peaks at least the median size (e.g., height) of other peaks in the spectrum or data, or at least 1.5, 2, or 2.5 times the background level in the spectrum or data.

As used herein, and unless otherwise specified, the term "amorphous," "amorphous form," and related terms herein mean that the substance, component or product in question is not substantially crystalline as determined, for example, by X-ray diffraction. In some embodiments, an amorphous form of a substance can be substantially free of other amorphous forms or crystal forms. In some embodiments, an amorphous form of a substance can comprise one or more disordered crystalline forms. In other embodiments, an amorphous form of a substance can contain about 1%, about 2%, about 3%, about 4%, about 5%, about 10%, about 15%, about 20%, about 25%, about 30%, about 35%, about 40%, about 45% or about 50% of one or more other amorphous forms or crystal forms on a weight or molar basis.

Amorphous forms of a substance can be obtained by several methods, as known in the art. Such methods include, but are not limited to, heating, melt cooling, rapid melt cooling, solvent evaporation, rapid solvent evaporation, desolvation, sublimation, grinding, cryo-grinding, spray drying, and freeze drying.

As used herein, a polymorph, a crystal form, or a solid form of a compound described herein may be described by reference to patterns, spectra, or other graphical data as "substantially" shown or depicted in a figure, or by one or more data points. It will be appreciated that patterns, spectra, and other graphical data can be shifted in their positions, relative intensities, or other values due to a number of factors known to those of skill in the art. For example, in the crystallographic and powder X-ray diffraction arts, shifts in peak positions or the relative intensities of one or more peaks of a pattern can occur because of, without limitation, the equipment used, the sample preparation protocol, preferred packing and orientations, the radiation source, operator error, method and length of data collection, or the like. However, those of ordinary skill in the art will be able to compare the figures herein with patterns, etc. generated for an unknown form of, in this case, the compound of Formula II, and confirms its identity with the forms disclosed herein. The same holds true for other techniques which may be reported herein.

As used herein and unless otherwise specified, a solid form or composition that is "substantially free" of a compound (e.g., other form or pattern or impurity) means that the solid form or composition contains less than about 20 percent by weight, less than about 10 percent by weight, less than about 5 percent by weight, less than about 4 percent by weight, less than about 3 percent by weight, less than about 2 percent by weight, less than about 1 percent by weight, less than about 0.5% by weight of the compound, or less than about 0.1 percent by weight of the compound (e.g., other form or pattern or impurity).

As used herein, and unless otherwise specified, the term "substantially pure" when used to describe a polymorph, a crystal form, or a solid form of a compound described herein means a solid form of the compound that comprises a particular solid form and is substantially free of other solid forms of the compound or other compounds. A representative substantially pure solid form comprises greater than about 80% by weight of one solid form of the compound and less than about 20% by weight of other solid forms of the compound or other compounds; greater than about 90% by weight of one solid form of the compound and less than about 10% by weight of other solid forms of the compound or other compounds; greater than about 95% by weight of one solid form of the compound and less than about 5% by weight of other solid forms of the compound or other compounds; greater than about 97% by weight of one solid form of the compound and less than about 3% by weight of other solid forms of the compound or other compounds; or greater than about 99% by weight of one solid form of the compound and less than about 1% by weight of other solid forms of the compound or other compounds.

As used herein, and unless otherwise specified, a crystal form that is "essentially free" of water or solvent in the crystal lattice has a quantity of water or solvent in the crystal lattice which is, in some embodiments, approximately near the limit of detection, in other embodiments, approximately at the limit of detection, and in other embodiments, approximately below the limit of detection for solvent or water in the crystal lattice when measured using a conventional solid-state analytical technique, e.g., a technique described herein. In some embodiments, the solid-state analytical technique used to determine the quantity of water or solvent in the crystal lattice is thermogravimetric analysis. In other embodiments, the solid-state analytical technique used to determine the quantity of water or solvent in the crystal lattice is Karl Fischer analysis. In other embodiments, a crystal form which is "essentially free" of water or solvent in the crystal lattice has a quantity of water or solvent which is less than about 5%, less than about 4%, less than about 3%, less than about 2%, less than about 1%, less than about 0.9%, less than about 0.8%, less than about 0.7%, less than about 0.6%, less than about 0.5%, less than about 0.4%, less than about 0.3%, less than about 0.2%, less than about 0.1%, less than about 0.05%, or less than about 0.01% of the total weight of the crystal form.

As used herein, and unless otherwise specified, the term "stable" refers to a compound or composition that does not readily decompose or change in chemical makeup or physical state. A stable compound or composition provided herein does not significantly decompose under normal manufacturing or storage conditions. In some embodiments, the term "stable," when used in connection with a formulation or a dosage form, means that the active ingredient of the formulation or dosage form remains unchanged in chemical makeup or physical state for a specified amount of time and does not significantly degrade or aggregate or become otherwise modified (e.g., as determined, for example, by HPLC, FTIR, or XRPD). In some embodiments, about 70 percent or greater, about 80 percent or greater, about 90 percent or greater, about 95 percent or greater, about 98 percent or greater, or about 99 percent or greater of the compound remains unchanged after the specified period. In one embodiment, a solid form provided herein is stable upon long-term storage (e.g., no significant change in the solid form after about 1, 2, 3, 4, 5, 6, 7, 8, 9, 10, 11, 12, 18, 24, 30, 36, 42, 48, 54, 60, or greater than about 60 months).

As used herein, the term "pattern" with respect to the compound of Formula II refers to metastable forms of the compound of Formula II.

As used herein, a "filler" refers to an excipient/carrier in a pharmaceutical composition that lacks pharmacological activity but may be pharmaceutically necessary or desirable, e.g. to enhance or improve the properties of the pharmaceutical blend for manufacturing or physiological purposes. For example, a filler may be used to increase the bulk of a potent drug whose mass is too small for manufacture or administration.

As used herein a "lubricant" refers to an excipient/carrier which for example prevents ingredients and excipients to lump together, and/or sticking to the capsule filling machine. A lubricant may also ensure that the formation, filing and ejection of the capsule can occur, for example by lowering friction. Examples of lubricants are talc, silicon dioxide (silica), fatty acids or fatty acid salts, such as magnesium stearate, sodium stearate fumarate, stearic acid, etc.

As used herein, the term "sieving" refers to putting or passing a particulate solid (e.g., a compound of Formula II or a pharmaceutically acceptable carrier) through a utensil having a plurality of meshed or perforated openings, slits, or holes, e.g., to separate fine particles of loss matter from coarser ones.

The term "blending" refers to the mixing of pharmaceutical ingredients to form a mixture of the ingredients, e.g. active pharmaceutical ingredient (API) and pharmaceutically acceptable carrier(s), as defined by pharmaceutical specifications in the compendial references using a variety of equipment such as, but not limited to, "V"-blenders, bin-blenders, cone-blenders.

As used herein, the term "high-shear" can be related to many different factors within the process, and is not merely a function of tip speed and/or revolutions per minute, though it may be referred to those values in describing the high speed shearing and speed of the blades within the blender/mixer.

The term "encapsulation" refers to a range of techniques used to enclose medicines in a shell, e.g. a two-piece capsule, such as a two-piece hard shell capsule. The capsule referred to herein may be taken orally. Capsules may be designed with a telescoping cap and body manufactured from e.g. gelatin or cellulose.

Compounds

Provided herein, in some embodiments, are compounds that are dual RAF/MEK inhibitors. An exemplary dual RAF/MEK inhibitor is a compound of Formula I having the following structure:

(I)

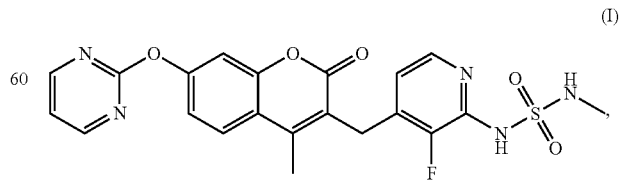

or a pharmaceutically acceptable salt, solvate, or hydrate thereof.

In some embodiments, the compound of Formula I is:

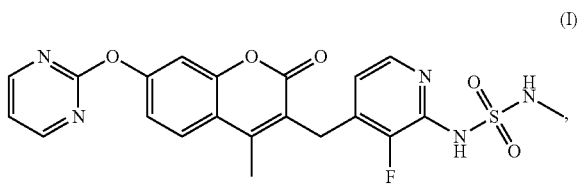 [SMILES: CNS(=O)(=O)Nc1nccc(Cc2c(C)c3ccc(Oc4ncccn4)cc3oc2=O)c1F]

(I)

which is also referred to herein VS-6766 free form.

The compound of Formula I may be synthesized according to the synthetic methods described in WO2007091736 and WO2013035754, which are incorporated herein by its entirety.

In some embodiments, the dual RAF/MEK inhibitor is a pharmaceutically acceptable salt of the compound of Formula I. In some embodiments, the dual RAF/MEK inhibitor is a potassium salt of the compound of Formula I, which is also referred to herein as VS-6766 or Compound 1.

For example, Compound 1, as referred to herein corresponds to a compound with the following structure:

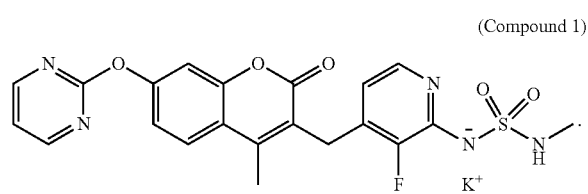 [SMILES: CNS(=O)(=O)[N-]c1nccc(Cc2c(C)c3ccc(Oc4ncccn4)cc3oc2=O)c1F ; [K+]]

(Compound 1)

Compound 1 is also disclosed herein as a compound of Formula II.

Different solid forms of an active pharmaceutical ingredient may have different physicochemical properties and may give rise to solid forms of the active pharmaceutical ingredient with improved properties, for example, desirable processing properties, such as ease of handling, ease of processing, storage stability, and ease of purification, improved dissolution profile, dissolution rates, chemical stability, physical stability, bioavailability, storage conditions, shelf-life, purity, process reproducibility, or formulation.

In some embodiments, disclosed herein are solid forms of a compound of Formula II that are substantially free of other form or pattern of the compound of Formula II or an impurity.

Solid Forms
Form 1

In an aspect, provided herein is crystalline Form 1 of a compound of Formula II:

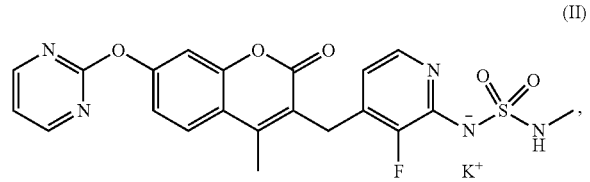 [SMILES: CNS(=O)(=O)[N-]c1nccc(Cc2c(C)c3ccc(Oc4ncccn4)cc3oc2=O)c1F ; [K+]]

(II)

wherein Form 1 is substantially free of other form or pattern of the compound of Formula II. In some embodiments, the other form or pattern is selected from the group consisting of Form 8, Form 10, Pattern 2, Pattern 3, Pattern 5, Pattern 6, Pattern 7, Pattern 11, and Pattern 12, and combinations thereof.

In some embodiments, Form 1 exhibits an X-ray power diffraction pattern comprising a characteristic XRPD peak at the following diffraction angle (2θ (degrees))=9.0±0.2. In some embodiments, Form 1 exhibits an X-ray power diffraction pattern comprising a characteristic XRPD peak at the following diffraction angle (2θ (degrees))=4.5±0.2. In some embodiments, Form 1 exhibits an X-ray power diffraction pattern comprising a characteristic XRPD peak at the following diffraction angle (2θ (degrees))=14.7±0.2. In some embodiments, Form 1 exhibits an X-ray power diffraction pattern comprising a characteristic XRPD peak at the following diffraction angle (2θ (degrees))=18.1±0.2. In some embodiments, Form 1 exhibits an X-ray power diffraction pattern comprising a characteristic XRPD peak at the following diffraction angle (2θ (degrees))=22.7±0.2. In some embodiments, Form 1 exhibits an X-ray power diffraction pattern comprising peaks at the following diffraction angles (2θ (degrees))=4.5±0.2 and 9.0±0.2. In some embodiments, Form 1 exhibits an X-ray power diffraction pattern comprising peaks at the following diffraction angles (2θ (degrees))=4.5±0.2, 9.0±0.2, and 14.7±0.2. In some embodiments, Form 1 exhibits an X-ray power diffraction pattern comprising peaks at the following diffraction angles (2θ (degrees))=4.5±0.2, 9.0±0.2, 14.7±0.2, and 18.1±0.2. In some embodiments, Form 1 exhibits an X-ray power diffraction pattern comprising peaks at the following diffraction angles (2θ (degrees))=4.5±0.2, 9.0±0.2, 14.7±0.2, 18.1±0.2. and 22.7±0.2. In some embodiments, Form 1 exhibits an X-ray power diffraction pattern comprising peaks at the following diffraction angles (2θ (degrees))= 9.0±0.2 and 18.1±0.2. In some embodiments, Form 1 exhibits an X-ray power diffraction pattern comprising peaks at the following diffraction angles (2θ (degrees))=4.5±0.2 and 18.1±0.2. In some embodiments, Form 1 exhibits an X-ray power diffraction pattern comprising at least two peaks selected from the following diffraction angles (2θ (degrees))=4.5±0.2, 9.0±0.2, 14.7±0.2, 18.1±0.2. and 22.7±0.2. In some embodiments, Form 1 exhibits an X-ray power diffraction pattern comprising at least three peaks selected from the following diffraction angles (2θ (degrees))=4.5±0.2, 9.0±0.2, 14.7±0.2, 18.1±0.2, and 22.7±0.2. In some embodiments, Form 1 exhibits an X-ray power diffraction pattern comprising at least four peaks selected from the following diffraction angles (2θ (degrees))=4.5±0.2, 9.0±0.2, 14.7±0.2, 18.1±0.2, and 22.7±0.2.

In some embodiments, Form 1 exhibits an X-ray power diffraction pattern further comprising at least one characteristic XRPD peak selected from diffraction angles (2θ (degrees))=7.3±0.2, 10.7±0.2, 13.5±0.2, 16.6±0.2, 17.1±0.2, 17.7±0.2, and 19.4±0.2. In some embodiments, Form 1 exhibits an X-ray power diffraction pattern further comprising at least one characteristic XRPD peak selected from diffraction angles (2θ (degrees))=21.9±0.2, 23.1±0.2, 25.1±0.2, 27.0±0.2, 32.3±0.2, and 39.4±0.2.

In some embodiments, Form 1 exhibits an X-ray power diffraction pattern comprising at least two peaks selected from the following diffraction angles (2θ (degrees))= 4.5±0.2, 7.7±0.2, 9.0±0.2, 14.7±0.2, 17.1±0.2, 18.1±0.2, 19.4±0.2, and 22.7±0.2. In some embodiments, Form 1 exhibits an X-ray power diffraction pattern comprising at least three peaks selected from the following diffraction angles (2θ (degrees))=4.5±0.2, 7.7±0.2, 9.0±0.2, 14.7±0.2, 17.1±0.2, 18.1±0.2, 19.4±0.2, and 22.7±0.2. In some embodiments, Form 1 exhibits an X-ray power diffraction pattern comprising at least four peaks selected from the following diffraction angles (2θ (degrees))=4.5±0.2, 7.7±0.2, 9.0±0.2, 14.7±0.2, 17.1±0.2, 18.1±0.2, 19.4±0.2, and 22.7±0.2.

In some embodiments, Form 1 exhibits an X-ray power diffraction pattern comprising a characteristic XRPD peak at the following diffraction angle (2θ (degrees))=9.0±0.3. In some embodiments, Form 1 exhibits an X-ray power diffraction pattern comprising a characteristic XRPD peak at the following diffraction angle (2θ (degrees))=4.5±0.3. In some embodiments, Form 1 exhibits an X-ray power diffraction pattern comprising a characteristic XRPD peak at the following diffraction angle (2θ (degrees))=14.7±0.3. In some embodiments, Form 1 exhibits an X-ray power diffraction pattern comprising a characteristic XRPD peak at the following diffraction angle (2θ (degrees))=18.1±0.3. In some embodiments, Form 1 exhibits an X-ray power diffraction pattern comprising a characteristic XRPD peak at the following diffraction angle (2θ (degrees))=22.7±0.3. In some embodiments, Form 1 exhibits an X-ray power diffraction pattern comprising peaks at the following diffraction angles (2θ (degrees))=4.5±0.3 and 9.0±0.3. In some embodiments, Form 1 exhibits an X-ray power diffraction pattern comprising peaks at the following diffraction angles (2θ (degrees))=4.5±0.3, 9.0±0.3, and 14.7±0.3. In some embodiments, Form 1 exhibits an X-ray power diffraction pattern comprising peaks at the following diffraction angles (2θ (degrees))=4.5±0.3, 9.0±0.3, 14.7±0.3, and 18.1±0.3. In some embodiments, Form 1 exhibits an X-ray power diffraction pattern comprising peaks at the following diffraction angles (2θ (degrees))=4.5±0.3, 9.0±0.3, 14.7±0.3, 18.1±0.3. and 22.7±0.3. In some embodiments, Form 1 exhibits an X-ray power diffraction pattern comprising peaks at the following diffraction angles (2θ (degrees))=9.0±0.3 and 18.1±0.3. In some embodiments, Form 1 exhibits an X-ray power diffraction pattern comprising peaks at the following diffraction angles (2θ (degrees))=4.5±0.3 and 18.1±0.3. In some embodiments, Form 1 exhibits an X-ray power diffraction pattern comprising at least two peaks selected from the following diffraction angles (2θ (degrees))=4.5±0.3, 9.0±0.3, 14.7±0.3, 18.1±0.3. and 22.7±0.3. In some embodiments, Form 1 exhibits an X-ray power diffraction pattern comprising at least three peaks selected from the following diffraction angles (2θ (degrees))=4.5±0.3, 9.0±0.3, 14.7±0.3, 18.1±0.3, and 22.7±0.3. In some embodiments, Form 1 exhibits an X-ray power diffraction pattern comprising at least four peaks selected from the following diffraction angles (2θ (degrees))=4.5±0.3, 9.0±0.3, 14.7±0.3, 18.1±0.3, and 22.7±0.3.

In some embodiments, Form 1 exhibits an X-ray power diffraction pattern further comprising at least one characteristic XRPD peak selected from diffraction angles (2θ (degrees))=7.3±0.3, 10.7±0.3, 13.5±0.3, 16.6±0.3, 17.1±0.3, 17.7±0.3, and 19.4±0.3. In some embodiments, Form 1 exhibits an X-ray power diffraction pattern further comprising at least one characteristic XRPD peak selected from diffraction angles (2θ (degrees))=21.9±0.3, 23.1±0.3, 25.1±0.3, 27.0±0.3, 32.3±0.3, and 39.4±0.3.

In some embodiments, Form 1 exhibits an X-ray power diffraction pattern comprising at least two peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3. In some embodiments, Form 1 exhibits an X-ray power diffraction pattern comprising at least three peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3. In some embodiments, Form 1 exhibits an X-ray power diffraction pattern comprising at least four peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3.

In some embodiments, Form 1 exhibits an X-ray power diffraction pattern comprising a characteristic XRPD peak at the following diffraction angle (2θ (degrees))=9.0±0.5. In some embodiments, Form 1 exhibits an X-ray power diffraction pattern comprising a characteristic XRPD peak at the following diffraction angle (2θ (degrees))=4.5±0.5. In some embodiments, Form 1 exhibits an X-ray power diffraction pattern comprising a characteristic XRPD peak at the following diffraction angle (2θ (degrees))=14.7±0.5. In some embodiments, Form 1 exhibits an X-ray power diffraction pattern comprising a characteristic XRPD peak at the following diffraction angle (2θ (degrees))=18.1±0.5. In some embodiments, Form 1 exhibits an X-ray power diffraction pattern comprising a characteristic XRPD peak at the following diffraction angle (2θ (degrees))=22.7±0.5. In some embodiments, Form 1 exhibits an X-ray power diffraction pattern comprising peaks at the following diffraction angles (2θ (degrees))=4.5±0.5 and 9.0±0.5. In some embodiments, Form 1 exhibits an X-ray power diffraction pattern comprising peaks at the following diffraction angles (2θ (degrees))=4.5±0.5, 9.0±0.5, and 14.7±0.5. In some embodiments, Form 1 exhibits an X-ray power diffraction pattern comprising peaks at the following diffraction angles (2θ (degrees))=4.5±0.5, 9.0±0.5, 14.7±0.5, and 18.1±0.5. In some embodiments, Form 1 exhibits an X-ray power diffraction pattern comprising peaks at the following diffraction angles (2θ (degrees))=4.5±0.5, 9.0±0.5, 14.7±0.5, 18.1±0.5. and 22.7±0.5. In some embodiments, Form 1 exhibits an X-ray power diffraction pattern comprising peaks at the following diffraction angles (2θ (degrees))=9.0±0.5 and 18.1±0.5. In some embodiments, Form 1 exhibits an X-ray power diffraction pattern comprising peaks at the following diffraction angles (2θ (degrees))=4.5±0.5 and 18.1±0.5. In some embodiments, Form 1 exhibits an X-ray power diffraction pattern comprising at least two peaks selected from the following diffraction angles (2θ (degrees))=4.5±0.5, 9.0±0.5, 14.7±0.5, 18.1±0.5. and 22.7±0.5. In some embodiments, Form 1 exhibits an X-ray power diffraction pattern comprising at least three peaks selected from the following diffraction angles (2θ (degrees))=4.5±0.5, 9.0±0.5, 14.7±0.5, 18.1±0.5, and 22.7±0.5. In some embodiments, Form 1 exhibits an X-ray power diffraction pattern comprising at least four peaks selected from the following diffraction angles (2θ (degrees))=4.5±0.5, 9.0±0.5, 14.7±0.5, 18.1±0.5, and 22.7±0.5.

In some embodiments, Form 1 exhibits an X-ray power diffraction pattern further comprising at least one characteristic XRPD peak selected from diffraction angles (2θ (degrees))=7.3±0.5, 10.7±0.5, 13.5±0.5, 16.6±0.5, 17.1±0.5, 17.7±0.5, and 19.4±0.5. In some embodiments, Form 1 exhibits an X-ray power diffraction pattern further comprising at least one characteristic XRPD peak selected from diffraction angles (2θ (degrees))=21.9±0.5, 23.1±0.5, 25.1±0.5, 27.0±0.5, 32.3±0.5, and 39.4±0.5.

In some embodiments, Form 1 exhibits an X-ray power diffraction pattern comprising at least two peaks selected from the following diffraction angles (2θ (degrees))= 4.5±0.5, 7.7±0.5, 9.0±0.5, 14.7±0.5, 17.1±0.5, 18.1±0.5, 19.4±0.5, and 22.7±0.5. In some embodiments, Form 1 exhibits an X-ray power diffraction pattern comprising at least three peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5. In some embodiments, Form 1 exhibits an X-ray power diffraction pattern comprising at least four peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5.

Figure 1B:
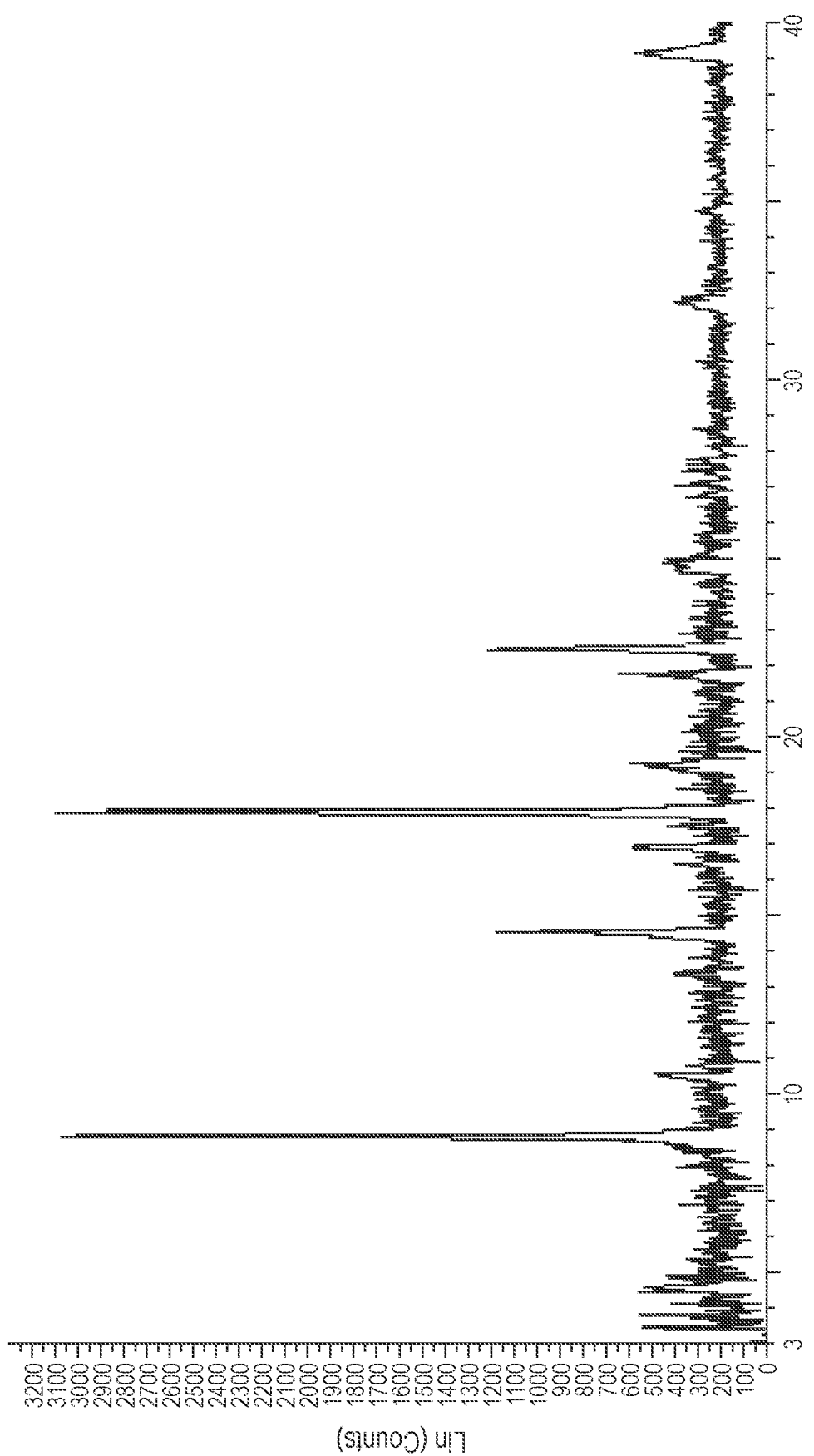
FIG. 1B shows an exemplary XRPD pattern of Form 1.
Figure 1C:
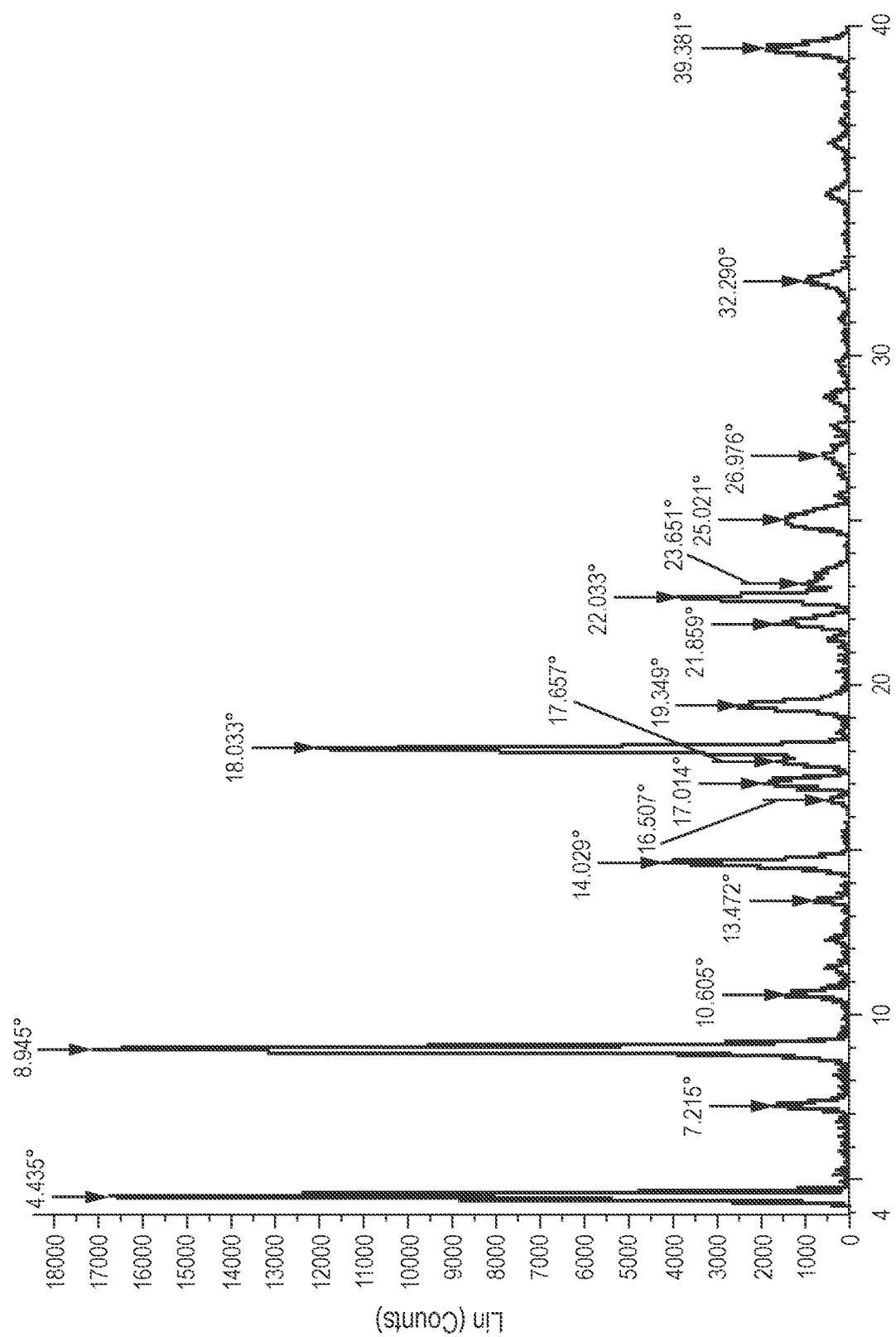
FIG. 1C shows an exemplary XRPD pattern of Form 1.

In some embodiments, Form 1 exhibits an X-ray powder diffraction pattern substantially the same as depicted in FIG. 1C.

In some embodiments, Form 1 exhibits an X-ray power diffraction pattern comprising a peak at the following diffraction angle (2θ (degrees))=8.8±0.2. In some embodiments, Form 1 exhibits an X-ray power diffraction pattern comprising a peak at the following diffraction angle (2θ (degrees))=17.9±0.2. In some embodiments, Form 1 exhibits an X-ray power diffraction pattern comprising a peak at the following diffraction angle (2θ (degrees))=22.5±0.2. In some embodiments, Form 1 exhibits an X-ray power diffraction pattern comprising peaks at the following diffraction angles (2θ (degrees))=17.9±0.2 and 8.8±0.2. In some embodiments, Form 1 exhibits an X-ray power diffraction pattern comprising peaks at the following diffraction angles (2θ (degrees))=17.9±0.2, 8.8±0.2, and 22.5±0.2. In some embodiments, Form 1 exhibits an X-ray power diffraction pattern further comprising at least one characteristic XRPD peak selected from diffraction angles (2θ (degrees))=14.5±0.2, 39.3±0.2, and 10.5±0.2. In some embodiments, Form 1 exhibits an X-ray power diffraction pattern comprising peaks at the following diffraction angles (2θ (degrees))=17.9±0.2, 8.8±0.2, 22.5±0.2, 14.5±0.2, 39.3±0.2, and 10.5±0.2. In some embodiments, Form 1 exhibits an X-ray power diffraction pattern further comprising at least one characteristic XRPD peak selected from diffraction angles (2θ (degrees))=10.5±0.2, 13.3±0.2, 16.9±0.2, 19.2±0.2, 21.3±0.2, 21.8±0.2, 24.9±0.2, 27.1±0.2, 27.8±0.2, and 32.2±0.2. In some embodiments, Form 1 exhibits an X-ray power diffraction pattern comprising peaks at the following diffraction angles (2θ (degrees))=8.8±0.2, 10.5±0.2, 13.3±0.2, 14.5±0.2, 16.9±0.2, 17.9±0.2, 19.2±0.2, 21.3±0.2, 21.8±0.2, 22.5±0.2, 24.9±0.2, 27.1±0.2, 27.8±0.2, 32.2±0.2, and 39.3±0.2.

In some embodiments, Form 1 exhibits an X-ray power diffraction pattern comprising a characteristic XRPD peak at the following diffraction angle (2θ (degrees))=8.8±0.3. In some embodiments, Form 1 exhibits an X-ray power diffraction pattern comprising a characteristic XRPD peak at the following diffraction angle (2θ (degrees))=17.9±0.3. In some embodiments, Form 1 exhibits an X-ray power diffraction pattern comprising a characteristic XRPD peak at the following diffraction angle (2θ (degrees))=22.5±0.3. In some embodiments, Form 1 exhibits an X-ray power diffraction pattern comprising peaks at the following diffraction angles (2θ (degrees))=17.9±0.3 and 8.8±0.3. In some embodiments, Form 1 exhibits an X-ray power diffraction pattern comprising peaks at the following diffraction angles (2θ (degrees))=17.9±0.3, 8.8±0.3, and 22.5±0.3. In some embodiments, Form 1 exhibits an X-ray power diffraction pattern comprising peaks at the following diffraction angles (2θ (degrees))=17.9±0.3, 8.8±0.3, 22.5±0.3, and 14.5±0.3. In some embodiments, Form 1 exhibits an X-ray power diffraction pattern further comprising at least one characteristic XRPD peak selected from diffraction angles (2θ (degrees))=10.5±0.3, 13.3±0.3, 16.9±0.3, and 19.2±0.3. In some embodiments, Form 1 exhibits an X-ray power diffraction pattern further comprising at least one characteristic XRPD peak selected from diffraction angles (2θ (degrees))=10.5±0.3, 13.3±0.3, 16.9±0.3, 19.2±0.3, 21.3±0.3, 21.8±0.3, 24.9±0.3, 27.1±0.3, and 27.8±0.3. In some embodiments, Form 1 exhibits an X-ray power diffraction pattern comprising peaks at the following diffraction angles (2θ (degrees))=17.9±0.3, 8.8±0.3, 22.5±0.3, 14.5±0.3, 10.5±0.3, 13.3±0.3, 16.9±0.3, 19.2±0.3, 21.3±0.3, 21.8±0.3, 24.9±0.3, 27.1±0.3, and 27.8±0.3.

In some embodiments, Form 1 exhibits an X-ray power diffraction pattern comprising peaks at the following diffraction angles (2θ (degrees))=17.9±0.3, 8.8±0.3, and 22.5±0.3. In some embodiments, Form 1 exhibits an X-ray power diffraction pattern further comprising at least one characteristic XRPD peak selected from diffraction angles (2θ (degrees))=14.5±0.3, 39.3±0.3, and 10.5±0.3. In some embodiments, Form 1 exhibits an X-ray power diffraction pattern comprising peaks at the following diffraction angles (2θ (degrees))=17.9±0.3, 8.8±0.3, 22.5±0.3, 14.5±0.3, 39.3±0.3, and 10.5±0.3. In some embodiments, Form 1 exhibits an X-ray power diffraction pattern further comprising at least one characteristic XRPD peak selected from diffraction angles (2θ (degrees))=10.5±0.3, 13.3±0.3, 16.9±0.3, 19.2±0.3, 21.3±0.3, 21.8±0.3, 24.9±0.3, 27.1±0.3, 27.8±0.3, and 32.2±0.3. In some embodiments, Form 1 exhibits an X-ray power diffraction pattern comprising peaks at the following diffraction angles (2θ (degrees))=8.8±0.3, 10.5±0.3, 13.3±0.3, 14.5±0.3, 16.9±0.3, 17.9±0.3, 19.2±0.3, 21.3±0.3, 21.8±0.3, 22.5±0.3, 24.9±0.3, 27.1±0.3, 27.8±0.3, 32.2±0.3, and 39.3±0.3.

In some embodiments, Form 1 exhibits an X-ray power diffraction pattern comprising a characteristic XRPD peak at the following diffraction angle (2θ (degrees))=8.8±0.5. In some embodiments, Form 1 exhibits an X-ray power diffraction pattern comprising a characteristic XRPD peak at the following diffraction angle (2θ (degrees))=17.9±0.5. In some embodiments, Form 1 exhibits an X-ray power diffraction pattern comprising a characteristic XRPD peak at the following diffraction angle (2θ (degrees))=22.5±0.5. In some embodiments, Form 1 exhibits an X-ray power diffraction pattern comprising peaks at the following diffraction angles (2θ (degrees))=17.9±0.5 and 8.8±0.5. In some embodiments, Form 1 exhibits an X-ray power diffraction pattern comprising peaks at the following diffraction angles (2θ (degrees))=17.9±0.5, 8.8±0.5, and 22.5±0.5. In some embodiments, Form 1 exhibits an X-ray power diffraction pattern comprising peaks at the following diffraction angles (2θ (degrees))=17.9±0.5, 8.8±0.5, 22.5±0.5, and 14.5±0.5. In some embodiments, Form 1 exhibits an X-ray power diffraction pattern further comprising at least one characteristic XRPD peak selected from diffraction angles (2θ (degrees))=10.5±0.5, 13.3±0.5, 16.9±0.5, and 19.2±0.5. In some embodiments, Form 1 exhibits an X-ray power diffraction pattern further comprising at least one characteristic XRPD peak selected from diffraction angles (2θ (degrees))=10.5±0.5, 13.3±0.5, 16.9±0.5, 19.2±0.5, 21.3±0.5, 21.8±0.5, 24.9±0.5, 27.1±0.5, and 27.8±0.5. In some embodiments, Form 1 exhibits an X-ray power diffraction pattern comprising peaks at the following diffraction angles (2θ (degrees))=17.9±0.5, 8.8±0.5, 22.5±0.5, 14.5±0.5, 10.5±0.5, 13.3±0.5, 16.9±0.5, 19.2±0.5, 21.3±0.5, 21.8±0.5, 24.9±0.5, 27.1±0.5, and 27.8±0.5.

In some embodiments, Form 1 exhibits an X-ray power diffraction pattern comprising peaks at the following diffraction angles (2θ (degrees))=17.9±0.5, 8.8±0.5, and 22.5±0.5. In some embodiments, Form 1 exhibits an X-ray power diffraction pattern further comprising at least one characteristic XRPD peak selected from diffraction angles (2θ (degrees))=14.5±0.5, 39.3±0.5, and 10.5±0.5. In some embodiments, Form 1 exhibits an X-ray power diffraction pattern comprising peaks at the following diffraction angles (2θ (degrees))=17.9±0.5, 8.8±0.5, 22.5±0.5, 14.5±0.5, 39.3±0.5, and 10.5±0.5. In some embodiments, Form 1 exhibits an X-ray power diffraction pattern further comprising at least one characteristic XRPD peak selected from diffraction angles (2θ (degrees))=10.5±0.5, 13.3±0.5, 16.9±0.5, 19.2±0.5, 21.3±0.5, 21.8±0.5, 24.9±0.5, 27.1±0.5, 27.8±0.5, and 32.2±0.5. In some embodiments, Form 1 exhibits an X-ray power diffraction pattern comprising peaks at the following diffraction angles (2θ (degrees))= 8.8±0.5, 10.5±0.5, 13.3±0.5, 14.5±0.5, 16.9±0.5, 17.9±0.5, 19.2±0.5, 21.3±0.5, 21.8±0.5, 22.5±0.5, 24.9±0.5, 27.1±0.5, 27.8±0.5, 32.2±0.5, and 39.3±0.5.

In some embodiments, Form 1 exhibits an X-ray powder diffraction pattern substantially the same as depicted in FIG. 1B.

Figure 2:
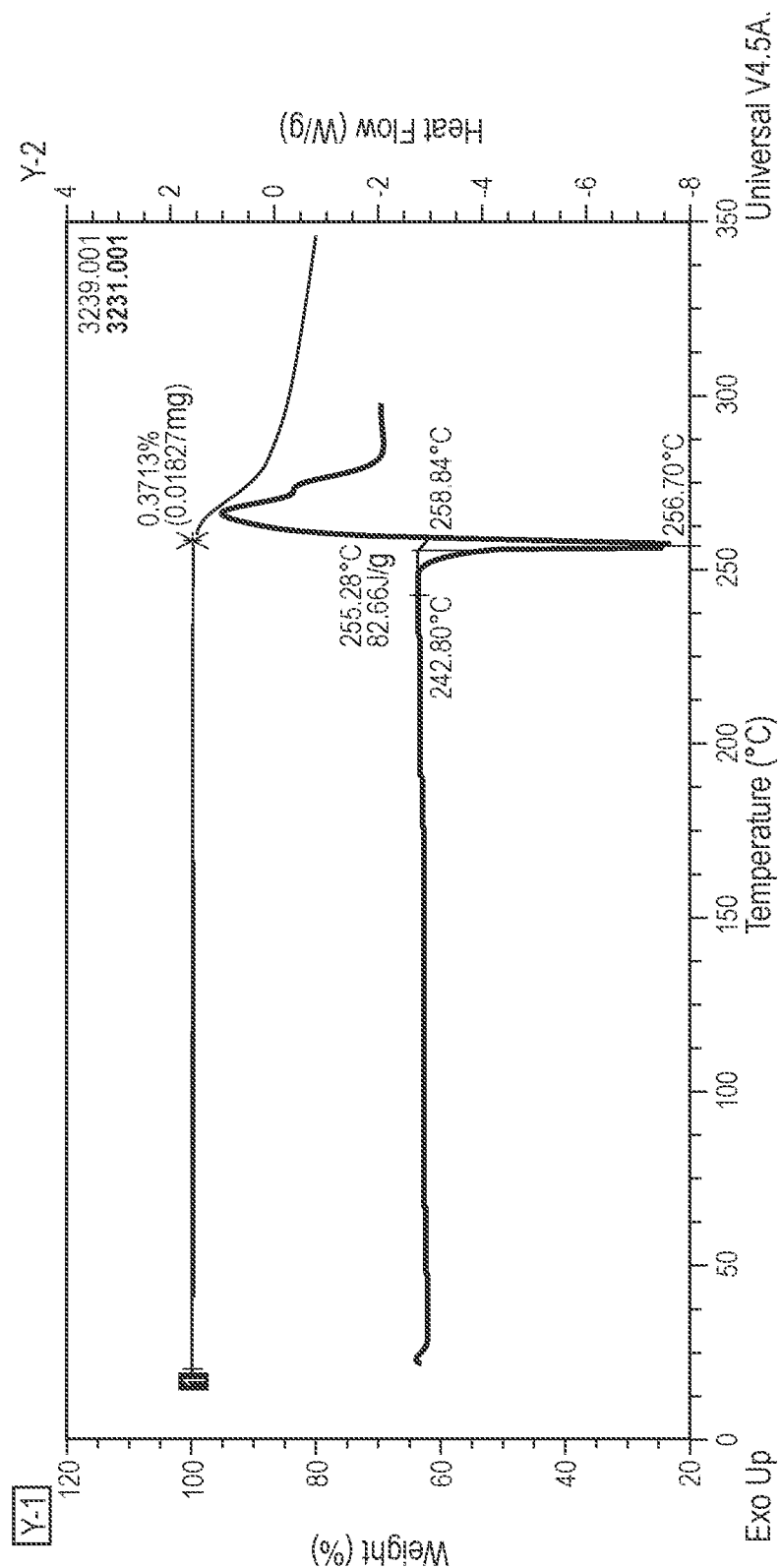
FIG. 2 shows an exemplary DSC and TGA overlay of Form 1.

In some embodiments, Form 1 has a differential scanning calorimetry curve substantially the same as shown in FIG. 2. In some embodiments, Form 1 exhibits an endotherm starting from about 255° C. based on differential scanning calorimetry.

Figure 3:
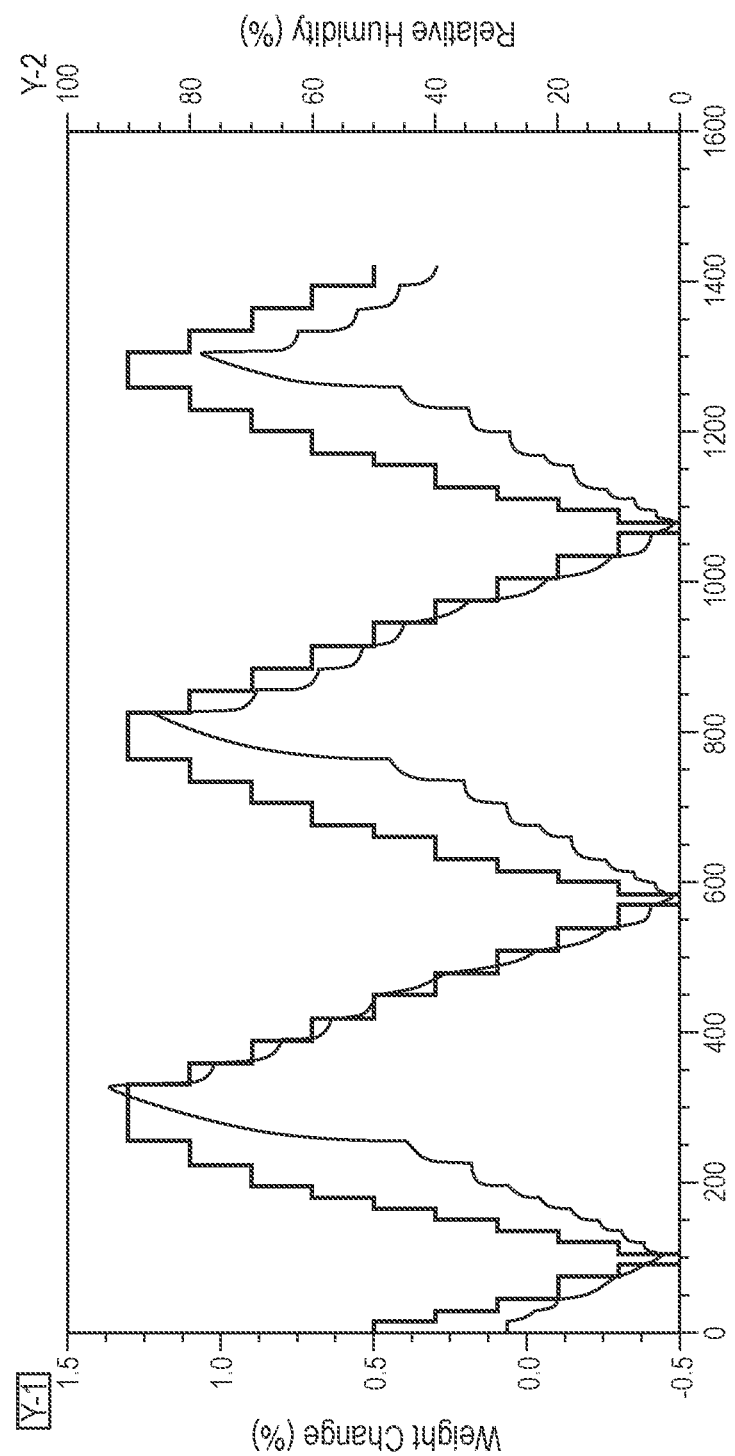
FIG. 3 shows an exemplary DVS pattern of Form 1.

In some embodiments, Form 1 has a dynamic vapor sorption plot substantially the same as shown in FIG. 3.

In some embodiments, Form 1 is an anhydrate.

In some embodiments, Form 1 comprises less than about 3.0% water. In some embodiments, Form 1 comprises less than about 2.0% water. In some embodiments, Form 1 comprises less than about 1.0% water. In some embodiments, Form 1 comprises less than about 0.5% water.

In an aspect, provided herein is crystalline Form 1 of a compound of Formula II:

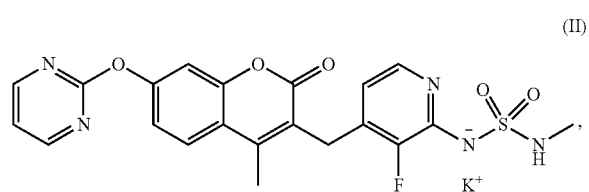 [SMILES: CNS(=O)(=O)[N-]c1nccc(Cc2c(C)c3ccc(Oc4ncccn4)cc3oc2=O)c1F ; [K+]]

(II)

wherein Form 1 is substantially free of an impurity.

In some embodiments, Form 1 comprises less than about 10% area percentage of impurities as determined by HPLC. In some embodiments, Form 1 comprises less than about 9% area percentage of impurities as determined by HPLC. In some embodiments, Form 1 comprises less than about 8% area percentage of impurities as determined by HPLC. In some embodiments, Form 1 comprises less than about 7% area percentage of impurities as determined by HPLC. In some embodiments, Form 1 comprises less than about 6% area percentage of impurities as determined by HPLC. In some embodiments, Form 1 comprises less than about 5% area percentage of impurities as determined by HPLC. In some embodiments, Form 1 comprises less than about 4% area percentage of impurities as determined by HPLC. In some embodiments, Form 1 comprises less than about 3% area percentage of impurities as determined by HPLC. In some embodiments, Form 1 comprises less than about 2% area percentage of impurities as determined by HPLC. In some embodiments, Form 1 comprises less than about 1% area percentage of impurities as determined by HPLC.

In some embodiments, the impurity is Compound B, Compound C, or Compound D, or a combination thereof:

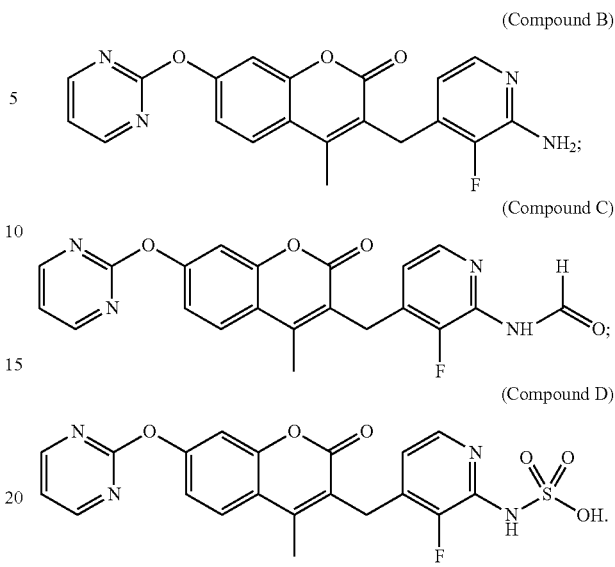

In some embodiments, Form 1 comprises less than about 5.0% of Compound B as determined by HPLC. In some embodiments, Form 1 comprises less than about 4.0% of Compound B as determined by HPLC. In some embodiments, Form 1 comprises less than about 3.0% of Compound B as determined by HPLC. In some embodiments, Form 1 comprises less than about 2.0% of Compound B as determined by HPLC. In some embodiments, Form 1 comprises less than about 1.5% of Compound B as determined by HPLC. In some embodiments, Form 1 comprises less than about 1.0% of Compound B as determined by HPLC. In some embodiments, Form 1 comprises less than about 0.8% of Compound B as determined by HPLC. In some embodiments, Form 1 comprises less than about 0.6% of Compound B as determined by HPLC. In some embodiments, Form 1 comprises less than about 0.5% of Compound B as determined by HPLC. In some embodiments, Form 1 comprises less than about 0.4% of Compound B as determined by HPLC. In some embodiments, Form 1 comprises less than about 0.2% of Compound B as determined by HPLC. In some embodiments, Form 1 comprises less than about 0.1% of Compound B as determined by HPLC.

In some embodiments, Form 1 comprises less than about 5.0% of Compound C as determined by HPLC. In some embodiments, Form 1 comprises less than about 4.0% of Compound C as determined by HPLC. In some embodiments, Form 1 comprises less than about 3.0% of Compound C as determined by HPLC. In some embodiments, Form 1 comprises less than about 2.0% of Compound C as determined by HPLC. In some embodiments, Form 1 comprises less than about 1.5% of Compound C as determined by HPLC. In some embodiments, Form 1 comprises less than about 1.0% of Compound C as determined by HPLC. In some embodiments, Form 1 comprises less than about 0.8% of Compound C as determined by HPLC. In some embodiments, Form 1 comprises less than about 0.6% of Compound C as determined by HPLC. In some embodiments, Form 1 comprises less than about 0.5% of Compound C as determined by HPLC. In some embodiments, Form 1 comprises less than about 0.4% of Compound C as determined by HPLC. In some embodiments, Form 1 comprises less than about of Compound C as determined by HPLC. In some embodiments, Form 1 comprises less than about 0.1% of Compound C as determined by HPLC.

In some embodiments, Form 1 comprises less than about 5.0% of Compound D as determined by HPLC. In some embodiments, Form 1 comprises less than about 4.0% of Compound D as determined by HPLC. In some embodiments, Form 1 comprises less than about 3.0% of Compound D as determined by HPLC. In some embodiments, Form 1 comprises less than about 2.0% of Compound D as determined by HPLC. In some embodiments, Form 1 comprises less than about 1.5% of Compound D as determined by HPLC. In some embodiments, Form 1 comprises less than about 1.0% of Compound D as determined by HPLC. In some embodiments, Form 1 comprises less than about 0.75% of Compound D as determined by HPLC. In some embodiments, Form 1 comprises less than about 0.50% of Compound D as determined by HPLC. In some embodiments, Form 1 comprises less than about 0.25% of Compound D as determined by HPLC. In some embodiments, Form 1 comprises less than about of Compound D as determined by HPLC. In some embodiments, Form 1 comprises less than about 0.15% of Compound D as determined by HPLC. In some embodiments, Form 1 comprises less than about 0.10% of Compound D as determined by HPLC. In some embodiments, Form 1 comprises less than about 0.05% of Compound D as determined by HPLC.

In some embodiments, Form 1 comprises less than about 5.0% water. In some embodiments, Form 1 comprises less than about 4.0% water. In some embodiments, Form 1 comprises less than about 3.0% water. In some embodiments, Form 1 comprises less than about 2.0% water. In some embodiments, Form 1 comprises less than about 1.0% water. In some embodiments, Form 1 comprises less than about 0.5% water.

In some embodiments, Form 1 exhibits an X-ray power diffraction pattern comprising a characteristic XRPD peak at the following diffraction angle ($2\theta$ (degrees))=9.0±0.2. In some embodiments, Form 1 exhibits an X-ray power diffraction pattern comprising a characteristic XRPD peak at the following diffraction angle ($2\theta$ (degrees))=4.5±0.2. In some embodiments, Form 1 exhibits an X-ray power diffraction pattern comprising a characteristic XRPD peak at the following diffraction angle ($2\theta$ (degrees))=14.7±0.2. In some embodiments, Form 1 exhibits an X-ray power diffraction pattern comprising a characteristic XRPD peak at the following diffraction angle ($2\theta$ (degrees))=18.1±0.2. In some embodiments, Form 1 exhibits an X-ray power diffraction pattern comprising a characteristic XRPD peak at the following diffraction angle ($2\theta$ (degrees))=22.7±0.2. In some embodiments, Form 1 exhibits an X-ray power diffraction pattern comprising peaks at the following diffraction angles ($2\theta$ (degrees))=4.5±0.2 and 9.0±0.2. In some embodiments, Form 1 exhibits an X-ray power diffraction pattern comprising peaks at the following diffraction angles ($2\theta$ (degrees))=4.5±0.2, 9.0±0.2, and 14.7±0.2. In some embodiments, Form 1 exhibits an X-ray power diffraction pattern comprising peaks at the following diffraction angles ($2\theta$ (degrees))=4.5±0.2, 9.0±0.2, 14.7±0.2, and 18.1±0.2. In some embodiments, Form 1 exhibits an X-ray power diffraction pattern comprising peaks at the following diffraction angles ($2\theta$ (degrees))=4.5±0.2, 9.0±0.2, 14.7±0.2, 18.1±0.2. and 22.7±0.2. In some embodiments, Form 1 exhibits an X-ray power diffraction pattern comprising peaks at the following diffraction angles ($2\theta$ (degrees))=9.0±0.2 and 18.1±0.2. In some embodiments, Form 1 exhibits an X-ray power diffraction pattern comprising peaks at the following diffraction angles ($2\theta$ (degrees))=4.5±0.2 and 18.1±0.2. In some embodiments, Form 1 exhibits an X-ray power diffraction pattern comprising at least two peaks selected from the following diffraction angles ($2\theta$ (degrees))=4.5±0.2, 9.0±0.2, 14.7±0.2, 18.1±0.2. and 22.7±0.2. In some embodiments, Form 1 exhibits an X-ray power diffraction pattern comprising at least three peaks selected from the following diffraction angles ($2\theta$ (degrees))=4.5±0.2, 9.0±0.2, 14.7±0.2, 18.1±0.2, and 22.7±0.2. In some embodiments, Form 1 exhibits an X-ray power diffraction pattern comprising at least four peaks selected from the following diffraction angles ($2\theta$ (degrees))=4.5±0.2, 9.0±0.2, 14.7±0.2, 18.1±0.2, and 22.7±0.2.

In some embodiments, Form 1 exhibits an X-ray power diffraction pattern further comprising at least one characteristic XRPD peak selected from diffraction angles ($2\theta$ (degrees))=7.3±0.2, 10.7±0.2, 13.5±0.2, 16.6±0.2, 17.1±0.2, 17.7±0.2, and 19.4±0.2. In some embodiments, Form 1 exhibits an X-ray power diffraction pattern further comprising at least one characteristic XRPD peak selected from diffraction angles ($2\theta$ (degrees))=21.9±0.2, 23.1±0.2, 25.1±0.2, 27.0±0.2, 32.3±0.2, and 39.4±0.2.

In some embodiments, Form 1 exhibits an X-ray power diffraction pattern comprising at least two peaks selected from the following diffraction angles ($2\theta$ (degrees))=4.5±0.2, 7.7±0.2, 9.0±0.2, 14.7±0.2, 17.1±0.2, 18.1±0.2, 19.4±0.2, and 22.7±0.2. In some embodiments, Form 1 exhibits an X-ray power diffraction pattern comprising at least three peaks selected from the following diffraction angles ($2\theta$ (degrees))=4.5±0.2, 7.7±0.2, 9.0±0.2, 14.7±0.2, 17.1±0.2, 18.1±0.2, 19.4±0.2, and 22.7±0.2. In some embodiments, Form 1 exhibits an X-ray power diffraction pattern comprising at least four peaks selected from the following diffraction angles ($2\theta$ (degrees))=4.5±0.2, 7.7±0.2, 9.0±0.2, 14.7±0.2, 17.1±0.2, 18.1±0.2, 19.4±0.2, and 22.7±0.2.

In some embodiments, Form 1 exhibits an X-ray power diffraction pattern comprising a characteristic XRPD peak at the following diffraction angle ($2\theta$ (degrees))=9.0±0.3. In some embodiments, Form 1 exhibits an X-ray power diffraction pattern comprising a characteristic XRPD peak at the following diffraction angle ($2\theta$ (degrees))=4.5±0.3. In some embodiments, Form 1 exhibits an X-ray power diffraction pattern comprising a characteristic XRPD peak at the following diffraction angle ($2\theta$ (degrees))=14.7±0.3. In some embodiments, Form 1 exhibits an X-ray power diffraction pattern comprising a characteristic XRPD peak at the following diffraction angle ($2\theta$ (degrees))=18.1±0.3. In some embodiments, Form 1 exhibits an X-ray power diffraction pattern comprising a characteristic XRPD peak at the following diffraction angle ($2\theta$ (degrees))=22.7±0.3. In some embodiments, Form 1 exhibits an X-ray power diffraction pattern comprising peaks at the following diffraction angles ($2\theta$ (degrees))=4.5±0.3 and 9.0±0.3. In some embodiments, Form 1 exhibits an X-ray power diffraction pattern comprising peaks at the following diffraction angles ($2\theta$ (degrees))=4.5±0.3, 9.0±0.3, and 14.7±0.3. In some embodiments, Form 1 exhibits an X-ray power diffraction pattern comprising peaks at the following diffraction angles ($2\theta$ (degrees))=4.5±0.3, 9.0±0.3, 14.7±0.3, and 18.1±0.3. In some embodiments, Form 1 exhibits an X-ray power diffraction pattern comprising peaks at the following diffraction angles ($2\theta$ (degrees))=4.5±0.3, 9.0±0.3, 14.7±0.3, 18.1±0.3. and 22.7±0.3. In some embodiments, Form 1 exhibits an X-ray power diffraction pattern comprising peaks at the following diffraction angles ($2\theta$ (degrees))=9.0±0.3 and 18.1±0.3. In some embodiments, Form 1 exhibits an X-ray power diffraction pattern comprising peaks at the following diffraction angles (2θ (degrees))=4.5±0.3 and 18.1±0.3. In some embodiments, Form 1 exhibits an X-ray power diffraction pattern comprising at least two peaks selected from the following diffraction angles (2θ (degrees))=4.5±0.3, 9.0±0.3, 14.7±0.3, 18.1±0.3, and 22.7±0.3. In some embodiments, Form 1 exhibits an X-ray power diffraction pattern comprising at least three peaks selected from the following diffraction angles (2θ (degrees))=4.5±0.3, 9.0±0.3, 14.7±0.3, 18.1±0.3, and 22.7±0.3. In some embodiments, Form 1 exhibits an X-ray power diffraction pattern comprising at least four peaks selected from the following diffraction angles (2θ (degrees))=4.5±0.3, 9.0±0.3, 14.7±0.3, 18.1±0.3, and 22.7±0.3.

In some embodiments, Form 1 exhibits an X-ray power diffraction pattern further comprising at least one characteristic XRPD peak selected from diffraction angles (2θ (degrees))=7.3±0.3, 10.7±0.3, 13.5±0.3, 16.6±0.3, 17.1±0.3, 17.7±0.3, and 19.4±0.3. In some embodiments, Form 1 exhibits an X-ray power diffraction pattern further comprising at least one characteristic XRPD peak selected from diffraction angles (2θ (degrees))=21.9±0.3, 23.1±0.3, 25.1±0.3, 27.0±0.3, 32.3±0.3, and 39.4±0.3.

In some embodiments, Form 1 exhibits an X-ray power diffraction pattern comprising at least two peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3. In some embodiments, Form 1 exhibits an X-ray power diffraction pattern comprising at least three peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3. In some embodiments, Form 1 exhibits an X-ray power diffraction pattern comprising at least four peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3.

In some embodiments, Form 1 exhibits an X-ray power diffraction pattern comprising a characteristic XRPD peak at the following diffraction angle (2θ (degrees))=9.0±0.5. In some embodiments, Form 1 exhibits an X-ray power diffraction pattern comprising a characteristic XRPD peak at the following diffraction angle (2θ (degrees))=4.5±0.5. In some embodiments, Form 1 exhibits an X-ray power diffraction pattern comprising a characteristic XRPD peak at the following diffraction angle (2θ (degrees))=14.7±0.5. In some embodiments, Form 1 exhibits an X-ray power diffraction pattern comprising a characteristic XRPD peak at the following diffraction angle (2θ (degrees))=18.1±0.5. In some embodiments, Form 1 exhibits an X-ray power diffraction pattern comprising a characteristic XRPD peak at the following diffraction angle (2θ (degrees))=22.7±0.5. In some embodiments, Form 1 exhibits an X-ray power diffraction pattern comprising peaks at the following diffraction angles (2θ (degrees))=4.5±0.5 and 9.0±0.5. In some embodiments, Form 1 exhibits an X-ray power diffraction pattern comprising peaks at the following diffraction angles (2θ (degrees))=4.5±0.5, 9.0±0.5, and 14.7±0.5. In some embodiments, Form 1 exhibits an X-ray power diffraction pattern comprising peaks at the following diffraction angles (2θ (degrees))=4.5±0.5, 9.0±0.5, 14.7±0.5, and 18.1±0.5. In some embodiments, Form 1 exhibits an X-ray power diffraction pattern comprising peaks at the following diffraction angles (2θ (degrees))=4.5±0.5, 9.0±0.5, 14.7±0.5, 18.1±0.5. and 22.7±0.5. In some embodiments, Form 1 exhibits an X-ray power diffraction pattern comprising peaks at the following diffraction angles (2θ (degrees))=9.0±0.5 and 18.1±0.5. In some embodiments, Form 1 exhibits an X-ray power diffraction pattern comprising peaks at the following diffraction angles (2θ (degrees))=4.5±0.5 and 18.1±0.5. In some embodiments, Form 1 exhibits an X-ray power diffraction pattern comprising at least two peaks selected from the following diffraction angles (2θ (degrees))=4.5±0.5, 9.0±0.5, 14.7±0.5, 18.1±0.5. and 22.7±0.5. In some embodiments, Form 1 exhibits an X-ray power diffraction pattern comprising at least three peaks selected from the following diffraction angles (2θ (degrees))=4.5±0.5, 9.0±0.5, 14.7±0.5, 18.1±0.5, and 22.7±0.5. In some embodiments, Form 1 exhibits an X-ray power diffraction pattern comprising at least four peaks selected from the following diffraction angles (2θ (degrees))=4.5±0.5, 9.0±0.5, 14.7±0.5, 18.1±0.5, and 22.7±0.5.

In some embodiments, Form 1 exhibits an X-ray power diffraction pattern further comprising at least one characteristic XRPD peak selected from diffraction angles (2θ (degrees))=7.3±0.5, 10.7±0.5, 13.5±0.5, 16.6±0.5, 17.1±0.5, 17.7±0.5, and 19.4±0.5. In some embodiments, Form 1 exhibits an X-ray power diffraction pattern further comprising at least one characteristic XRPD peak selected from diffraction angles (2θ (degrees))=21.9±0.5, 23.1±0.5, 25.1±0.5, 27.0±0.5, 32.3±0.5, and 39.4±0.5.

In some embodiments, Form 1 exhibits an X-ray power diffraction pattern comprising at least two peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5. In some embodiments, Form 1 exhibits an X-ray power diffraction pattern comprising at least three peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5. In some embodiments, Form 1 exhibits an X-ray power diffraction pattern comprising at least four peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5.

In some embodiments, Form 1 exhibits an X-ray powder diffraction pattern substantially the same as depicted in FIG. 1C.

In some embodiments, Form 1 exhibits an X-ray power diffraction pattern comprising a peak at the following diffraction angle (2θ (degrees))=8.8±0.2. In some embodiments, Form 1 exhibits an X-ray power diffraction pattern comprising a peak at the following diffraction angle (2θ (degrees))=17.9±0.2. In some embodiments, Form 1 exhibits an X-ray power diffraction pattern comprising a peak at the following diffraction angle (2θ (degrees))=22.5±0.2. In some embodiments, Form 1 exhibits an X-ray power diffraction pattern comprising peaks at the following diffraction angles (2θ (degrees))=17.9±0.2 and 8.8±0.2. In some embodiments, Form 1 exhibits an X-ray power diffraction pattern comprising peaks at the following diffraction angles (2θ (degrees))=17.9±0.2, 8.8±0.2, and 22.5±0.2. In some embodiments, Form 1 exhibits an X-ray power diffraction pattern further comprising at least one characteristic XRPD peak selected from diffraction angles (2θ (degrees))=14.5±0.2, 39.3±0.2, and 10.5±0.2. In some embodiments, Form 1 exhibits an X-ray power diffraction pattern comprising peaks at the following diffraction angles (2θ (degrees))=17.9±0.2, 8.8±0.2, 22.5±0.2, 14.5±0.2, 39.3±0.2, and 10.5±0.2. In some embodiments, Form 1 exhibits an X-ray power diffraction pattern further comprising at least one characteristic XRPD peak selected from diffraction angles (2θ (degrees))=10.5±0.2, 13.3±0.2, 16.9±0.2, 19.2±0.2, 21.3±0.2, 21.8±0.2, 24.9±0.2, 27.1±0.2, 27.8±0.2, and 32.2±0.2. In some embodiments, Form 1 exhibits an X-ray power diffraction pattern comprising peaks at the following diffraction angles (2θ (degrees))=8.8±0.2, 10.5±0.2, 13.3±0.2, 14.5±0.2, 16.9±0.2, 17.9±0.2, 19.2±0.2, 21.3±0.2, 21.8±0.2, 22.5±0.2, 24.9±0.2, 27.1±0.2, 27.8±0.2, 32.2±0.2, and 39.3±0.2.

In some embodiments, Form 1 exhibits an X-ray power diffraction pattern comprising a characteristic XRPD peak at the following diffraction angle (2θ (degrees))=8.8±0.3. In some embodiments, Form 1 exhibits an X-ray power diffraction pattern comprising a characteristic XRPD peak at the following diffraction angle (2θ (degrees))=17.9±0.3. In some embodiments, Form 1 exhibits an X-ray power diffraction pattern comprising a characteristic XRPD peak at the following diffraction angle (2θ (degrees))=22.5±0.3. In some embodiments, Form 1 exhibits an X-ray power diffraction pattern comprising peaks at the following diffraction angles (2θ (degrees))=17.9±0.3 and 8.8±0.3. In some embodiments, Form 1 exhibits an X-ray power diffraction pattern comprising peaks at the following diffraction angles (2θ (degrees))=17.9±0.3, 8.8±0.3, and 22.5±0.3. In some embodiments, Form 1 exhibits an X-ray power diffraction pattern comprising peaks at the following diffraction angles (2θ (degrees))=17.9±0.3, 8.8±0.3, 22.5±0.3, and 14.5±0.3. In some embodiments, Form 1 exhibits an X-ray power diffraction pattern further comprising at least one characteristic XRPD peak selected from diffraction angles (2θ (degrees))=10.5±0.3, 13.3±0.3, 16.9±0.3, and 19.2±0.3. In some embodiments, Form 1 exhibits an X-ray power diffraction pattern further comprising at least one characteristic XRPD peak selected from diffraction angles (2θ (degrees))=10.5±0.3, 13.3±0.3, 16.9±0.3, 19.2±0.3, 21.3±0.3, 21.8±0.3, 24.9±0.3, 27.1±0.3, and 27.8±0.3. In some embodiments, Form 1 exhibits an X-ray power diffraction pattern comprising peaks at the following diffraction angles (2θ (degrees))=17.9±0.3, 8.8±0.3, 22.5±0.3, 14.5±0.3, 10.5±0.3, 13.3±0.3, 16.9±0.3, 19.2±0.3, 21.3±0.3, 21.8±0.3, 24.9±0.3, 27.1±0.3, and 27.8±0.3.

In some embodiments, Form 1 exhibits an X-ray power diffraction pattern comprising peaks at the following diffraction angles (2θ (degrees))=17.9±0.3, 8.8±0.3, and 22.5±0.3. In some embodiments, Form 1 exhibits an X-ray power diffraction pattern further comprising at least one characteristic XRPD peak selected from diffraction angles (2θ (degrees))=14.5±0.3, 39.3±0.3, and 10.5±0.3. In some embodiments, Form 1 exhibits an X-ray power diffraction pattern comprising peaks at the following diffraction angles (2θ (degrees))=17.9±0.3, 8.8±0.3, 22.5±0.3, 14.5±0.3, 39.3±0.3, and 10.5±0.3. In some embodiments, Form 1 exhibits an X-ray power diffraction pattern further comprising at least one characteristic XRPD peak selected from diffraction angles (2θ (degrees))=10.5±0.3, 13.3±0.3, 16.9±0.3, 19.2±0.3, 21.3±0.3, 21.8±0.3, 24.9±0.3, 27.1±0.3, 27.8±0.3, and 32.2±0.3. In some embodiments, Form 1 exhibits an X-ray power diffraction pattern comprising peaks at the following diffraction angles (2θ (degrees))=8.8±0.3, 10.5±0.3, 13.3±0.3, 14.5±0.3, 16.9±0.3, 17.9±0.3, 19.2±0.3, 21.3±0.3, 21.8±0.3, 22.5±0.3, 24.9±0.3, 27.1±0.3, 27.8±0.3, 32.2±0.3, and 39.3±0.3.

In some embodiments, Form 1 exhibits an X-ray power diffraction pattern comprising a characteristic XRPD peak at the following diffraction angle (2θ (degrees))=8.8±0.5. In some embodiments, Form 1 exhibits an X-ray power diffraction pattern comprising a characteristic XRPD peak at the following diffraction angle (2θ (degrees))=17.9±0.5. In some embodiments, Form 1 exhibits an X-ray power diffraction pattern comprising a characteristic XRPD peak at the following diffraction angle (2θ (degrees))=22.5±0.5. In some embodiments, Form 1 exhibits an X-ray power diffraction pattern comprising peaks at the following diffraction angles (2θ (degrees))=17.9±0.5 and 8.8±0.5. In some embodiments, Form 1 exhibits an X-ray power diffraction pattern comprising peaks at the following diffraction angles (2θ (degrees))=17.9±0.5, 8.8±0.5, and 22.5±0.5. In some embodiments, Form 1 exhibits an X-ray power diffraction pattern comprising peaks at the following diffraction angles (2θ (degrees))=17.9±0.5, 8.8±0.5, 22.5±0.5, and 14.5±0.5. In some embodiments, Form 1 exhibits an X-ray power diffraction pattern further comprising at least one characteristic XRPD peak selected from diffraction angles (2θ (degrees))=10.5±0.5, 13.3±0.5, 16.9±0.5, and 19.2±0.5. In some embodiments, Form 1 exhibits an X-ray power diffraction pattern further comprising at least one characteristic XRPD peak selected from diffraction angles (2θ (degrees))=10.5±0.5, 13.3±0.5, 16.9±0.5, 19.2±0.5, 21.3±0.5, 21.8±0.5, 24.9±0.5, 27.1±0.5, and 27.8±0.5. In some embodiments, Form 1 exhibits an X-ray power diffraction pattern comprising peaks at the following diffraction angles (2θ (degrees))=17.9±0.5, 8.8±0.5, 22.5±0.5, 14.5±0.5, 10.5±0.5, 13.3±0.5, 16.9±0.5, 19.2±0.5, 21.3±0.5, 21.8±0.5, 24.9±0.5, 27.1±0.5, and 27.8±0.5.

In some embodiments, Form 1 exhibits an X-ray power diffraction pattern comprising peaks at the following diffraction angles (2θ (degrees))=17.9±0.5, 8.8±0.5, and 22.5±0.5. In some embodiments, Form 1 exhibits an X-ray power diffraction pattern further comprising at least one characteristic XRPD peak selected from diffraction angles (2θ (degrees))=14.5±0.5, 39.3±0.5, and 10.5±0.5. In some embodiments, Form 1 exhibits an X-ray power diffraction pattern comprising peaks at the following diffraction angles (2θ (degrees))=17.9±0.5, 8.8±0.5, 22.5±0.5, 14.5±0.5, 39.3±0.5, and 10.5±0.5. In some embodiments, Form 1 exhibits an X-ray power diffraction pattern further comprising at least one characteristic XRPD peak selected from diffraction angles (2θ (degrees))=10.5±0.5, 13.3±0.5, 16.9±0.5, 19.2±0.5, 21.3±0.5, 21.8±0.5, 24.9±0.5, 27.1±0.5, 27.8±0.5, and 32.2±0.5. In some embodiments, Form 1 exhibits an X-ray power diffraction pattern comprising peaks at the following diffraction angles (2θ (degrees))=8.8±0.5, 10.5±0.5, 13.3±0.5, 14.5±0.5, 16.9±0.5, 17.9±0.5, 19.2±0.5, 21.3±0.5, 21.8±0.5, 22.5±0.5, 24.9±0.5, 27.1±0.5, 27.8±0.5, 32.2±0.5, and 39.3±0.5.

In some embodiments, Form 1 exhibits an X-ray powder diffraction pattern substantially the same as depicted in FIG. 1B.

In some embodiments, Form 1 has a differential scanning calorimetry curve substantially the same as shown in FIG. 2. In some embodiments, Form 1 exhibits an endotherm starting from about 255° C. based on differential scanning calorimetry.

In some embodiments, Form 1 has a dynamic vapor sorption plot substantially the same as shown in FIG. 3.

In some embodiments, Form 1 is an anhydrate.

In an aspect, provided herein is crystalline Form 1 of a compound of Formula II:

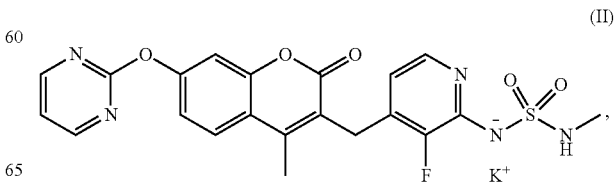

wherein Form 1 exhibits an X-ray power diffraction pattern comprising a characteristic XRPD peak at the following diffraction angle (2θ (degrees))=9.0±0.2. In some embodiments, Form 1 exhibits an X-ray power diffraction pattern further comprising a characteristic XRPD peak at the following diffraction angle (2θ (degrees))=4.5±0.2. In some embodiments, Form 1 exhibits an X-ray power diffraction pattern further comprising a characteristic XRPD peak at the following diffraction angle (2θ (degrees))=14.7±0.2. In some embodiments, Form 1 exhibits an X-ray power diffraction pattern further comprising a characteristic XRPD peak at the following diffraction angle (2θ (degrees))=18.1±0.2. In some embodiments, Form 1 exhibits an X-ray power diffraction pattern further comprising a characteristic XRPD peak at the following diffraction angle (2θ (degrees))=22.7±0.2. In some embodiments, Form 1 exhibits an X-ray power diffraction pattern comprising peaks at the following diffraction angles (2θ (degrees))=4.5±0.2 and 9.0±0.2. In some embodiments, Form 1 exhibits an X-ray power diffraction pattern comprising peaks at the following diffraction angles (2θ (degrees))=4.5±0.2, 9.0±0.2, and 14.7±0.2. In some embodiments, Form 1 exhibits an X-ray power diffraction pattern comprising peaks at the following diffraction angles (2θ (degrees))=4.5±0.2, 9.0±0.2, 14.7±0.2, and 18.1±0.2. In some embodiments, Form 1 exhibits an X-ray power diffraction pattern comprising peaks at the following diffraction angles (2θ (degrees))=4.5±0.2, 9.0±0.2, 14.7±0.2, 18.1±0.2. and 22.7±0.2. In some embodiments, Form 1 exhibits an X-ray power diffraction pattern comprising peaks at the following diffraction angles (2θ (degrees))=9.0±0.2 and 18.1±0.2. In some embodiments, Form 1 exhibits an X-ray power diffraction pattern comprising peaks at the following diffraction angles (2θ (degrees))=4.5±0.2 and 18.1±0.2. In some embodiments, Form 1 exhibits an X-ray power diffraction pattern comprising at least two peaks selected from the following diffraction angles (2θ (degrees))=4.5±0.2, 9.0±0.2, 14.7±0.2, 18.1±0.2. and 22.7±0.2. In some embodiments, Form 1 exhibits an X-ray power diffraction pattern comprising at least three peaks selected from the following diffraction angles (2θ (degrees))=4.5±0.2, 9.0±0.2, 14.7±0.2, 18.1±0.2, and 22.7±0.2. In some embodiments, Form 1 exhibits an X-ray power diffraction pattern comprising at least four peaks selected from the following diffraction angles (2θ (degrees))=4.5±0.2, 9.0±0.2, 14.7±0.2, 18.1±0.2, and 22.7±0.2.

In some embodiments, Form 1 exhibits an X-ray power diffraction pattern further comprising at least one characteristic XRPD peak selected from diffraction angles (2θ (degrees))=7.3±0.2, 10.7±0.2, 13.5±0.2, 16.6±0.2, 17.1±0.2, 17.7±0.2, and 19.4±0.2. In some embodiments, Form 1 exhibits an X-ray power diffraction pattern further comprising at least one characteristic XRPD peak selected from diffraction angles (2θ (degrees))=21.9±0.2, 23.1±0.2, 25.1±0.2, 27.0±0.2, 32.3±0.2, and 39.4±0.2.

In some embodiments, Form 1 exhibits an X-ray power diffraction pattern comprising at least two peaks selected from the following diffraction angles (2θ (degrees))=4.5±0.2, 7.7±0.2, 9.0±0.2, 14.7±0.2, 17.1±0.2, 18.1±0.2, 19.4±0.2, and 22.7±0.2. In some embodiments, Form 1 exhibits an X-ray power diffraction pattern comprising at least three peaks selected from the following diffraction angles (2θ (degrees))=4.5±0.2, 7.7±0.2, 9.0±0.2, 14.7±0.2, 17.1±0.2, 18.1±0.2, 19.4±0.2, and 22.7±0.2. In some embodiments, Form 1 exhibits an X-ray power diffraction pattern comprising at least four peaks selected from the following diffraction angles (2θ (degrees))=4.5±0.2, 7.7±0.2, 9.0±0.2, 14.7±0.2, 17.1±0.2, 18.1±0.2, 19.4±0.2, and 22.7±0.2.

In some embodiments, Form 1 exhibits an X-ray powder diffraction pattern substantially the same as depicted in FIG. 1C.

In some embodiments, Form 1 has a differential scanning calorimetry curve substantially the same as shown in FIG. 2. In some embodiments, Form 1 exhibits an endotherm starting from about 255° C. based on differential scanning calorimetry.

In some embodiments, Form 1 has a dynamic vapor sorption plot substantially the same as shown in FIG. 3.

In some embodiments, Form 1 is an anhydrate.

In an aspect, provided herein is crystalline Form 1 of a compound of Formula II:

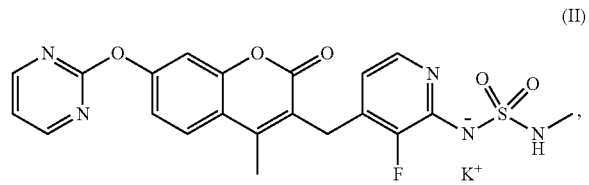 [SMILES: CNS(=O)(=O)[N-]c1nccc(Cc2c(C)c3ccc(Oc4ncccn4)cc3oc2=O)c1F ; [K+]]

(II)

wherein Form 1 exhibits an X-ray power diffraction pattern comprising a characteristic XRPD peak at the following diffraction angle (2θ (degrees))=9.0±0.3. In some embodiments, Form 1 exhibits an X-ray power diffraction pattern further comprising a characteristic XRPD peak at the following diffraction angle (2θ (degrees))=4.5±0.3. In some embodiments, Form 1 exhibits an X-ray power diffraction pattern further comprising a characteristic XRPD peak at the following diffraction angle (2θ (degrees))=14.7±0.3. In some embodiments, Form 1 exhibits an X-ray power diffraction pattern further comprising a characteristic XRPD peak at the following diffraction angle (2θ (degrees))=18.1±0.3. In some embodiments, Form 1 exhibits an X-ray power diffraction pattern further comprising a characteristic XRPD peak at the following diffraction angle (2θ (degrees))=22.7±0.3. In some embodiments, Form 1 exhibits an X-ray power diffraction pattern comprising peaks at the following diffraction angles (2θ (degrees))=4.5±0.3 and 9.0±0.3. In some embodiments, Form 1 exhibits an X-ray power diffraction pattern comprising peaks at the following diffraction angles (2θ (degrees))=4.5±0.3, 9.0±0.3, and 14.7±0.3. In some embodiments, Form 1 exhibits an X-ray power diffraction pattern comprising peaks at the following diffraction angles (2θ (degrees))=4.5±0.3, 9.0±0.3, 14.7±0.3, and 18.1±0.3. In some embodiments, Form 1 exhibits an X-ray power diffraction pattern comprising peaks at the following diffraction angles (2θ (degrees))=4.5±0.3, 9.0±0.3, 14.7±0.3, 18.1±0.3. and 22.7±0.3. In some embodiments, Form 1 exhibits an X-ray power diffraction pattern comprising peaks at the following diffraction angles (2θ (degrees))=9.0±0.3 and 18.1±0.3. In some embodiments, Form 1 exhibits an X-ray power diffraction pattern comprising peaks at the following diffraction angles (2θ (degrees))=4.5±0.3 and 18.1±0.3. In some embodiments, Form 1 exhibits an X-ray power diffraction pattern comprising at least two peaks selected from the following diffraction angles (2θ (degrees))=4.5±0.3, 9.0±0.3, 14.7±0.3, 18.1±0.3. and 22.7±0.3. In some embodiments, Form 1 exhibits an X-ray power diffraction pattern comprising at least three peaks selected from the following diffraction angles (2θ (degrees))=4.5±0.3, 9.0±0.3, 14.7±0.3, 18.1±0.3, and 22.7±0.3. In some embodiments, Form 1 exhibits an X-ray power diffraction pattern comprising at least four peaks selected from the following diffraction angles (2θ (degrees))=4.5±0.3, 9.0±0.3, 14.7±0.3, 18.1±0.3, and 22.7±0.3.

In some embodiments, Form 1 exhibits an X-ray power diffraction pattern further comprising at least one characteristic XRPD peak selected from diffraction angles (2θ (degrees))=7.3±0.3, 10.7±0.3, 13.5±0.3, 16.6±0.3, 17.1±0.3, 17.7±0.3, and 19.4±0.3. In some embodiments, Form 1 exhibits an X-ray power diffraction pattern further comprising at least one characteristic XRPD peak selected from diffraction angles (2θ (degrees))=21.9±0.3, 23.1±0.3, 25.1±0.3, 27.0±0.3, 32.3±0.3, and 39.4±0.3.

In some embodiments, Form 1 exhibits an X-ray power diffraction pattern comprising at least two peaks selected from the following diffraction angles (2θ (degrees))= 4.5±0.3, 7.7±0.3, 9.0±0.3, 14.7±0.3, 17.1±0.3, 18.1±0.3, 19.4±0.3, and 22.7±0.3. In some embodiments, Form 1 exhibits an X-ray power diffraction pattern comprising at least three peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3. In some embodiments, Form 1 exhibits an X-ray power diffraction pattern comprising at least four peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3.

In some embodiments, Form 1 exhibits an X-ray powder diffraction pattern substantially the same as depicted in FIG. 1C.

In some embodiments, Form 1 has a differential scanning calorimetry curve substantially the same as shown in FIG. 2. In some embodiments, Form 1 exhibits an endotherm starting from about 255° C. based on differential scanning calorimetry.

In some embodiments, Form 1 has a dynamic vapor sorption plot substantially the same as shown in FIG. 3.

In some embodiments, Form 1 is an anhydrate.

In an aspect, provided herein is crystalline Form 1 of a compound of Formula II:

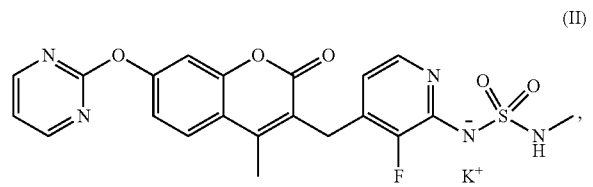 [SMILES: CNS(=O)(=O)[N-]c1nccc(Cc2c(C)c3ccc(Oc4ncccn4)cc3oc2=O)c1F ; [K+]]

(II)

wherein Form 1 exhibits an X-ray power diffraction pattern comprising a characteristic XRPD peak at the following diffraction angle (2θ (degrees))=9.0±0.5. In some embodiments, Form 1 exhibits an X-ray power diffraction pattern further comprising a characteristic XRPD peak at the following diffraction angle (2θ (degrees))=4.5±0.5. In some embodiments, Form 1 exhibits an X-ray power diffraction pattern further comprising a characteristic XRPD peak at the following diffraction angle (2θ (degrees))=14.7±0.5. In some embodiments, Form 1 exhibits an X-ray power diffraction pattern further comprising a characteristic XRPD peak at the following diffraction angle (2θ (degrees))= 18.1±0.5. In some embodiments, Form 1 exhibits an X-ray power diffraction pattern further comprising a characteristic XRPD peak at the following diffraction angle (2θ (degrees))=22.7±0.5. In some embodiments, Form 1 exhibits an X-ray power diffraction pattern comprising peaks at the following diffraction angles (2θ (degrees))=4.5±0.5 and 9.0±0.5. In some embodiments, Form 1 exhibits an X-ray power diffraction pattern comprising peaks at the following diffraction angles (2θ (degrees))=4.5±0.5, 9.0±0.5, and 14.7±0.5. In some embodiments, Form 1 exhibits an X-ray power diffraction pattern comprising peaks at the following diffraction angles (2θ (degrees))=4.5±0.5, 9.0±0.5, 14.7±0.5, and 18.1±0.5. In some embodiments, Form 1 exhibits an X-ray power diffraction pattern comprising peaks at the following diffraction angles (2θ (degrees))=4.5±0.5, 9.0±0.5, 14.7±0.5, 18.1±0.5. and 22.7±0.5. In some embodiments, Form 1 exhibits an X-ray power diffraction pattern comprising peaks at the following diffraction angles (2θ (degrees))=9.0±0.5 and 18.1±0.5. In some embodiments, Form 1 exhibits an X-ray power diffraction pattern comprising peaks at the following diffraction angles (2θ (degrees))=4.5±0.5 and 18.1±0.5. In some embodiments, Form 1 exhibits an X-ray power diffraction pattern comprising at least two peaks selected from the following diffraction angles (2θ (degrees))=4.5±0.5, 9.0±0.5, 14.7±0.5, 18.1±0.5. and 22.7±0.5. In some embodiments, Form 1 exhibits an X-ray power diffraction pattern comprising at least three peaks selected from the following diffraction angles (2θ (degrees))=4.5±0.5, 9.0±0.5, 14.7±0.5, 18.1±0.5, and 22.7±0.5. In some embodiments, Form 1 exhibits an X-ray power diffraction pattern comprising at least four peaks selected from the following diffraction angles (2θ (degrees))=4.5±0.5, 9.0±0.5, 14.7±0.5, 18.1±0.5, and 22.7±0.5.

In some embodiments, Form 1 exhibits an X-ray power diffraction pattern further comprising at least one characteristic XRPD peak selected from diffraction angles (2θ (degrees))=7.3±0.5, 10.7±0.5, 13.5±0.5, 16.6±0.5, 17.1±0.5, 17.7±0.5, and 19.4±0.5. In some embodiments, Form 1 exhibits an X-ray power diffraction pattern further comprising at least one characteristic XRPD peak selected from diffraction angles (2θ (degrees))=21.9±0.5, 23.1±0.5, 25.1±0.5, 27.0±0.5, 32.3±0.5, and 39.4±0.5.

In some embodiments, Form 1 exhibits an X-ray power diffraction pattern comprising at least two peaks selected from the following diffraction angles (2θ (degrees))= 4.5±0.5, 7.7±0.5, 9.0±0.5, 14.7±0.5, 17.1±0.5, 18.1±0.5, 19.4±0.5, and 22.7±0.5. In some embodiments, Form 1 exhibits an X-ray power diffraction pattern comprising at least three peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5. In some embodiments, Form 1 exhibits an X-ray power diffraction pattern comprising at least four peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5.

In some embodiments, Form 1 exhibits an X-ray powder diffraction pattern substantially the same as depicted in FIG. 1C.

In some embodiments, Form 1 has a differential scanning calorimetry curve substantially the same as shown in FIG. 2. In some embodiments, Form 1 exhibits an endotherm starting from about 255° C. based on differential scanning calorimetry.

In some embodiments, Form 1 has a dynamic vapor sorption plot substantially the same as shown in FIG. 3.

In some embodiments, Form 1 is an anhydrate.

In some embodiments, Form 1 is substantially free of other form or pattern of the compound of Formula II. In some embodiments, the other form or pattern is selected from the group consisting of Form 8, Form 10, Pattern 2, Pattern 3, Pattern 5, Pattern 6, Pattern 7, Pattern 11, and Pattern 12, and combinations thereof.

In some embodiments, Form 1 is substantially free of an impurity.

In some embodiments, Form 1 comprises less than about 10% area percentage of impurities as determined by HPLC. In some embodiments, Form 1 comprises less than about 9% area percentage of impurities as determined by HPLC. In some embodiments, Form 1 comprises less than about 8% area percentage of impurities as determined by HPLC. In some embodiments, Form 1 comprises less than about 7% area percentage of impurities as determined by HPLC. In some embodiments, Form 1 comprises less than about 6% area percentage of impurities as determined by HPLC. In some embodiments, Form 1 comprises less than about 5% area percentage of impurities as determined by HPLC. In some embodiments, Form 1 comprises less than about 4% area percentage of impurities as determined by HPLC. In some embodiments, Form 1 comprises less than about 3% area percentage of impurities as determined by HPLC. In some embodiments, Form 1 comprises less than about 2% area percentage of impurities as determined by HPLC. In some embodiments, Form 1 comprises less than about 1% area percentage of impurities as determined by HPLC.

In some embodiments, the impurity is Compound B, Compound C, or Compound D, or a combination thereof:

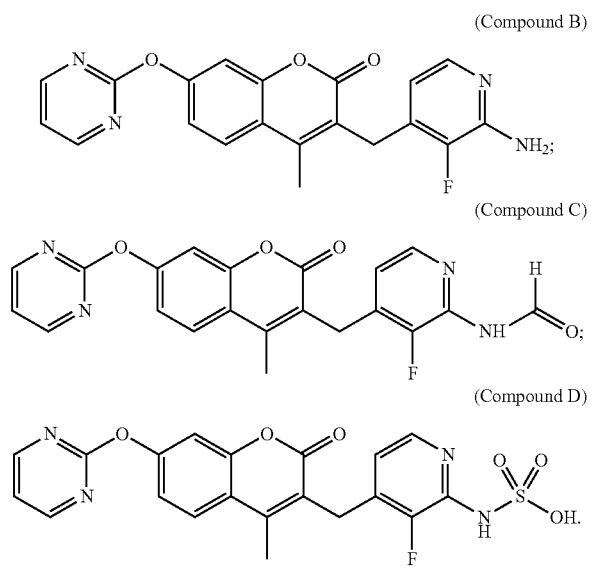

(Compound B)

(Compound C)

(Compound D)

In some embodiments, Form 1 comprises less than about 5.0% of Compound B as determined by HPLC. In some embodiments, Form 1 comprises less than about 4.0% of Compound B as determined by HPLC. In some embodiments, Form 1 comprises less than about 3.0% of Compound B as determined by HPLC. In some embodiments, Form 1 comprises less than about 2.0% of Compound B as determined by HPLC. In some embodiments, Form 1 comprises less than about 1.5% of Compound B as determined by HPLC. In some embodiments, Form 1 comprises less than about 1.0% of Compound B as determined by HPLC. In some embodiments, Form 1 comprises less than about 0.8% of Compound B as determined by HPLC. In some embodiments, Form 1 comprises less than about 0.6% of Compound B as determined by HPLC. In some embodiments, Form 1 comprises less than about 0.5% of Compound B as determined by HPLC. In some embodiments, Form 1 comprises less than about 0.4% of Compound B as determined by HPLC. In some embodiments, Form 1 comprises less than about of Compound B as determined by HPLC. In some embodiments, Form 1 comprises less than about 0.1% of Compound B as determined by HPLC.

In some embodiments, Form 1 comprises less than about 5.0% of Compound C as determined by HPLC. In some embodiments, Form 1 comprises less than about 4.0% of Compound C as determined by HPLC. In some embodiments, Form 1 comprises less than about 3.0% of Compound C as determined by HPLC. In some embodiments, Form 1 comprises less than about 2.0% of Compound C as determined by HPLC. In some embodiments, Form 1 comprises less than about 1.5% of Compound C as determined by HPLC. In some embodiments, Form 1 comprises less than about 1.0% of Compound C as determined by HPLC. In some embodiments, Form 1 comprises less than about 0.8% of Compound C as determined by HPLC. In some embodiments, Form 1 comprises less than about 0.6% of Compound C as determined by HPLC. In some embodiments, Form 1 comprises less than about 0.5% of Compound C as determined by HPLC. In some embodiments, Form 1 comprises less than about 0.4% of Compound C as determined by HPLC. In some embodiments, Form 1 comprises less than about of Compound C as determined by HPLC. In some embodiments, Form 1 comprises less than about 0.1% of Compound C as determined by HPLC.

In some embodiments, Form 1 comprises less than about 5.0% of Compound D as determined by HPLC. In some embodiments, Form 1 comprises less than about 4.0% of Compound D as determined by HPLC. In some embodiments, Form 1 comprises less than about 3.0% of Compound D as determined by HPLC. In some embodiments, Form 1 comprises less than about 2.0% of Compound D as determined by HPLC. In some embodiments, Form 1 comprises less than about 1.5% of Compound D as determined by HPLC. In some embodiments, Form 1 comprises less than about 1.0% of Compound D as determined by HPLC. In some embodiments, Form 1 comprises less than about 0.75% of Compound D as determined by HPLC. In some embodiments, Form 1 comprises less than about 0.50% of Compound D as determined by HPLC. In some embodiments, Form 1 comprises less than about 0.25% of Compound D as determined by HPLC. In some embodiments, Form 1 comprises less than about 0.20% of Compound D as determined by HPLC. In some embodiments, Form 1 comprises less than about 0.15% of Compound D as determined by HPLC. In some embodiments, Form 1 comprises less than about 0.10% of Compound D as determined by HPLC. In some embodiments, Form 1 comprises less than about 0.05% of Compound D as determined by HPLC.

In some embodiments, Form 1 characterized by unit cell dimension of a=19.5±1.0 Å, b=15.1±1.0 Å, c=6.9±1.0 Å. In some embodiments, Form 1 characterized by unit cell dimension of a=19.5±0.5 Å, b=15.1±0.5 Å, c=6.9±0.5 Å. In some embodiments, Form 1 characterized by unit cell dimension of a=19.5±0.2 Å, b=15.1±0.2 Å, c=6.9±0.2 Å. In some embodiments, Form 1 is characterized as having a monoclinic crystal system.

In an aspect, provided herein is a method of preparing crystalline Form 1 of a compound of Formula II:

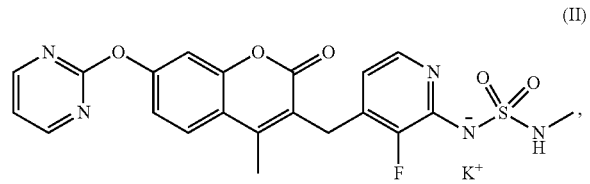 [SMILES: CNS(=O)(=O)[N-]c1nccc(Cc2c(C)c3ccc(Oc4ncccn4)cc3oc2=O)c1F ; [K+]]

comprising: (i) contacting a solution comprising a compound of Formula (I):

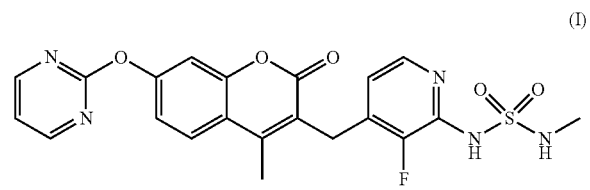 [SMILES: CNS(=O)(=O)Nc1nccc(Cc2c(C)c3ccc(Oc4ncccn4)cc3oc2=O)c1F]

in one or more solvent, with potassium hydroxide to form a mixture; (ii) heating the mixture prepared according to step (i) to about 40° C. to about 60° C.; (iii) cooling the heated mixture of step (ii) to about −10° C. to about 5° C. to form a precipitate; (iv) filtering the precipitate of step (iii) to isolate a solid; and (v) drying the solid from step (iv), to give Form 1.

In some embodiments, the solvent is a mixture of THF and water. In some embodiments, the THF and water are in a ratio of about 50:50 v/v. In some embodiments, the THF and water are in a ratio of about 60:40 v/v. In some embodiments, the THF and water are in a ratio of about 70:30 v/v. In some embodiments, the THF and water are in a ratio of about 80:20 v/v. In some embodiments, the THF and water are in a ratio of about 90:10 v/v. In some embodiments, the THF and water are in a ratio of about 95:5 v/v.

In some embodiments, the mixture is heated to about 30-40° C. in step (ii). In some embodiments, the mixture is heated to about 30-60° C. in step (ii). In some embodiments, the mixture is heated to about 30-50° C. in step (ii). In some embodiments, the mixture is heated to about 40-60° C. in step (ii). In some embodiments, the mixture is heated to about 40-50° C. in step (ii). In some embodiments, the mixture is heated to about 50-60° C. in step (ii). In some embodiments, the mixture is heated to about 35° C. in step (ii). In some embodiments, the mixture is heated to about 35° C. in step (ii). In some embodiments, the mixture is heated to about 40° C. in step (ii). In some embodiments, the mixture is heated to about 45° C. in step (ii). In some embodiments, the mixture is heated to about 50° C. in step (ii). In some embodiments, the mixture is heated to about 55° C. in step (ii). In some embodiments, the mixture is heated to about 60° C. in step (ii).

In some embodiments, the heated mixture of step (ii) is cooled to about −20-15° C. in step (iii). In some embodiments, the heated mixture of step (ii) is cooled to about −15-15° C. in step (iii). In some embodiments, the heated mixture of step (ii) is cooled to about −10-15° C. in step (iii). In some embodiments, the heated mixture of step (ii) is cooled to about −5-15° C. in step (iii). In some embodiments, the heated mixture of step (ii) is cooled to about −20-10° C. in step (iii). In some embodiments, the heated mixture of step (ii) is cooled to about −15-10° C. in step (iii). In some embodiments, the heated mixture of step (ii) is cooled to about −10-10° C. in step (iii). In some embodiments, the heated mixture of step (ii) is cooled to about −5-10° C. in step (iii). In some embodiments, the heated mixture of step (ii) is cooled to about −20-5° C. in step (iii). In some embodiments, the heated mixture of step (ii) is cooled to about −15-5° C. in step (iii). In some embodiments, the heated mixture of step (ii) is cooled to about −10-5° C. in step (iii). In some embodiments, the heated mixture of step (ii) is cooled to about −5-5° C. in step (iii). In some embodiments, the heated mixture of step (ii) is cooled to about −20-0° C. in step (iii). In some embodiments, the heated mixture of step (ii) is cooled to about −15-0° C. in step (iii). In some embodiments, the heated mixture of step (ii) is cooled to about −10-0° C. in step (iii). In some embodiments, the heated mixture of step (ii) is cooled to about −5-0° C. in step (iii). In some embodiments, the heated mixture of step (ii) is cooled to about −20° C. in step (iii). In some embodiments, the heated mixture of step (ii) is cooled to about −15° C. in step (iii). In some embodiments, the heated mixture of step (ii) is cooled to about −10° C. in step (iii). In some embodiments, the heated mixture of step (ii) is cooled to about −5° C. in step (iii). In some embodiments, the heated mixture of step (ii) is cooled to about 0° C. in step (iii). In some embodiments, the heated mixture of step (ii) is cooled to about 5° C. in step (iii). In some embodiments, the heated mixture of step (ii) is cooled to about 10° C. in step (iii). In some embodiments, the heated mixture of step (ii) is cooled to about 15° C. in step (iii).

In some embodiments, the drying in step (iv) occurs at an elevated temperature. In some embodiments, the drying in step (iv) occurs at a temperature of about 20° C. to about 40° C. In some embodiments, the drying in step (iv) occurs at a temperature of about 20° C. to about ° C. In some embodiments, the drying in step (iv) occurs at a temperature of about 20° C. to about 60° C. In some embodiments, the drying in step (iv) occurs at a temperature of about 30° C. to about 40° C. In some embodiments, the drying in step (iv) occurs at a temperature of about 30° C. to about 50° C. In some embodiments, the drying in step (iv) occurs at a temperature of about ° C. to about 60° C. In some embodiments, the drying in step (iv) occurs at a temperature of about 40° C. to about 50° C. In some embodiments, the drying in step (iv) occurs at a temperature of about 40° C. to about 60° C.

In some embodiments, the drying in step (iv) occurs under reduced pressure. In some embodiments, the drying in step (iv) occurs at an elevated temperature under reduced pressure. In some embodiments, the drying in step (iv) occurs at a temperature of about 20° C. to about 40° C. under reduced pressure. In some embodiments, the drying in step (iv) occurs at a temperature of about 20° C. to about 50° C. under reduced pressure. In some embodiments, the drying in step (iv) occurs at a temperature of about 20° C. to about 60° C. under reduced pressure. In some embodiments, the drying in step (iv) occurs at a temperature of about 30° C. to about 40° C. under reduced pressure. In some embodiments, the drying in step (iv) occurs at a temperature of about 30° C. to about 50° C. under reduced pressure. In some embodiments, the drying in step (iv) occurs at a temperature of about 30° C. to about 60° C. under reduced pressure. In some embodiments, the drying in step (iv) occurs at a temperature of about 40° C. to about 50° C. under reduced pressure. In some embodiments, the drying in step (iv) occurs at a temperature of about ° C. to about 60° C. under reduced pressure.

In some embodiments, crystalline Form 1 of a compound of Formula II:

(II)

prepared according to the methods described above.

In some embodiments, Form 1 exhibits an X-ray power diffraction pattern comprising a characteristic XRPD peak at the following diffraction angle (2θ (degrees))=9.0±0.5. In some embodiments, Form 1 exhibits an X-ray power diffraction pattern further comprising a characteristic XRPD peak at the following diffraction angle (2θ (degrees))=4.5±0.5. In some embodiments, Form 1 exhibits an X-ray power diffraction pattern further comprising a characteristic XRPD peak at the following diffraction angle (2θ (degrees))=14.7±0.5. In some embodiments, Form 1 exhibits an X-ray power diffraction pattern further comprising a characteristic XRPD peak at the following diffraction angle (2θ (degrees))=18.1±0.5. In some embodiments, Form 1 exhibits an X-ray power diffraction pattern further comprising a characteristic XRPD peak at the following diffraction angle (2θ (degrees))=22.7±0.5. In some embodiments, Form 1 exhibits an X-ray power diffraction pattern comprising peaks at the following diffraction angles (2θ (degrees))=4.5±0.5 and 9.0±0.5. In some embodiments, Form 1 exhibits an X-ray power diffraction pattern comprising peaks at the following diffraction angles (2θ (degrees))=4.5±0.5, 9.0±0.5, and 14.7±0.5. In some embodiments, Form 1 exhibits an X-ray power diffraction pattern comprising peaks at the following diffraction angles (2θ (degrees))=4.5±0.5, 9.0±0.5, 14.7±0.5, and 18.1±0.5. In some embodiments, Form 1 exhibits an X-ray power diffraction pattern comprising peaks at the following diffraction angles (2θ (degrees))=4.5±0.5, 9.0±0.5, 14.7±0.5, 18.1±0.5. and 22.7±0.5. In some embodiments, Form 1 exhibits an X-ray power diffraction pattern comprising peaks at the following diffraction angles (2θ (degrees))=9.0±0.5 and 18.1±0.5. In some embodiments, Form 1 exhibits an X-ray power diffraction pattern comprising peaks at the following diffraction angles (2θ (degrees))=4.5±0.5 and 18.1±0.5. In some embodiments, Form 1 exhibits an X-ray power diffraction pattern comprising at least two peaks selected from the following diffraction angles (2θ (degrees))=4.5±0.5, 9.0±0.5, 14.7±0.5, 18.1±0.5. and 22.7±0.5. In some embodiments, Form 1 exhibits an X-ray power diffraction pattern comprising at least three peaks selected from the following diffraction angles (2θ (degrees))=4.5±0.5, 9.0±0.5, 14.7±0.5, 18.1±0.5, and 22.7±0.5. In some embodiments, Form 1 exhibits an X-ray power diffraction pattern comprising at least four peaks selected from the following diffraction angles (2θ (degrees))=4.5±0.5, 9.0±0.5, 14.7±0.5, 18.1±0.5, and 22.7±0.5.

In some embodiments, Form 1 exhibits an X-ray power diffraction pattern further comprising at least one characteristic XRPD peak selected from diffraction angles (2θ (degrees))=7.3±0.5, 10.7±0.5, 13.5±0.5, 16.6±0.5, 17.1±0.5, 17.7±0.5, and 19.4±0.5. In some embodiments, Form 1 exhibits an X-ray power diffraction pattern further comprising at least one characteristic XRPD peak selected from diffraction angles (2θ (degrees))=21.9±0.5, 23.1±0.5, 27.0±0.5, 32.3±0.5, and 39.4±0.5.

In some embodiments, Form 1 exhibits an X-ray power diffraction pattern comprising at least two peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5. In some embodiments, Form 1 exhibits an X-ray power diffraction pattern comprising at least three peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5. In some embodiments, Form 1 exhibits an X-ray power diffraction pattern comprising at least four peaks selected from the following diffraction angles (2θ (degrees))=4.5±0.5, 7.7±0.5, 9.0±0.5, 14.7±0.5, 17.1±0.5, 18.1±0.5, 19.4±0.5, and 22.7±0.5.

In some embodiments, Form 1 exhibits an X-ray power diffraction pattern comprising a characteristic XRPD peak at the following diffraction angle (2θ (degrees))=9.0±0.3. In some embodiments, Form 1 exhibits an X-ray power diffraction pattern further comprising a characteristic XRPD peak at the following diffraction angle (2θ (degrees))=4.5±0.3. In some embodiments, Form 1 exhibits an X-ray power diffraction pattern further comprising a characteristic XRPD peak at the following diffraction angle (2θ (degrees))=14.7±0.3. In some embodiments, Form 1 exhibits an X-ray power diffraction pattern further comprising a characteristic XRPD peak at the following diffraction angle (2θ (degrees))=18.1±0.3. In some embodiments, Form 1 exhibits an X-ray power diffraction pattern further comprising a characteristic XRPD peak at the following diffraction angle (2θ (degrees))=22.7±0.3. In some embodiments, Form 1 exhibits an X-ray power diffraction pattern comprising peaks at the following diffraction angles (2θ (degrees))=4.5±0.3 and 9.0±0.3. In some embodiments, Form 1 exhibits an X-ray power diffraction pattern comprising peaks at the following diffraction angles (2θ (degrees))=4.5±0.3, 9.0±0.3, and 14.7±0.3. In some embodiments, Form 1 exhibits an X-ray power diffraction pattern comprising peaks at the following diffraction angles (2θ (degrees))=4.5±0.3, 9.0±0.3, 14.7±0.3, and 18.1±0.3. In some embodiments, Form 1 exhibits an X-ray power diffraction pattern comprising peaks at the following diffraction angles (2θ (degrees))=4.5±0.3, 9.0±0.3, 14.7±0.3, 18.1±0.3. and 22.7±0.3. In some embodiments, Form 1 exhibits an X-ray power diffraction pattern comprising peaks at the following diffraction angles (2θ (degrees))=9.0±0.3 and 18.1±0.3. In some embodiments, Form 1 exhibits an X-ray power diffraction pattern comprising peaks at the following diffraction angles (2θ (degrees))=4.5±0.3 and 18.1±0.3. In some embodiments, Form 1 exhibits an X-ray power diffraction pattern comprising at least two peaks selected from the following diffraction angles (2θ (degrees))=4.5±0.3, 9.0±0.3, 14.7±0.3, 18.1±0.3. and 22.7±0.3. In some embodiments, Form 1 exhibits an X-ray power diffraction pattern comprising at least three peaks selected from the following diffraction angles (2θ (degrees))=4.5±0.3, 9.0±0.3, 14.7±0.3, 18.1±0.3, and 22.7±0.3. In some embodiments, Form 1 exhibits an X-ray power diffraction pattern comprising at least four peaks selected from the following diffraction angles (2θ (degrees))=4.5±0.3, 9.0±0.3, 14.7±0.3, 18.1±0.3, and 22.7±0.3.

In some embodiments, Form 1 exhibits an X-ray power diffraction pattern further comprising at least one characteristic XRPD peak selected from diffraction angles (2θ (degrees))=7.3±0.3, 10.7±0.3, 13.5±0.3, 16.6±0.3, 17.1±0.3, 17.7±0.3, and 19.4±0.3. In some embodiments, Form 1 exhibits an X-ray power diffraction pattern further comprising at least one characteristic XRPD peak selected from diffraction angles (2θ (degrees))=21.9±0.3, 23.1±0.3, 25.1±0.3, 27.0±0.3, 32.3±0.3, and 39.4±0.3.

In some embodiments, Form 1 exhibits an X-ray power diffraction pattern comprising at least two peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3. In some embodiments, Form 1 exhibits an X-ray power diffraction pattern comprising at least three peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3. In some embodiments, Form 1 exhibits an X-ray power diffraction pattern comprising at least four peaks selected from the following diffraction angles (2θ (degrees))=4.5±0.3, 7.7±0.3, 9.0±0.3, 14.7±0.3, 17.1±0.3, 18.1±0.3, 19.4±0.3, and 22.7±0.3.

In some embodiments, Form 1 exhibits an X-ray power diffraction pattern comprising a characteristic XRPD peak at the following diffraction angle (2θ (degrees))=9.0±0.2. In some embodiments, Form 1 exhibits an X-ray power diffraction pattern further comprising a characteristic XRPD peak at the following diffraction angle (2θ (degrees))=4.5±0.2. In some embodiments, Form 1 exhibits an X-ray power diffraction pattern further comprising a characteristic XRPD peak at the following diffraction angle (2θ (degrees))=14.7±0.2. In some embodiments, Form 1 exhibits an X-ray power diffraction pattern further comprising a characteristic XRPD peak at the following diffraction angle (2θ (degrees))=18.1±0.2. In some embodiments, Form 1 exhibits an X-ray power diffraction pattern further comprising a characteristic XRPD peak at the following diffraction angle (2θ (degrees))=22.7±0.2. In some embodiments, Form 1 exhibits an X-ray power diffraction pattern comprising peaks at the following diffraction angles (2θ (degrees))=4.5±0.2 and 9.0±0.2. In some embodiments, Form 1 exhibits an X-ray power diffraction pattern comprising peaks at the following diffraction angles (2θ (degrees))=4.5±0.2, 9.0±0.2, and 14.7±0.2. In some embodiments, Form 1 exhibits an X-ray power diffraction pattern comprising peaks at the following diffraction angles (2θ (degrees))=4.5±0.2, 9.0±0.2, 14.7±0.2, and 18.1±0.2. In some embodiments, Form 1 exhibits an X-ray power diffraction pattern comprising peaks at the following diffraction angles (2θ (degrees))=4.5±0.2, 9.0±0.2, 14.7±0.2, 18.1±0.2. and 22.7±0.2. In some embodiments, Form 1 exhibits an X-ray power diffraction pattern comprising peaks at the following diffraction angles (2θ (degrees))=9.0±0.2 and 18.1±0.2. In some embodiments, Form 1 exhibits an X-ray power diffraction pattern comprising peaks at the following diffraction angles (2θ (degrees))=4.5±0.2 and 18.1±0.2. In some embodiments, Form 1 exhibits an X-ray power diffraction pattern comprising at least two peaks selected from the following diffraction angles (2θ (degrees))=4.5±0.2, 9.0±0.2, 14.7±0.2, 18.1±0.2. and 22.7±0.2. In some embodiments, Form 1 exhibits an X-ray power diffraction pattern comprising at least three peaks selected from the following diffraction angles (2θ (degrees))=4.5±0.2, 9.0±0.2, 14.7±0.2, 18.1±0.2, and 22.7±0.2. In some embodiments, Form 1 exhibits an X-ray power diffraction pattern comprising at least four peaks selected from the following diffraction angles (2θ (degrees))=4.5±0.2, 9.0±0.2, 14.7±0.2, 18.1±0.2, and 22.7±0.2.

In some embodiments, Form 1 exhibits an X-ray power diffraction pattern further comprising at least one characteristic XRPD peak selected from diffraction angles (2θ (degrees))=7.3±0.2, 10.7±0.2, 13.5±0.2, 16.6±0.2, 17.1±0.2, 17.7±0.2, and 19.4±0.2. In some embodiments, Form 1 exhibits an X-ray power diffraction pattern further comprising at least one characteristic XRPD peak selected from diffraction angles (2θ (degrees))=21.9±0.2, 23.1±0.2, 25.1±0.2, 27.0±0.2, 32.3±0.2, and 39.4±0.2.

In some embodiments, Form 1 exhibits an X-ray power diffraction pattern comprising at least two peaks selected from the following diffraction angles (2θ (degrees))=4.5±0.2, 7.7±0.2, 9.0±0.2, 14.7±0.2, 17.1±0.2, 18.1±0.2, 19.4±0.2, and 22.7±0.2. In some embodiments, Form 1 exhibits an X-ray power diffraction pattern comprising at least three peaks selected from the following diffraction angles (2θ (degrees))=4.5±0.2, 7.7±0.2, 9.0±0.2, 14.7±0.2, 17.1±0.2, 18.1±0.2, 19.4±0.2, and 22.7±0.2. In some embodiments, Form 1 exhibits an X-ray power diffraction pattern comprising at least four peaks selected from the following diffraction angles (2θ (degrees))=4.5±0.2, 7.7±0.2, 9.0±0.2, 14.7±0.2, 17.1±0.2, 18.1±0.2, 19.4±0.2, and 22.7±0.2.

In some embodiments, Form 1 exhibits an X-ray powder diffraction pattern substantially the same as depicted in FIG. 1C.

In some embodiments, Form 1 exhibits an X-ray power diffraction pattern comprising a characteristic XRPD peak at the following diffraction angle (2θ (degrees))=8.8±0.2. In some embodiments, Form 1 exhibits an X-ray power diffraction pattern comprising a characteristic XRPD peak at the following diffraction angle (2θ (degrees))=17.9±0.2. In some embodiments, Form 1 exhibits an X-ray power diffraction pattern comprising a characteristic XRPD peak at the following diffraction angle (2θ (degrees))=22.5±0.2. In some embodiments, Form 1 exhibits an X-ray power diffraction pattern comprising peaks at the following diffraction angles (2θ (degrees))=17.9±0.2 and 8.8±0.2. In some embodiments, Form 1 exhibits an X-ray power diffraction pattern comprising peaks at the following diffraction angles (2θ (degrees))=17.9±0.2, 8.8±0.2, and 22.5±0.2. In some embodiments, Form 1 exhibits an X-ray power diffraction pattern comprising peaks at the following diffraction angles (2θ (degrees))=17.9±0.2, 8.8±0.2, 22.5±0.2, and 14.5±0.2. In some embodiments, Form 1 exhibits an X-ray power diffraction pattern further comprising at least one characteristic XRPD peak selected from diffraction angles (2θ (degrees))=10.5±0.2, 13.3±0.2, 16.9±0.2, and 19.2±0.2. In some embodiments, Form 1 exhibits an X-ray power diffraction pattern further comprising at least one characteristic XRPD peak selected from diffraction angles (2θ (degrees))=10.5±0.2, 13.3±0.2, 16.9±0.2, 19.2±0.2, 21.3±0.2, 21.8±0.2, 24.9±0.2, 27.1±0.2, and 27.8±0.2. In some embodiments, Form 1 exhibits an X-ray power diffraction pattern comprising peaks at the following diffraction angles (2θ (degrees))=17.9±0.2, 8.8±0.2, 22.5±0.2, 14.5±0.2, 10.5±0.2, 13.3±0.2, 16.9±0.2, 19.2±0.2, 21.3±0.2, 21.8±0.2, 24.9±0.2, 27.1±0.2, and 27.8±0.2.

In some embodiments, Form 1 exhibits an X-ray power diffraction pattern comprising peaks at the following diffraction angles (2θ (degrees))=17.9±0.2, 8.8±0.2, and 22.5±0.2. In some embodiments, Form 1 exhibits an X-ray power diffraction pattern further comprising at least one characteristic XRPD peak selected from diffraction angles (2θ (degrees))=14.5±0.2, 39.3±0.2, and 10.5±0.2. In some embodiments, Form 1 exhibits an X-ray power diffraction pattern comprising peaks at the following diffraction angles (2θ (degrees))=17.9±0.2, 8.8±0.2, 22.5±0.2, 14.5±0.2, 39.3±0.2, and 10.5±0.2. In some embodiments, Form 1 exhibits an X-ray power diffraction pattern further comprising at least one characteristic XRPD peak selected from diffraction angles (2θ (degrees))=10.5±0.2, 13.3±0.2, 16.9±0.2, 19.2±0.2, 21.3±0.2, 21.8±0.2, 24.9±0.2, 27.1±0.2, 27.8±0.2, and 32.2±0.2. In some embodiments, Form 1 exhibits an X-ray power diffraction pattern comprising peaks at the following diffraction angles (2θ (degrees))=8.8±0.2, 10.5±0.2, 13.3±0.2, 14.5±0.2, 16.9±0.2, 17.9±0.2, 19.2±0.2, 21.3±0.2, 21.8±0.2, 22.5±0.2, 24.9±0.2, 27.1±0.2, 27.8±0.2, 32.2±0.2, and 39.3±0.2.

In some embodiments, Form 1 exhibits an X-ray power diffraction pattern comprising a characteristic XRPD peak at the following diffraction angle (2θ (degrees))=8.8±0.3. In some embodiments, Form 1 exhibits an X-ray power diffraction pattern further comprising a characteristic XRPD peak at the following diffraction angle (2θ (degrees))=17.9±0.3. In some embodiments, Form 1 exhibits an X-ray power diffraction pattern further comprising a characteristic XRPD peak at the following diffraction angle (2θ (degrees))=22.5±0.3. In some embodiments, Form 1 exhibits an X-ray power diffraction pattern comprising peaks at the following diffraction angles (2θ (degrees))=17.9±0.3 and 8.8±0.3. In some embodiments, Form 1 exhibits an X-ray power diffraction pattern comprising peaks at the following diffraction angles (2θ (degrees))=17.9±0.3, 8.8±0.3, and 22.5±0.3. In some embodiments, Form 1 exhibits an X-ray power diffraction pattern comprising peaks at the following diffraction angles (2θ (degrees))=17.9±0.3, 8.8±0.3, 22.5±0.3, and 14.5±0.3. In some embodiments, Form 1 exhibits an X-ray power diffraction pattern further comprising at least one characteristic XRPD peak selected from diffraction angles (2θ (degrees))=10.5±0.3, 13.3±0.3, 16.9±0.3, and 19.2±0.3. In some embodiments, Form 1 exhibits an X-ray power diffraction pattern further comprising at least one characteristic XRPD peak selected from diffraction angles (2θ (degrees))=10.5±0.3, 13.3±0.3, 16.9±0.3, 19.2±0.3, 21.3±0.3, 21.8±0.3, 24.9±0.3, 27.1±0.3, and 27.8±0.3. In some embodiments, Form 1 exhibits an X-ray power diffraction pattern comprising peaks at the following diffraction angles (2θ (degrees))=17.9±0.3, 8.8±0.3, 22.5±0.3, 14.5±0.3, 10.5±0.3, 13.3±0.3, 16.9±0.3, 19.2±0.3, 21.3±0.3, 21.8±0.3, 24.9±0.3, 27.1±0.3, and 27.8±0.3.

In some embodiments, Form 1 exhibits an X-ray power diffraction pattern comprising peaks at the following diffraction angles (2θ (degrees))=17.9±0.3, 8.8±0.3, and 22.5±0.3. In some embodiments, Form 1 exhibits an X-ray power diffraction pattern further comprising at least one characteristic XRPD peak selected from diffraction angles (2θ (degrees))=14.5±0.3, 39.3±0.3, and 10.5±0.3. In some embodiments, Form 1 exhibits an X-ray power diffraction pattern comprising peaks at the following diffraction angles (2θ (degrees))=17.9±0.3, 8.8±0.3, 22.5±0.3, 14.5±0.3, 39.3±0.3, and 10.5±0.3. In some embodiments, Form 1 exhibits an X-ray power diffraction pattern further comprising at least one characteristic XRPD peak selected from diffraction angles (2θ (degrees))=10.5±0.3, 13.3±0.3, 16.9±0.3, 19.2±0.3, 21.3±0.3, 21.8±0.3, 24.9±0.3, 27.1±0.3, 27.8±0.3, and 32.2±0.3. In some embodiments, Form 1 exhibits an X-ray power diffraction pattern comprising peaks at the following diffraction angles (2θ (degrees))=8.8±0.3, 10.5±0.3, 13.3±0.3, 14.5±0.3, 16.9±0.3, 17.9±0.3, 19.2±0.3, 21.3±0.3, 21.8±0.3, 22.5±0.3, 24.9±0.3, 27.1±0.3, 27.8±0.3, 32.2±0.3, and 39.3±0.3.

In some embodiments, Form 1 exhibits an X-ray power diffraction pattern comprising a characteristic XRPD peak at the following diffraction angle (2θ (degrees))=8.8±0.5. In some embodiments, Form 1 exhibits an X-ray power diffraction pattern further comprising a characteristic XRPD peak at the following diffraction angle (2θ (degrees))=17.9±0.5. In some embodiments, Form 1 exhibits an X-ray power diffraction pattern further comprising a characteristic XRPD peak at the following diffraction angle (2θ (degrees))=22.5±0.5. In some embodiments, Form 1 exhibits an X-ray power diffraction pattern comprising peaks at the following diffraction angles (2θ (degrees))=17.9±0.5 and 8.8±0.5. In some embodiments, Form 1 exhibits an X-ray power diffraction pattern comprising peaks at the following diffraction angles (2θ (degrees))=17.9±0.5, 8.8±0.5, and 22.5±0.5. In some embodiments, Form 1 exhibits an X-ray power diffraction pattern comprising peaks at the following diffraction angles (2θ (degrees))=17.9±0.5, 8.8±0.5, 22.5±0.5, and 14.5±0.5. In some embodiments, Form 1 exhibits an X-ray power diffraction pattern further comprising at least one characteristic XRPD peak selected from diffraction angles (2θ (degrees))=10.5±0.5, 13.3±0.5, 16.9±0.5, and 19.2±0.5. In some embodiments, Form 1 exhibits an X-ray power diffraction pattern further comprising at least one characteristic XRPD peak selected from diffraction angles (2θ (degrees))=10.5±0.5, 13.3±0.5, 16.9±0.5, 19.2±0.5, 21.3±0.5, 21.8±0.5, 24.9±0.5, 27.1±0.5, and 27.8±0.5. In some embodiments, Form 1 exhibits an X-ray power diffraction pattern comprising peaks at the following diffraction angles (2θ (degrees))=17.9±0.5, 8.8±0.5, 22.5±0.5, 14.5±0.5, 10.5±0.5, 13.3±0.5, 16.9±0.5, 19.2±0.5, 21.3±0.5, 21.8±0.5, 24.9±0.5, 27.1±0.5, and 27.8±0.5.

In some embodiments, Form 1 exhibits an X-ray power diffraction pattern comprising peaks at the following diffraction angles (2θ (degrees))=17.9±0.5, 8.8±0.5, and 22.5±0.5. In some embodiments, Form 1 exhibits an X-ray power diffraction pattern further comprising at least one characteristic XRPD peak selected from diffraction angles (2θ (degrees))=14.5±0.5, 39.3±0.5, and 10.5±0.5. In some embodiments, Form 1 exhibits an X-ray power diffraction pattern comprising peaks at the following diffraction angles (2θ (degrees))=17.9±0.5, 8.8±0.5, 22.5±0.5, 14.5±0.5, 39.3±0.5, and 10.5±0.5. In some embodiments, Form 1 exhibits an X-ray power diffraction pattern further comprising at least one characteristic XRPD peak selected from diffraction angles (2θ (degrees))=10.5±0.5, 13.3±0.5, 16.9±0.5, 19.2±0.5, 21.3±0.5, 21.8±0.5, 24.9±0.5, 27.1±0.5, 27.8±0.5, and 32.2±0.5. In some embodiments, Form 1 exhibits an X-ray power diffraction pattern comprising peaks at the following diffraction angles (2θ (degrees))=8.8±0.5, 10.5±0.5, 13.3±0.5, 14.5±0.5, 16.9±0.5, 17.9±0.5, 19.2±0.5, 21.3±0.5, 21.8±0.5, 22.5±0.5, 24.9±0.5, 27.1±0.5, 27.8±0.5, 32.2±0.5, and 39.3±0.5.

In some embodiments, Form 1 exhibits an X-ray powder diffraction pattern substantially the same as depicted in FIG. 1B.

In some embodiments, Form 1 has a differential scanning calorimetry curve substantially the same as shown in FIG. 2. In some embodiments, Form 1 exhibits an endotherm starting from about 255° C. based on differential scanning calorimetry.

In some embodiments, Form 1 has a dynamic vapor sorption plot substantially the same as shown in FIG. 3.

In some embodiments, Form 1 is an anhydrate.

In some embodiments, Form 1 comprises less than about 3.0% water. In some embodiments, Form 1 comprises less than about 2.0% water. In some embodiments, Form 1 comprises less than about 1.0% water. In some embodiments, Form 1 comprises less than about water.

Form 8

In another aspect, provided herein is crystalline Form 8 of a compound of Formula II:

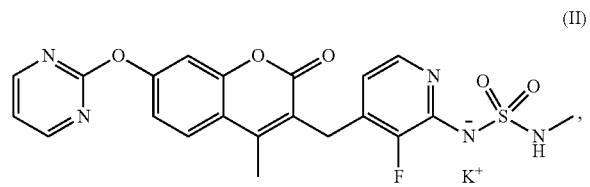 [SMILES: CNS(=O)(=O)[N-]c1nccc(Cc2c(C)c3ccc(Oc4ncccn4)cc3oc2=O)c1F ; [K+]]

(II)

wherein Form 8 exhibits an X-ray power diffraction pattern comprising a characteristic XRPD peak at the following diffraction angle (2θ (degrees))=9.9±0.2.

In some embodiments, Form 8 exhibits an X-ray powder diffraction pattern comprising peaks at the following diffraction angles (2θ (degrees)) 9.9±0.2 and 16.8±0.2. In some embodiments, Form 8 exhibits an X-ray powder diffraction pattern comprising peaks at the following diffraction angles (2θ (degrees)) 9.9±0.2, 16.8±0.2, and 20.2±0.2. In some embodiments, Form 8 exhibits an X-ray powder diffraction pattern comprising peaks at the following diffraction angles (2θ (degrees))=9.9±0.2, 14.8±0.2, 16.8±0.2, and 20.2±0.2. In some embodiments, Form 8 exhibits an X-ray powder diffraction pattern comprising peaks at the following diffraction angles (2θ (degrees))=9.9±0.2, 13.3±0.2, 14.8±0.2, 16.8±0.2, and 20.2±0.2. In some embodiments, Form 8 exhibits an X-ray powder diffraction pattern further comprising at least one characteristic XRPD peak selected from diffraction angles (2θ (degrees))=6.9±0.2, 9.0±0.2, 17.5±0.2, 17.9±0.2, 21.2±0.2, 23.7±0.2, 24.5±0.2, 25.3±0.2, 26.2±0.2, and 27.1±0.2. In some embodiments, Form 8 exhibits an X-ray powder diffraction pattern further comprising at least one characteristic XRPD peak selected from diffraction angles (2θ (degrees))=4.6±0.2, 5.2±0.2, 7.7±0.2, 8.5±0.2, 10.3±0.2, 11.7±0.2, 12.4±0.2, 12.9±0.2, 13.3±0.2, 14.2±0.2, and 14.8±0.2. In some embodiments, Form 8 exhibits an X-ray powder diffraction pattern further comprising at least one characteristic XRPD peak selected from diffraction angles (2θ (degrees))=23.1±0.2, 25.8±0.2, and 28.2±0.2. In some embodiments, In some embodiments, Form 8 exhibits an X-ray powder diffraction pattern further comprising at least one characteristic XRPD peak selected from diffraction angles (2θ (degrees))=31.2±0.2 and 37.8±0.2. In some embodiments, Form 8 exhibits an X-ray powder diffraction pattern comprising peaks at the following diffraction angles (2θ (degrees))=6.9±0.2, 9.0±0.2, 9.9±0.2, 13.3±0.2, 14.8±0.2, 16.8±0.2, 17.5±0.2, 17.9±0.2, 20.2±0.2, 21.2±0.2, 23.7±0.2, 24.5±0.2, 25.3±0.2, 26.2±0.2, and 27.1±0.2.

In some embodiments, also provided herein is crystalline Form 8 of a compound of Formula II:

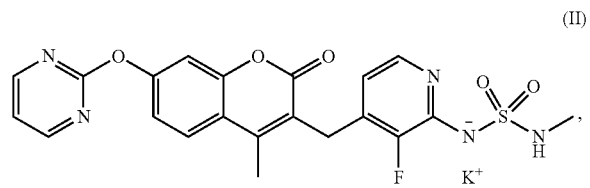 [SMILES: CNS(=O)(=O)[N-]c1nccc(Cc2c(C)c3ccc(Oc4ncccn4)cc3oc2=O)c1F ; [K+]]

(II)

wherein Form 8 exhibits an X-ray power diffraction pattern comprising a characteristic XRPD peak at the following diffraction angle (2θ (degrees))=9.9±0.3.

In some embodiments, Form 8 exhibits an X-ray powder diffraction pattern comprising peaks at the following diffraction angles (2θ (degrees)) 9.9±0.3 and 16.8±0.3. In some embodiments, Form 8 exhibits an X-ray powder diffraction pattern comprising peaks at the following diffraction angles (2θ (degrees)) 9.9±0.3, 16.8±0.3, and 20.3±0.3. In some embodiments, Form 8 exhibits an X-ray powder diffraction pattern comprising peaks at the following diffraction angles (2θ (degrees))=9.9±0.3, 14.8±0.3, 16.8±0.3, and 20.3±0.3. In some embodiments, Form 8 exhibits an X-ray powder diffraction pattern comprising peaks at the following diffraction angles (2θ (degrees))=9.9±0.3, 13.3±0.3, 14.8±0.3, 16.8±0.3, and 20.3±0.3. In some embodiments, Form 8 exhibits an X-ray powder diffraction pattern further comprising at least one characteristic XRPD peak selected from diffraction angles (2θ (degrees))=6.9±0.3, 9.0±0.3, 17.5±0.3, 17.9±0.3, 21.2±0.3, 23.7±0.3, 24.5±0.3, 25.3±0.3, 26.2±0.3, and 27.1±0.3. In some embodiments, Form 8 exhibits an X-ray powder diffraction pattern further comprising at least one characteristic XRPD peak selected from diffraction angles (2θ (degrees))=4.6±0.3, 5.2±0.3, 7.7±0.3, 8.5±0.3, 10.3±0.3, 11.7±0.3, 12.4±0.3, 12.9±0.3, 13.3±0.3, 14.2±0.3, and 14.8±0.3. In some embodiments, Form 8 exhibits an X-ray powder diffraction pattern further comprising at least one characteristic XRPD peak selected from diffraction angles (2θ (degrees))=23.1±0.3, 25.8±0.3, and 28.2±0.3. In some embodiments, In some embodiments, Form 8 exhibits an X-ray powder diffraction pattern further comprising at least one characteristic XRPD peak selected from diffraction angles (2θ (degrees))=31.2±0.3 and 37.8±0.3. In some embodiments, Form 8 exhibits an X-ray powder diffraction pattern comprising peaks at the following diffraction angles (2θ (degrees))=6.9±0.3, 9.0±0.3, 9.9±0.3, 13.3±0.3, 14.8±0.3, 16.8±0.3, 17.5±0.3, 17.9±0.3, 20.3±0.3, 21.2±0.3, 23.7±0.3, 24.5±0.3, 25.3±0.3, 26.2±0.3, and 27.1±0.3.

In some embodiments, also provided herein is crystalline Form 8 of a compound of Formula II:

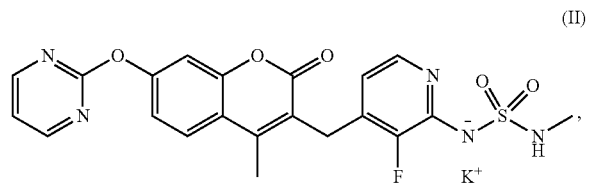 [SMILES: CNS(=O)(=O)[N-]c1nccc(Cc2c(C)c3ccc(Oc4ncccn4)cc3oc2=O)c1F ; [K+]]

(II)

wherein Form 8 exhibits an X-ray power diffraction pattern comprising a characteristic XRPD peak at the following diffraction angle (2θ (degrees))=9.9±0.5.

In some embodiments, Form 8 exhibits an X-ray powder diffraction pattern comprising peaks at the following diffraction angles (2θ (degrees)) 9.9±0.5 and 16.8±0.5. In some embodiments, Form 8 exhibits an X-ray powder diffraction pattern comprising peaks at the following diffraction angles (2θ (degrees)) 9.9±0.5, 16.8±0.5, and 20.3±0.5. In some embodiments, Form 8 exhibits an X-ray powder diffraction pattern comprising peaks at the following diffraction angles (2θ (degrees))=9.9±0.5, 14.8±0.5, 16.8±0.5, and 20.3±0.5. In some embodiments, Form 8 exhibits an X-ray powder diffraction pattern comprising peaks at the following diffraction angles (2θ (degrees))=9.9±0.5, 13.3±0.5, 14.8±0.5, 16.8±0.5, and 20.3±0.5. In some embodiments, Form 8 exhibits an X-ray powder diffraction pattern further comprising at least one characteristic XRPD peak selected from diffraction angles (2θ (degrees))=6.9±0.5, 9.0±0.5, 17.5±0.5, 17.9±0.5, 21.2±0.5, 23.7±0.5, 24.5±0.5, 25.3±0.5, 26.2±0.5, and 27.1±0.5. In some embodiments, Form 8 exhibits an X-ray powder diffraction pattern further comprising at least one characteristic XRPD peak selected from diffraction angles (2θ (degrees))=4.6±0.5, 5.2±0.5, 7.7±0.5, 8.5±0.5, 10.3±0.5, 11.7±0.5, 12.4±0.5, 12.9±0.5, 13.3±0.5, 14.2±0.5, and 14.8±0.5. In some embodiments, Form 8 exhibits an X-ray powder diffraction pattern further comprising at least one characteristic XRPD peak selected from diffraction angles (2θ (degrees))=23.1±0.5, 25.8±0.5, and 28.2±0.5. In some embodiments, In some embodiments, Form 8 exhibits an X-ray powder diffraction pattern further comprising at least one characteristic XRPD peak selected from diffraction angles (2θ (degrees))=31.2±0.5 and 37.8±0.5. In some embodiments, Form 8 exhibits an X-ray powder diffraction pattern comprising peaks at the following diffraction angles (2θ (degrees))=6.9±0.5, 9.0±0.5, 9.9±0.5, 13.3±0.5, 14.8±0.5, 16.8±0.5, 17.5±0.5, 17.9±0.5, 20.3±0.5, 21.2±0.5, 23.7±0.5, 24.5±0.5, 25.3±0.5, 26.2±0.5, and 27.1±0.5.

Figure 13:
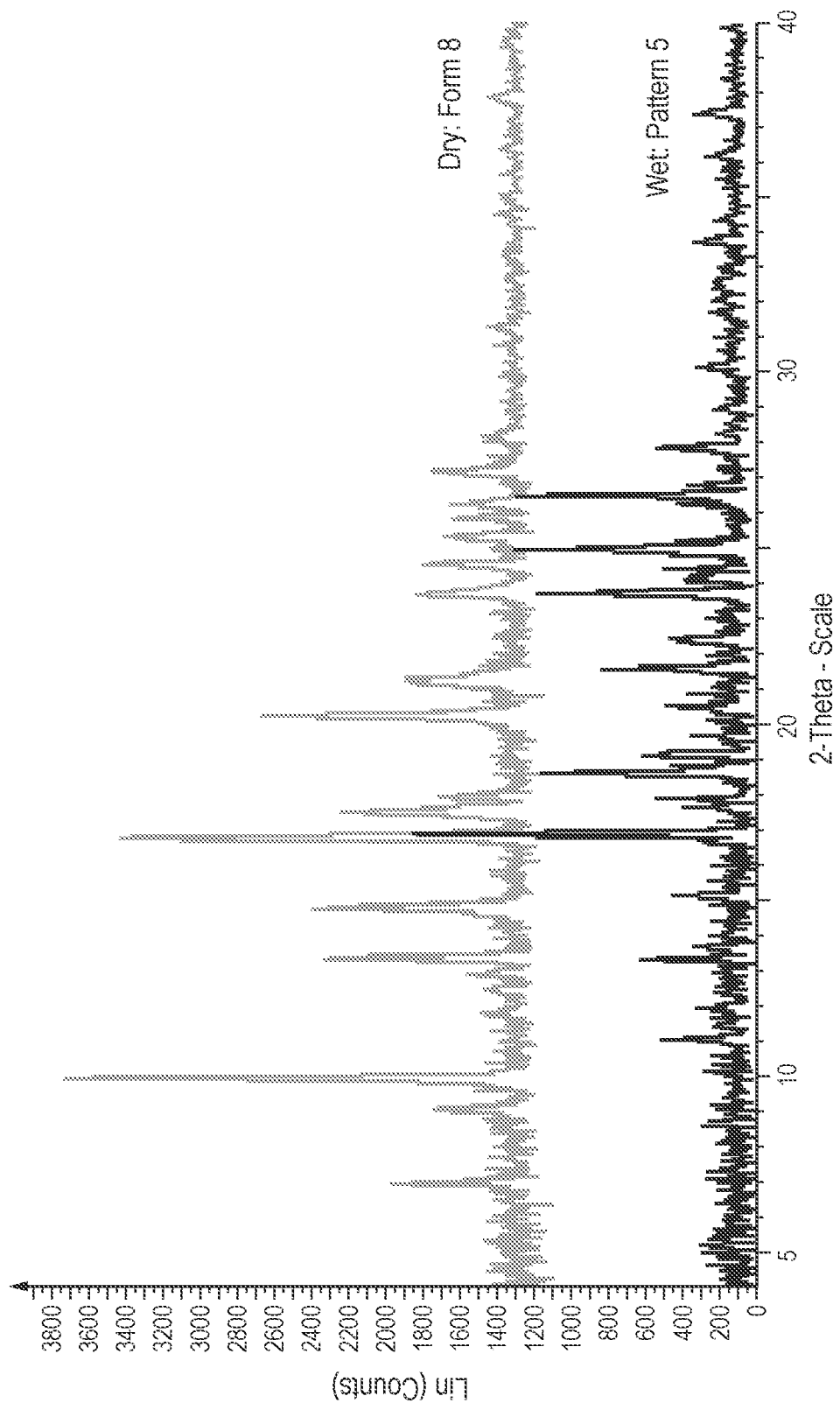
FIG. 13 shows exemplary XRPD patterns of Pattern 5 and Form 8.

In some embodiments, Form 8 exhibits an X-ray powder diffraction pattern substantially the same as depicted in FIG. 13 (top).

Figure 14:
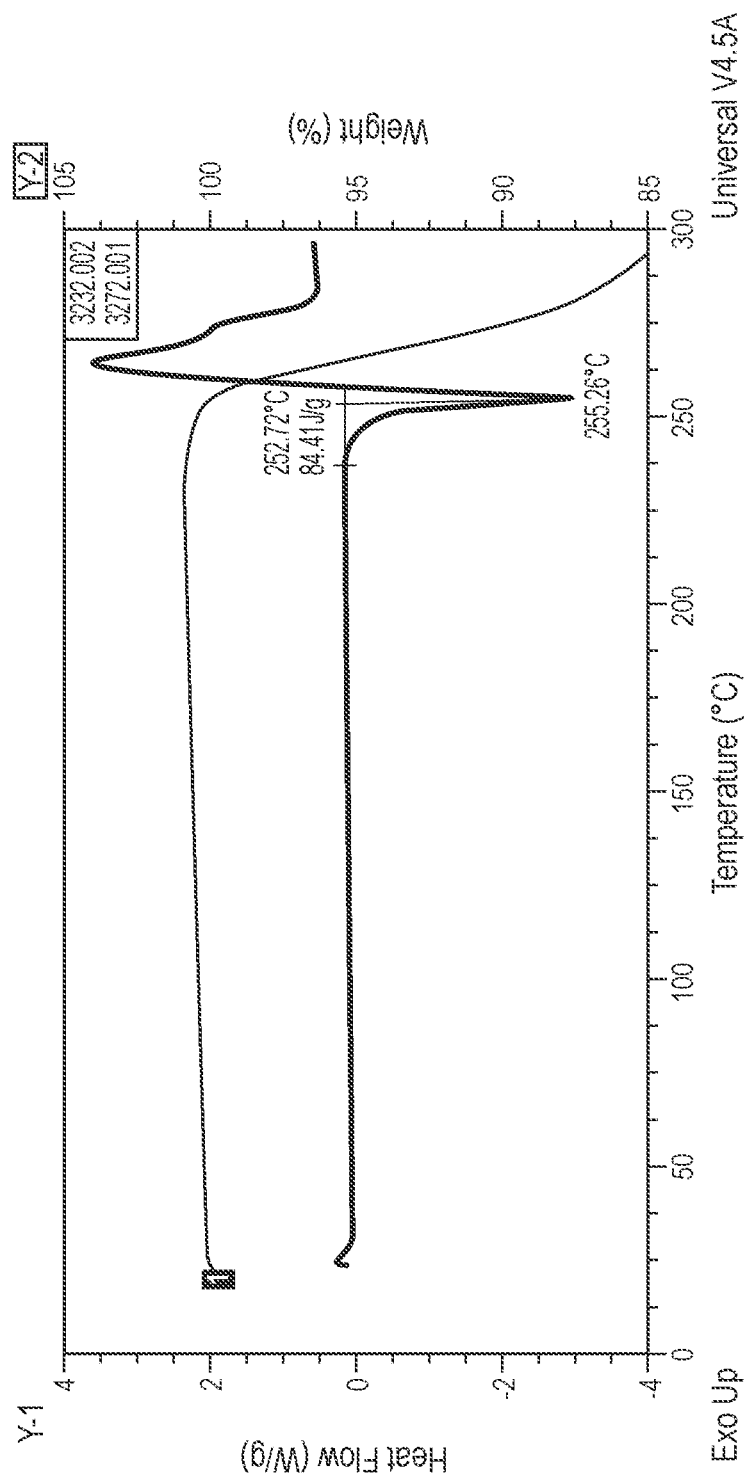
FIG. 14 shows an exemplary DSC and TGA overlay of Form 8.

In some embodiments, Form 8 has a differential scanning calorimetry curve substantially the same as shown in FIG. 14. In some embodiments, Form 8 exhibits an exotherm starting from about 252° C. based on differential scanning calorimetry.

In some embodiments, Form 8 has a dynamic vapor sorption plot substantially the same as shown in FIG. 3.

In some embodiments, Form 8 is an anhydrate.

In some embodiments, Form 8 comprises less than about 3.0% water. In some embodiments, Form 1 comprises less than about 2.0% water. In some embodiments, Form 1 comprises less than about 1.0% water. In some embodiments, Form 1 comprises less than about water.

Also provided herein is a method of preparing crystalline Form 8 of a compound of Formula II:

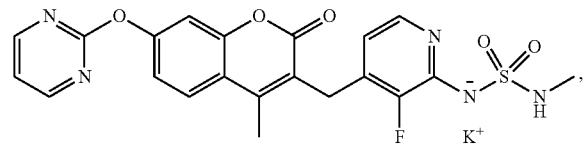

comprising: (i) contacting a compound of Formula II with DMSO to form a solution; (ii) adding acetone to the solution of step (i) to precipitate a solid; (iii) isolating the precipitated solid in step (ii); and (iv) drying the precipitated solid from step (iii), to give Form 8.

In some embodiments, the drying in step (iv) occurs under reduced pressure. In some embodiments, the drying in step (iv) occurs at a temperature of about 30 to about 50° C. In some embodiments, the drying in step (iv) occurs under reduced pressure at a temperature of about 30 to about 50° C.

In some embodiments, the isolating in step (iii) is by filtration or centrifugation.

Form 10

In another aspect, provided herein is crystalline Form 10 of a compound of Formula II:

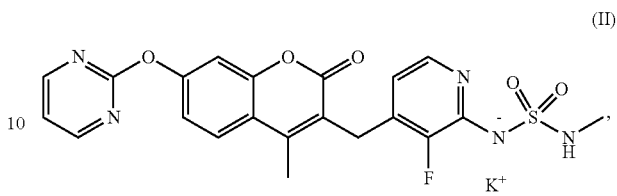

wherein Form 10 exhibits an X-ray power diffraction pattern comprising a characteristic XRPD peak at the following diffraction angle (2θ (degrees))=11.7±0.2, wherein the compound is a hydrate.

In some embodiments, Form 10 exhibits an X-ray powder diffraction pattern comprising peaks at the following diffraction angles (2θ (degrees))=11.7±0.2 and 25.5±0.2. In some embodiments, Form 10 exhibits an X-ray powder diffraction pattern comprising peaks at the following diffraction angles (2θ (degrees))=11.7±0.2 and 12.5±0.2. In some embodiments, Form 10 exhibits an X-ray powder diffraction pattern comprising peaks at the following diffraction angles (2θ (degrees))=11.7±0.2, 12.5±0.2, and 25.5±0.2. In some embodiments, Form 10 exhibits an X-ray powder diffraction pattern comprising peaks at the following diffraction angles (2θ (degrees))=11.7±0.2, 12.5±0.2, 24.4±0.2, and 25.5±0.2. In some embodiments, Form 10 exhibits an X-ray powder diffraction pattern comprising peaks at the following diffraction angles (2θ (degrees))=11.7±0.2, 12.5±0.2, 23.8±0.2, 24.4±0.2, and 25.5±0.2. In some embodiments, Form 10 exhibits an X-ray powder diffraction pattern further comprising at least one characteristic XRPD peak selected from diffraction angles (2θ (degrees))=12.0±0.2, 16.7±0.2, 17.0±0.2, 17.3±0.2, 17.9±0.2, 19.0±0.2, 19.4±0.2, and 20.7±0.2. In some embodiments, Form 10 exhibits an X-ray powder diffraction pattern further comprising at least one characteristic XRPD peak selected from diffraction angles (2θ (degrees))=5.1±0.2, 12.0±0.2, 13.7±0.2, 14.4±0.2, 15.3±0.2, 16.7±0.2, 17.0±0.2, 17.3±0.2, 17.9±0.2, 18.4±0.2, 19.0±0.2, 19.4±0.2, 20.7±0.2, 22.5±0.2, and 27.2±0.2. In some embodiments, Form 10 exhibits an X-ray powder diffraction pattern further comprising at least one characteristic XRPD peak selected from diffraction angles (2θ (degrees))=12.0±0.2, 16.7±0.2, 17.0±0.2, 17.3±0.2, 17.9±0.2, 19.0±0.2, 19.4±0.2, 20.7±0.2, 30.0±0.2, and 38.8±0.2. In some embodiments, Form 10 exhibits an X-ray powder diffraction pattern further comprising at least one characteristic XRPD peak selected from diffraction angles (2θ (degrees))=5.1±0.2, 10.4±0.2, 12.0±0.2, 13.7±0.2, 14.4±0.2, 15.3±0.2, 16.7±0.2, 17.0±0.2, 17.3±0.2, 17.9±0.2, 18.4±0.2, 19.0±0.2, 19.4±0.2, 22.5±0.2, 27.2±0.2, 30.0±0.2, 32.6±0.2, 38.2±0.2, and 38.8±0.2. In some embodiments, Form 10 exhibits an X-ray powder diffraction pattern comprising peaks at the following diffraction angles (2θ (degrees))=11.7±0.2, 12.0±0.2, 12.5±0.2, 16.7±0.2, 17.0±0.2, 17.3±0.2, 17.9±0.2, 19.0±0.2, 19.4±0.2, 20.7±0.2, 23.8±0.2, 24.4±0.2, 25.5±0.2, 30.0±0.2, and 38.8±0.2.

In another aspect, provided herein is crystalline Form 10 of a compound of Formula II:

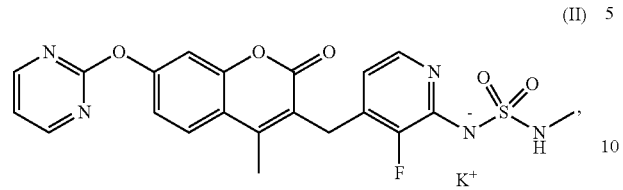

(II)

wherein Form 10 exhibits an X-ray power diffraction pattern comprising a characteristic XRPD peak at the following diffraction angle (2θ (degrees))=11.7±0.3, wherein the compound is a hydrate.

In some embodiments, Form 10 exhibits an X-ray powder diffraction pattern comprising peaks at the following diffraction angles (2θ (degrees))=11.7±0.3 and 25.5±0.3. In some embodiments, Form 10 exhibits an X-ray powder diffraction pattern comprising peaks at the following diffraction angles (2θ (degrees))=11.7±0.3 and 12.5±0.3. In some embodiments, Form 10 exhibits an X-ray powder diffraction pattern comprising peaks at the following diffraction angles (2θ (degrees))=11.7±0.3, 12.5±0.3, and 25.5±0.3. In some embodiments, Form 10 exhibits an X-ray powder diffraction pattern comprising peaks at the following diffraction angles (2θ (degrees))=11.7±0.3, 12.5±0.3, 24.4±0.3, and 25.5±0.3.

In some embodiments, Form 10 exhibits an X-ray powder diffraction pattern comprising peaks at the following diffraction angles (2θ (degrees))=11.7±0.3, 12.5±0.3, 23.8±0.3, 24.4±0.3, and 25.5±0.3. In some embodiments, Form 10 exhibits an X-ray powder diffraction pattern further comprising at least one characteristic XRPD peak selected from diffraction angles (2θ (degrees))=12.0±0.3, 16.7±0.3, 17.0±0.3, 17.3±0.3, 17.9±0.3, 19.0±0.3, 19.4±0.3, and 20.7±0.3. In some embodiments, Form 10 exhibits an X-ray powder diffraction pattern further comprising at least one characteristic XRPD peak selected from diffraction angles (2θ (degrees))=5.1±0.3, 10.4±0.3, 12.0±0.3, 13.7±0.3, 14.4±0.3, 15.3±0.3, 16.7±0.3, 17.0±0.3, 17.3±0.3, 17.9±0.3, 18.4±0.3, 19.0±0.3, 19.4±0.3, 20.7±0.3, 22.5±0.3, and 27.2±0.3. In some embodiments, Form 10 exhibits an X-ray powder diffraction pattern further comprising at least one characteristic XRPD peak selected from diffraction angles (2θ (degrees))=12.0±0.3, 16.7±0.3, 17.0±0.3, 17.3±0.3, 17.9±0.3, 19.0±0.3, 19.4±0.3, 20.7±0.3, 30.0±0.3, and 38.8±0.3. In some embodiments, Form 10 exhibits an X-ray powder diffraction pattern further comprising at least one characteristic XRPD peak selected from diffraction angles (2θ (degrees))=5.1±0.3, 12.0±0.3, 13.7±0.3, 14.4±0.3, 15.3±0.3, 16.7±0.3, 17.0±0.3, 17.3±0.3, 17.9±0.3, 18.4±0.3, 19.0±0.3, 19.4±0.3, 20.7±0.3, 22.5±0.3, 27.2±0.3, 30.0±0.3, 32.6±0.3, 38.2±0.3, and 38.8±0.3. In some embodiments, Form 10 exhibits an X-ray powder diffraction pattern comprising peaks at the following diffraction angles (2θ (degrees))=11.7±0.3, 12.0±0.3, 12.5±0.3, 16.7±0.3, 17.0±0.3, 17.3±0.3, 17.9±0.3, 19.0±0.3, 19.4±0.3, 20.7±0.3, 23.8±0.3, 24.4±0.3, 25.5±0.3, 30.0±0.3, and 38.8±0.3.

In some embodiments, also provided herein is crystalline Form 10 of a compound of Formula II:

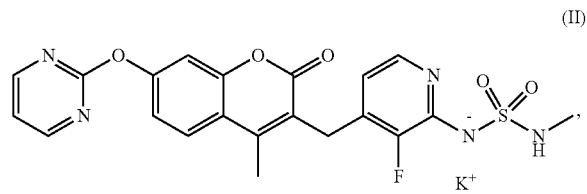 [SMILES: CNS(=O)(=O)Nc1nccc(Cc2c(C)c3ccc(Oc4ncccn4)cc3oc2=O)c1F ; [K+]]

(II)

wherein Form 10 exhibits an X-ray power diffraction pattern comprising a characteristic XRPD peak at the following diffraction angle (2θ (degrees))=11.7±0.5, wherein the compound is a hydrate.

In some embodiments, Form 10 exhibits an X-ray powder diffraction pattern comprising peaks at the following diffraction angles (2θ (degrees))=11.7±0.5 and 25.5±0.5. In some embodiments, Form 10 exhibits an X-ray powder diffraction pattern comprising peaks at the following diffraction angles (2θ (degrees))=11.7±0.5 and 12.5±0.5. In some embodiments, Form 10 exhibits an X-ray powder diffraction pattern comprising peaks at the following diffraction angles (2θ (degrees))=11.7±0.5, 12.5±0.5, and 25.5±0.5. In some embodiments, Form 10 exhibits an X-ray powder diffraction pattern comprising peaks at the following diffraction angles (2θ (degrees))=11.7±0.5, 12.5±0.5, 24.4±0.5, and 25.5±0.5.

In some embodiments, Form 10 exhibits an X-ray powder diffraction pattern comprising peaks at the following diffraction angles (2θ (degrees))=11.7±0.5, 12.5±0.5, 23.8±0.5, 24.4±0.5, and 25.5±0.5. In some embodiments, Form 10 exhibits an X-ray powder diffraction pattern further comprising at least one characteristic XRPD peak selected from diffraction angles (2θ (degrees))=12.0±0.5, 16.7±0.5, 17.0±0.5, 17.3±0.5, 17.9±0.5, 19.0±0.5, 19.4±0.5, and 20.7±0.5. In some embodiments, Form 10 exhibits an X-ray powder diffraction pattern further comprising at least one characteristic XRPD peak selected from diffraction angles (2θ (degrees))=5.1±0.5, 10.4±0.5, 12.0±0.5, 13.7±0.5, 14.4±0.5, 15.3±0.5, 16.7±0.5, 17.0±0.5, 17.3±0.5, 17.9±0.5, 18.4±0.5, 19.0±0.5, 19.4±0.5, 20.7±0.5, 22.5±0.5, and 27.2±0.5. In some embodiments, Form 10 exhibits an X-ray powder diffraction pattern further comprising at least one characteristic XRPD peak selected from diffraction angles (2θ (degrees))=12.0±0.5, 16.7±0.5, 17.0±0.5, 17.3±0.5, 17.9±0.5, 19.0±0.5, 19.4±0.5, 20.7±0.5, 30.0±0.5, and 38.8±0.5. In some embodiments, Form 10 exhibits an X-ray powder diffraction pattern further comprising at least one characteristic XRPD peak selected from diffraction angles (2θ (degrees))=5.1±0.5, 12.0±0.5, 13.7±0.5, 14.4±0.5, 15.3±0.5, 16.7±0.5, 17.0±0.5, 17.3±0.5, 17.9±0.5, 18.4±0.5, 19.0±0.5, 19.4±0.5, 20.7±0.5, 22.5±0.5, 27.2±0.5, 30.0±0.5, 32.6±0.5, 38.2±0.5, and 38.8±0.5. In some embodiments, Form 10 exhibits an X-ray powder diffraction pattern comprising peaks at the following diffraction angles (2θ (degrees))=11.7±0.5, 12.0±0.5, 12.5±0.5, 16.7±0.5, 17.0±0.5, 17.3±0.5, 17.9±0.5, 19.0±0.5, 19.4±0.5, 20.7±0.5, 23.8±0.5, 24.4±0.5, 25.5±0.5, 30.0±0.5, and 38.8±0.5.

Figure 7:
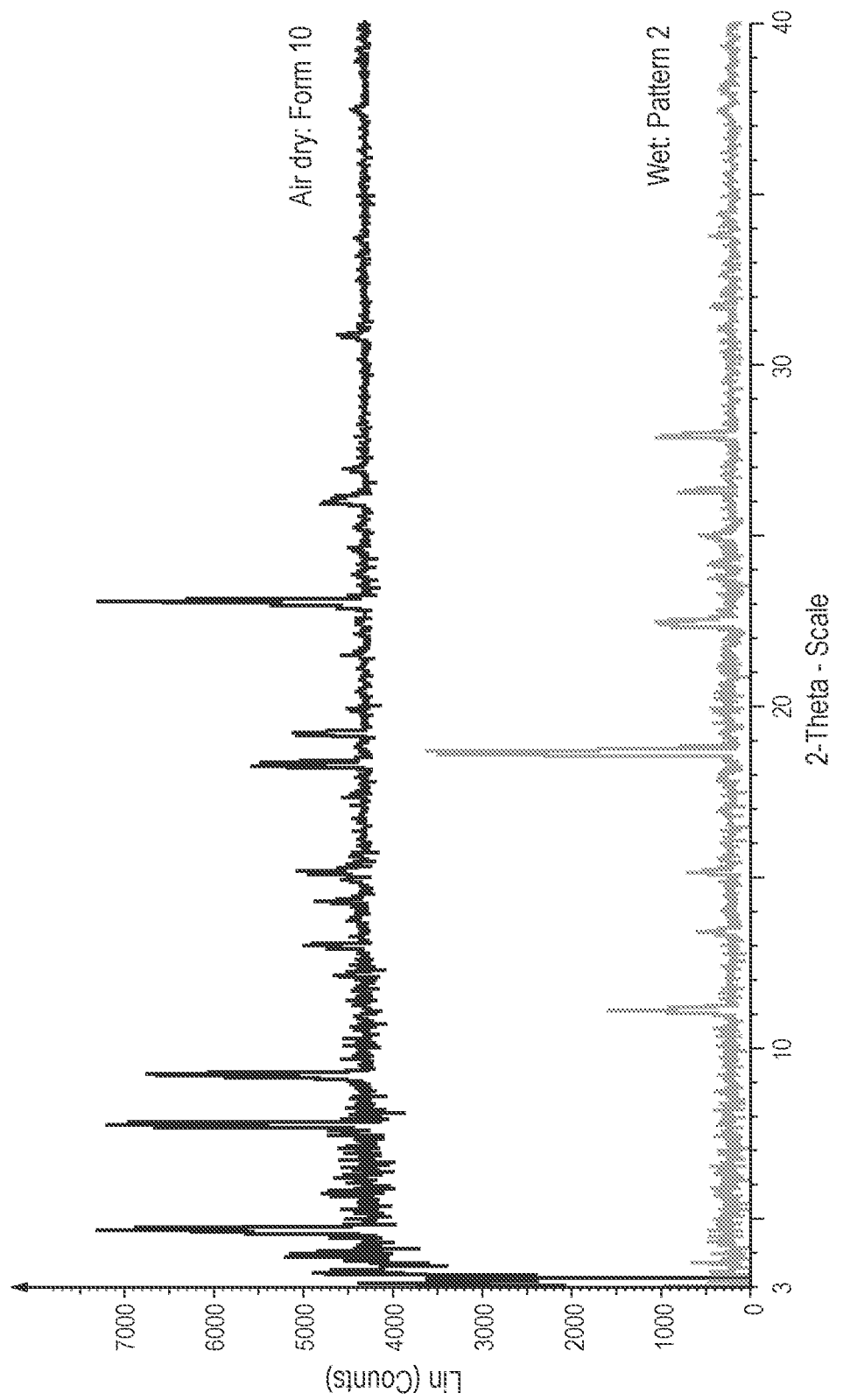
FIG. 7 shows exemplary XRPD patterns of Pattern 2 and Form 10.

In some embodiments, Form 10 exhibits an X-ray powder diffraction pattern substantially the same as depicted in FIG. 7 (top).

Figure 8:
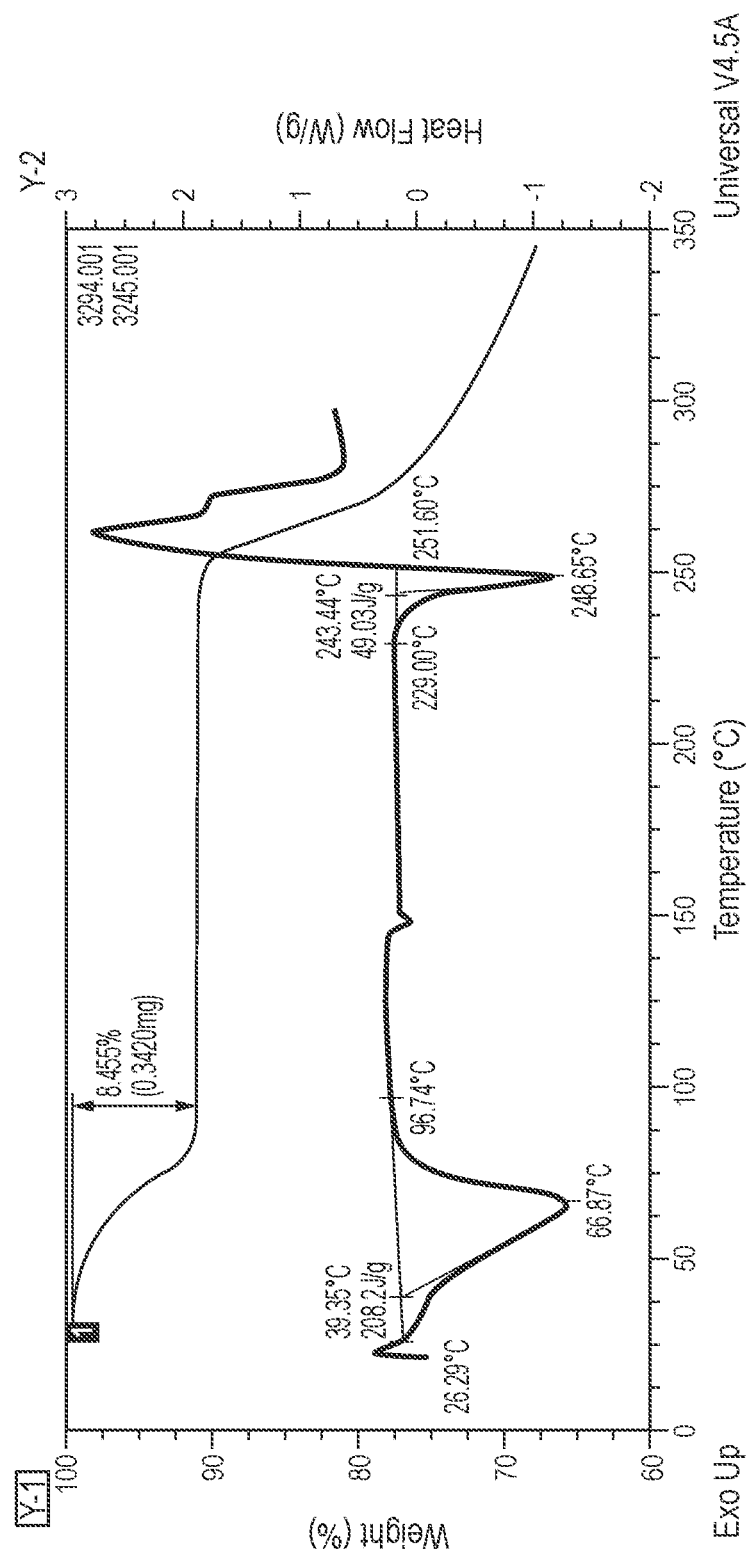
FIG. 8 shows an exemplary DSC and TGA overlay of Form 10.

In some embodiments, Form 10 has a differential scanning calorimetry curve substantially the same as shown in FIG. 8. In some embodiments, Form 10 exhibits endotherms starting from about 39° C. and about 243° C. based on differential scanning calorimetry.

Figure 10:
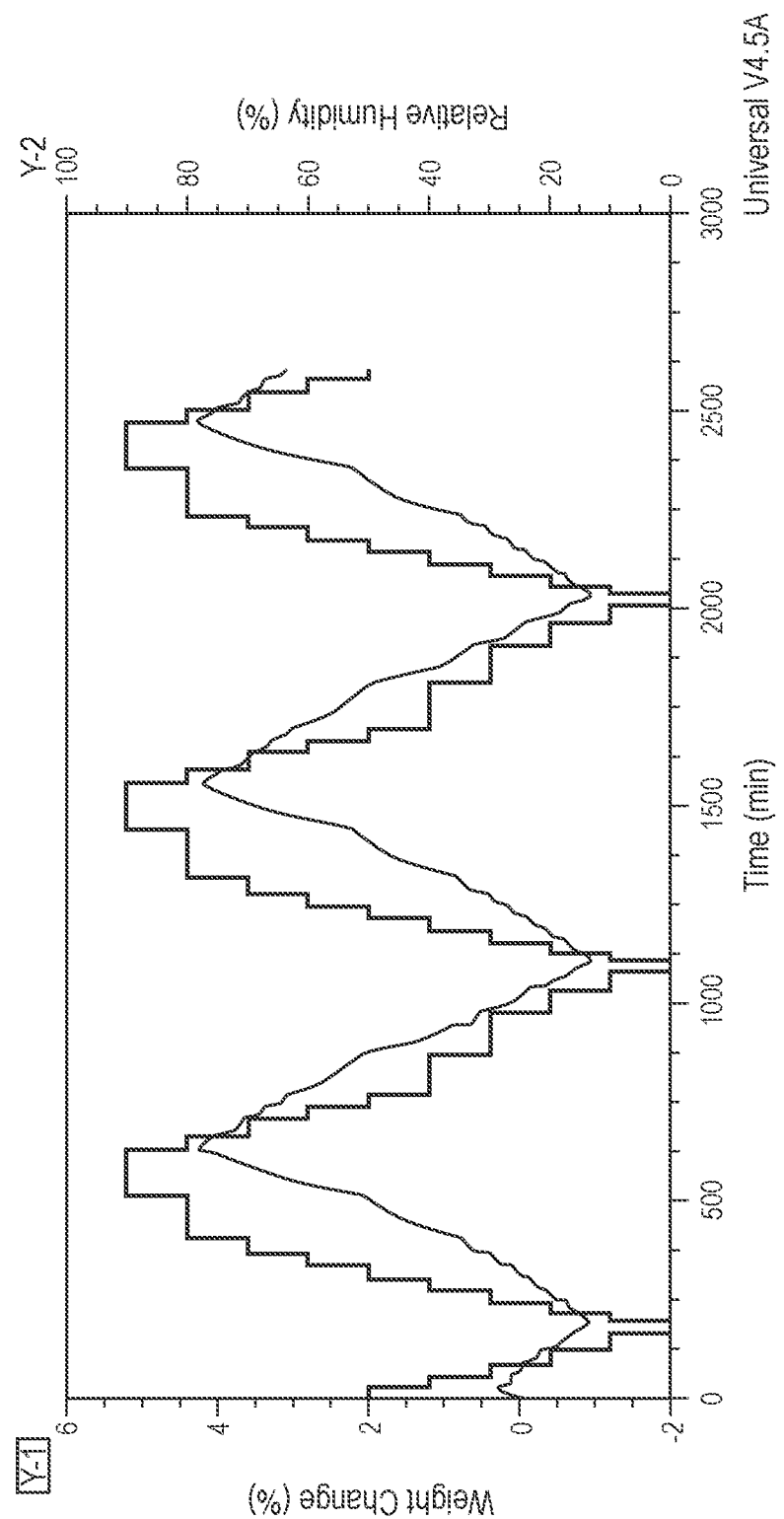
FIG. 10 shows an exemplary DVS pattern of Form 10.

In some embodiments, Form 10 has a dynamic vapor sorption plot substantially the same as shown in FIG. 10.

Also provided herein is a method of preparing crystalline Form 10 of a hydrate of a compound of Formula II:

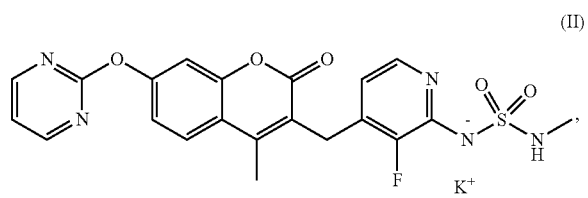 [SMILES: CNS(=O)(=O)Nc1nccc(Cc2c(C)c3ccc(Oc4ncccn4)cc3oc2=O)c1F ; [K+]]
(II)

comprising: (i) contacting a compound of Formula II with water to form a mixture; (ii) isolating a solid from the mixture of step (i); and (iii) drying the solid from step (ii), to give Form 10.

In some embodiments, the drying in step (iii) occurs under reduced pressure.

In some embodiments, the drying in step (iii) occurs at a ambient temperature.

In some embodiments, the isolating in step (ii) is by filtration or centrifugation.

Pattern 2

In another aspect, provided herein is crystalline Pattern 2 of a compound of Formula II:

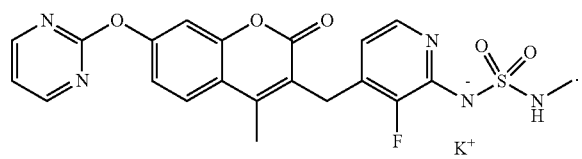
(II)

In some embodiments, Pattern 2 exhibits an X-ray powder diffraction pattern substantially the same as depicted in FIG. 7 (bottom).

Pattern 3

In another aspect, provided herein is crystalline Pattern 3 of a compound of Formula II:

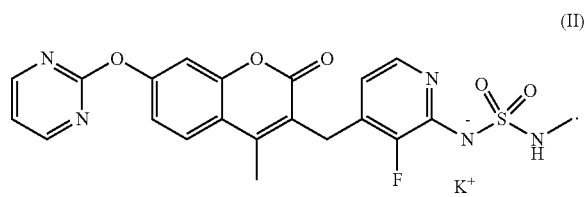 [SMILES: CNS(=O)(=O)Nc1nccc(Cc2c(C)c3ccc(Oc4ncccn4)cc3oc2=O)c1F ; [K+]]
(II)

Figure 12A:
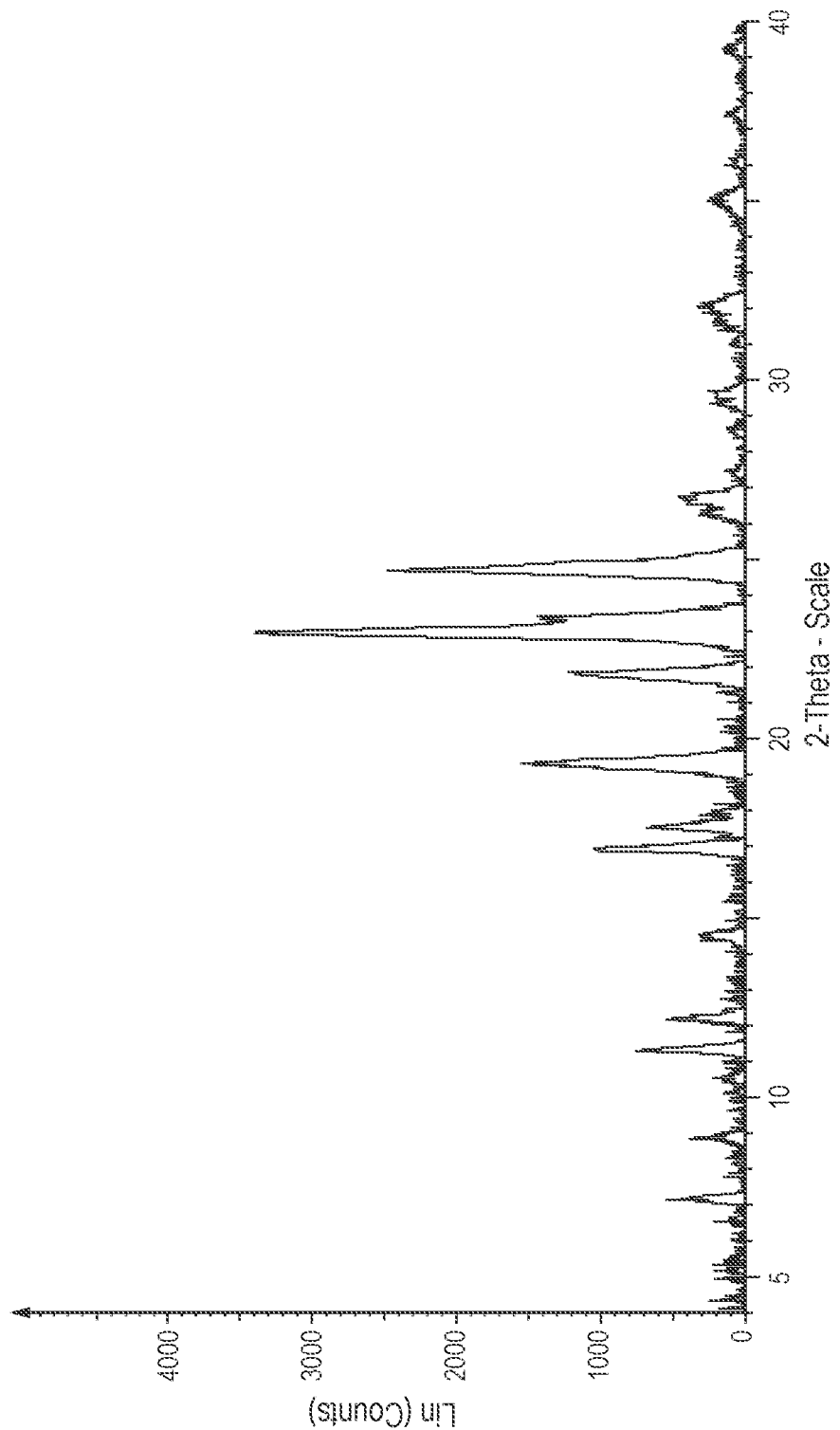
FIG. 12A shows an exemplary XRPD pattern of Pattern 4.
Figure 12B:
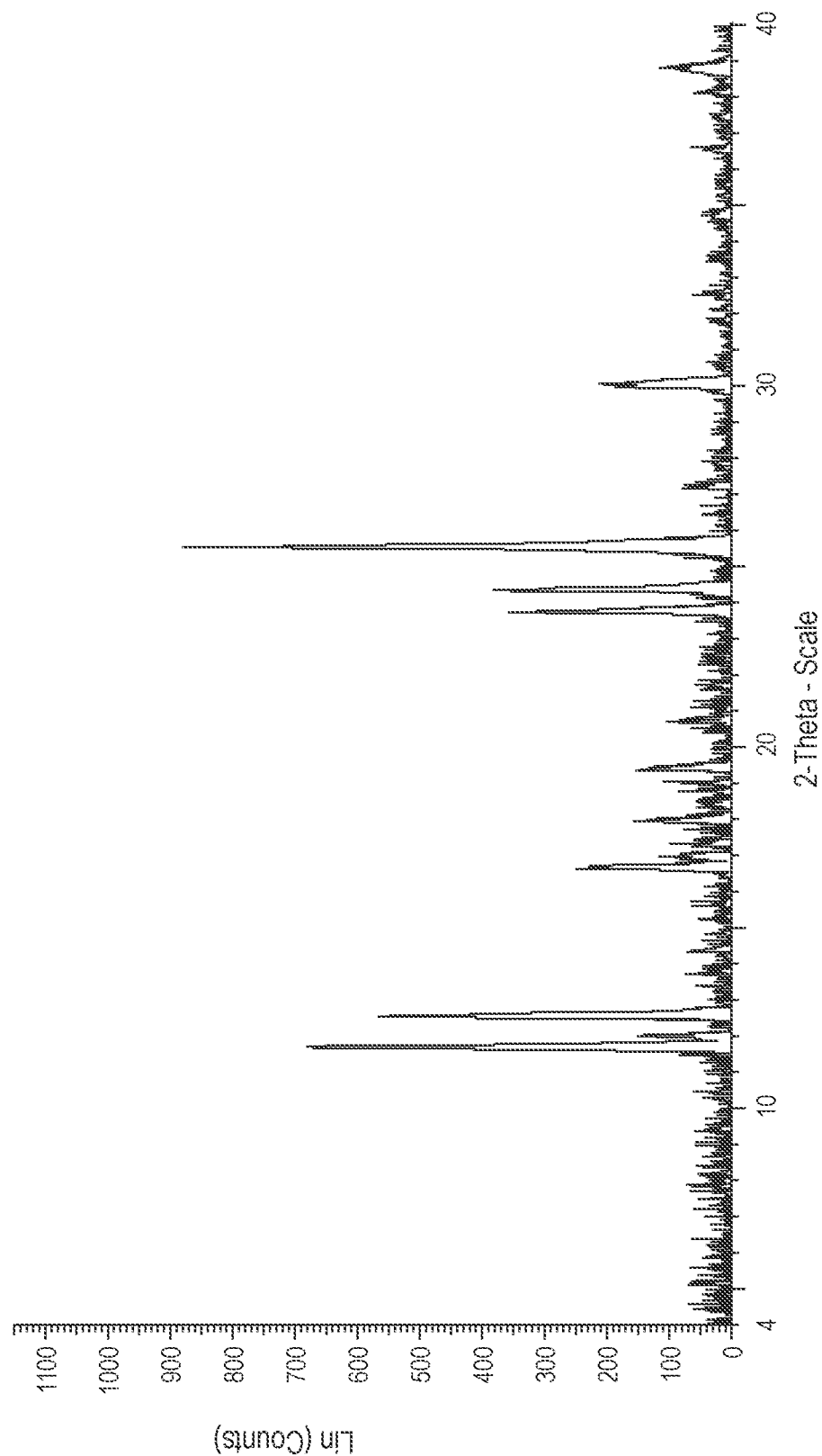
FIG. 12B shows an exemplary XRPD pattern of Pattern 3.

In some embodiments, Pattern 3 exhibits an X-ray powder diffraction pattern substantially the same as depicted in FIG. 12B.

Pattern 5

In another aspect, provided herein is crystalline Pattern 5 of a compound of Formula II:

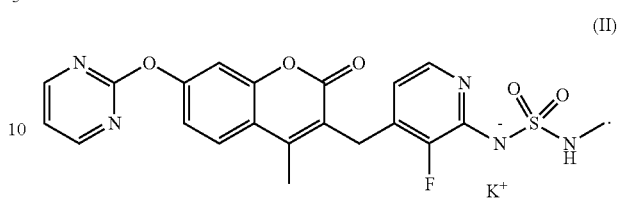
(II)

In some embodiments, Pattern 5 exhibits an X-ray powder diffraction pattern substantially the same as depicted in FIG. 13 (bottom).

Pattern 6

In another aspect, provided herein is crystalline Pattern 6 of a compound of Formula II:

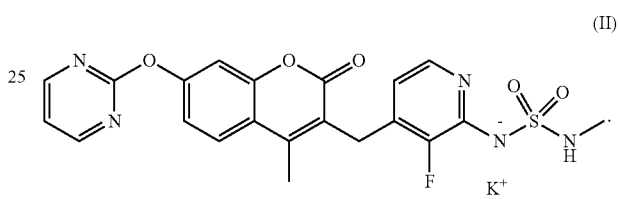
(II)

Figure 19:
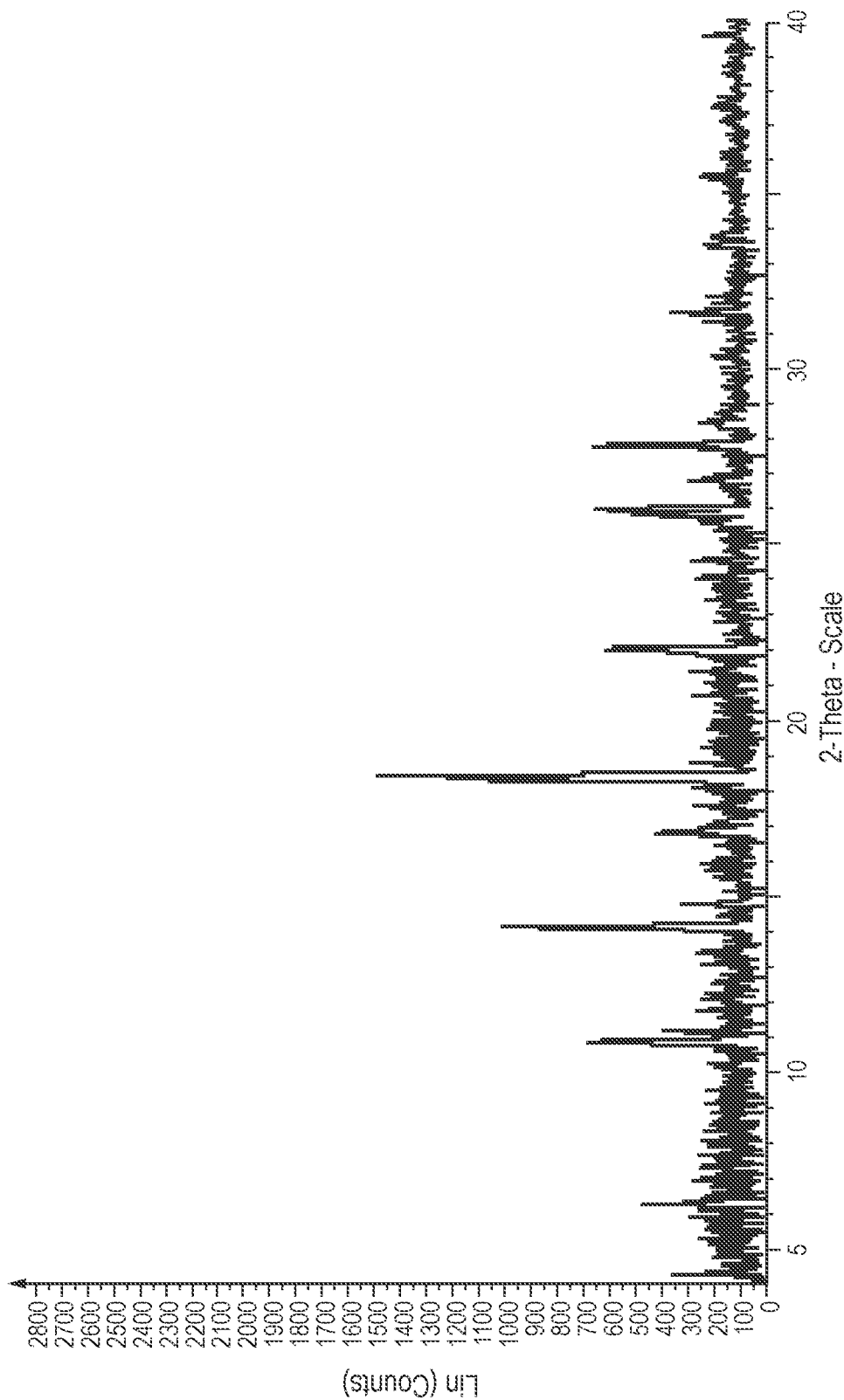
FIG. 19 shows an exemplary XRPD pattern of Pattern 6.

In some embodiments, Pattern 6 exhibits an X-ray powder diffraction pattern substantially the same as depicted in FIG. 19.

Pattern 7

In another aspect, provided herein is crystalline Pattern 7 of a compound of Formula II:

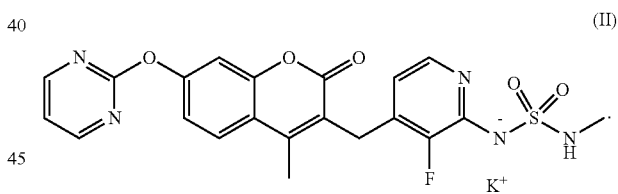
(II)

Figure 20:
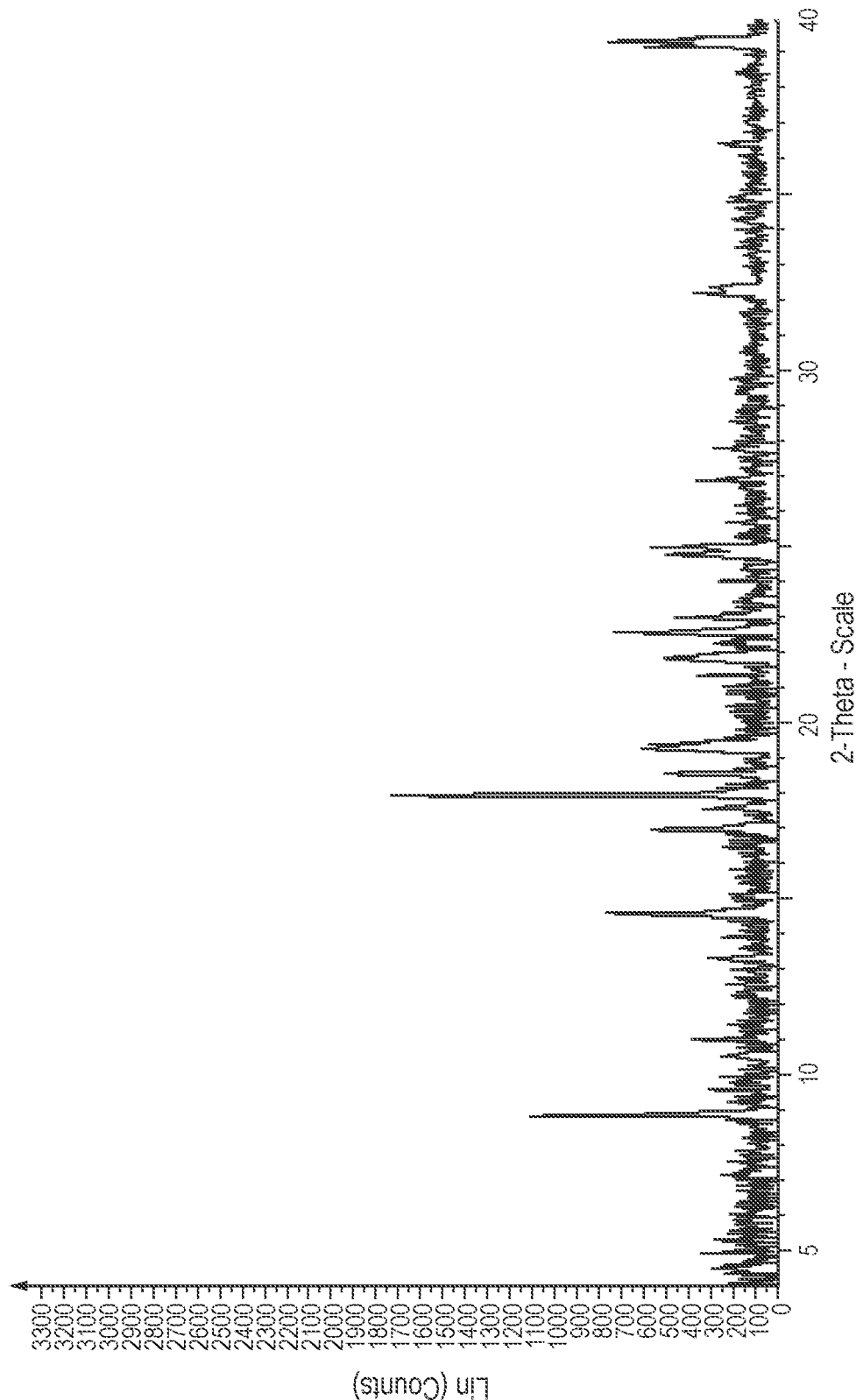
FIG. 20 shows an exemplary XRPD pattern of Pattern 7.

In some embodiments, Pattern 7 exhibits an X-ray powder diffraction pattern substantially the same as depicted in FIG. 20.

Pattern 9

In another aspect, provided herein is crystalline Pattern 9 of a compound of Formula II:

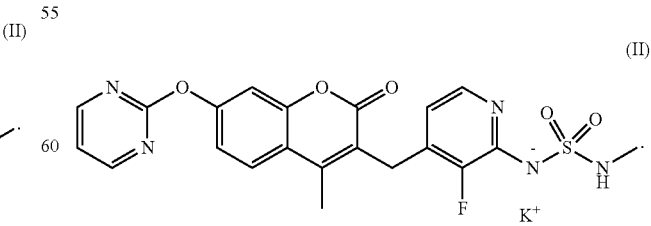
(II)

Figure 21:
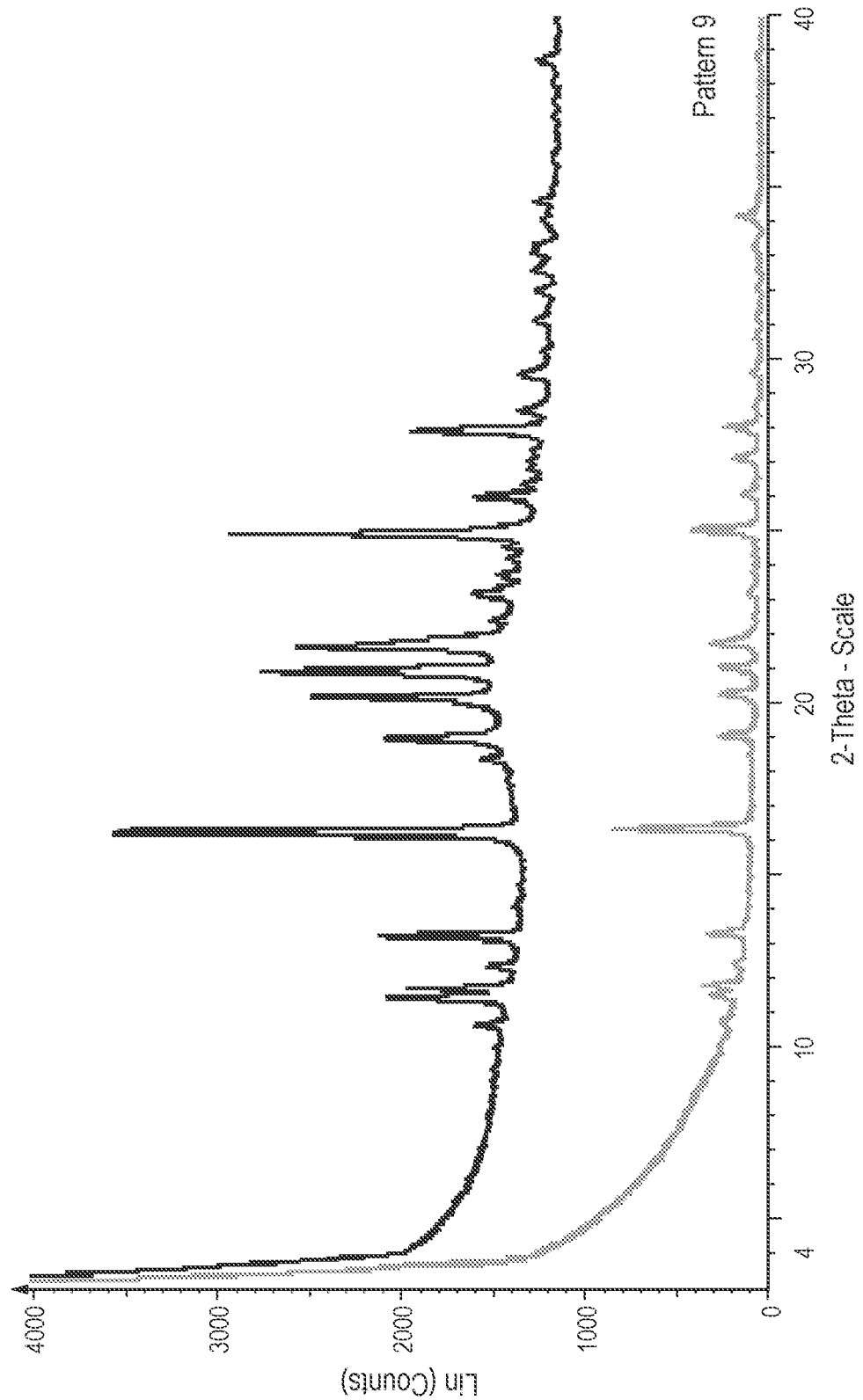
FIG. 21 shows an exemplary XRPD pattern of Pattern 9.

In some embodiments, Pattern 9 exhibits an X-ray powder diffraction pattern substantially the same as depicted in FIG. 21.

Pattern 11

In another aspect, provided herein is crystalline Pattern 11 of a compound of Formula II:

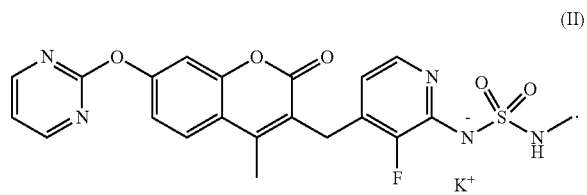 [SMILES: CNS(=O)(=O)Nc1nccc(Cc2c(C)c3ccc(Oc4ncccn4)cc3oc2=O)c1F ; [K+]]

(II)

Figure 23:
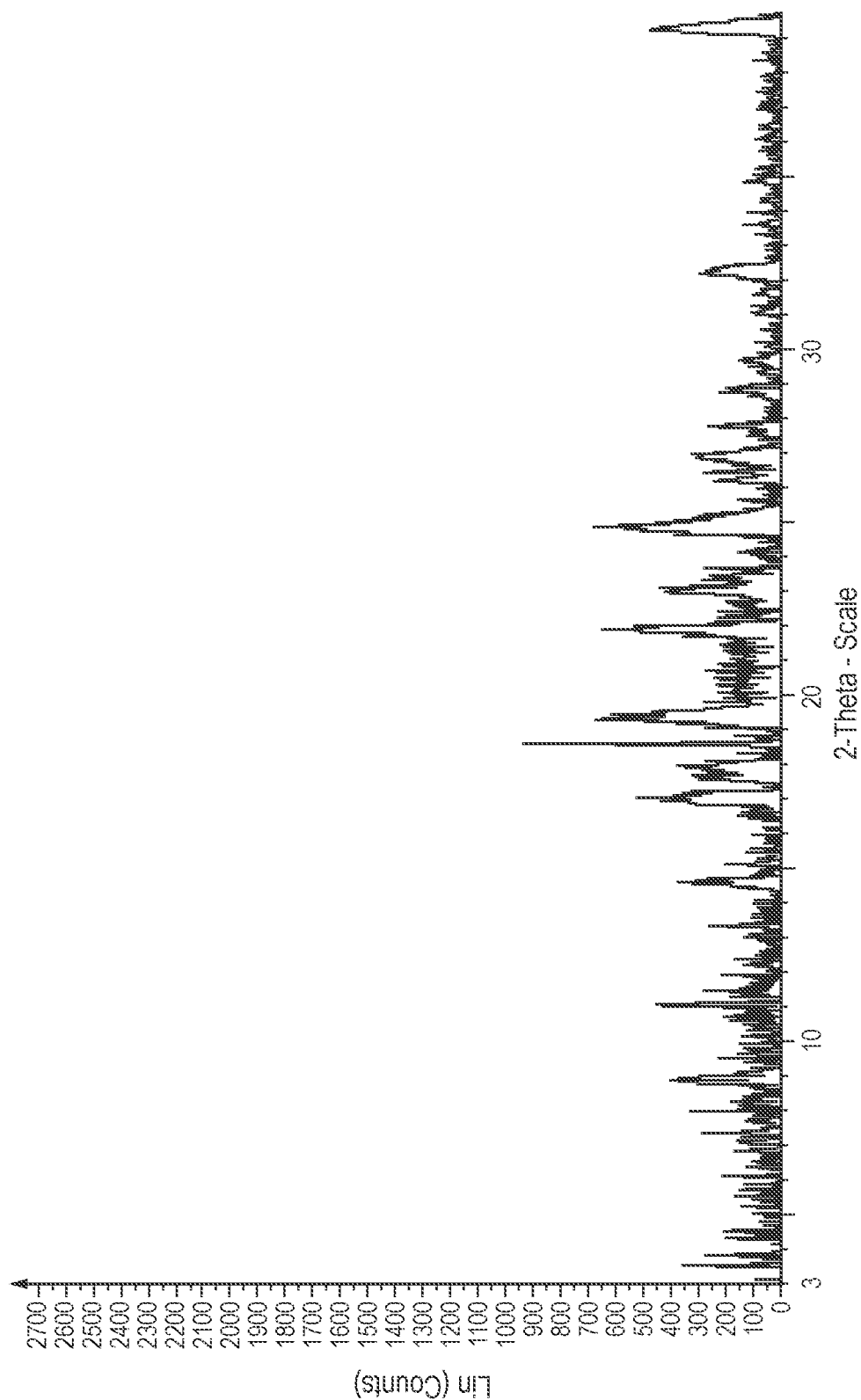
FIG. 23 shows an exemplary XRPD pattern of Pattern 11.

In some embodiments, Pattern 11 exhibits an X-ray powder diffraction pattern substantially the same as depicted in FIG. 23.

Pattern 12

In another aspect, provided herein is crystalline Pattern 12 of a compound of Formula II:

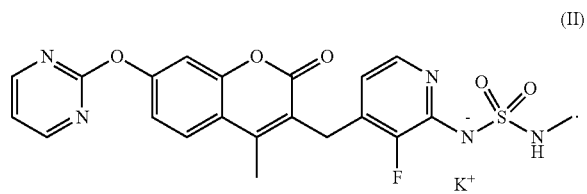 [SMILES: CNS(=O)(=O)Nc1nccc(Cc2c(C)c3ccc(Oc4ncccn4)cc3oc2=O)c1F ; [K+]]

(II)

Figure 24:
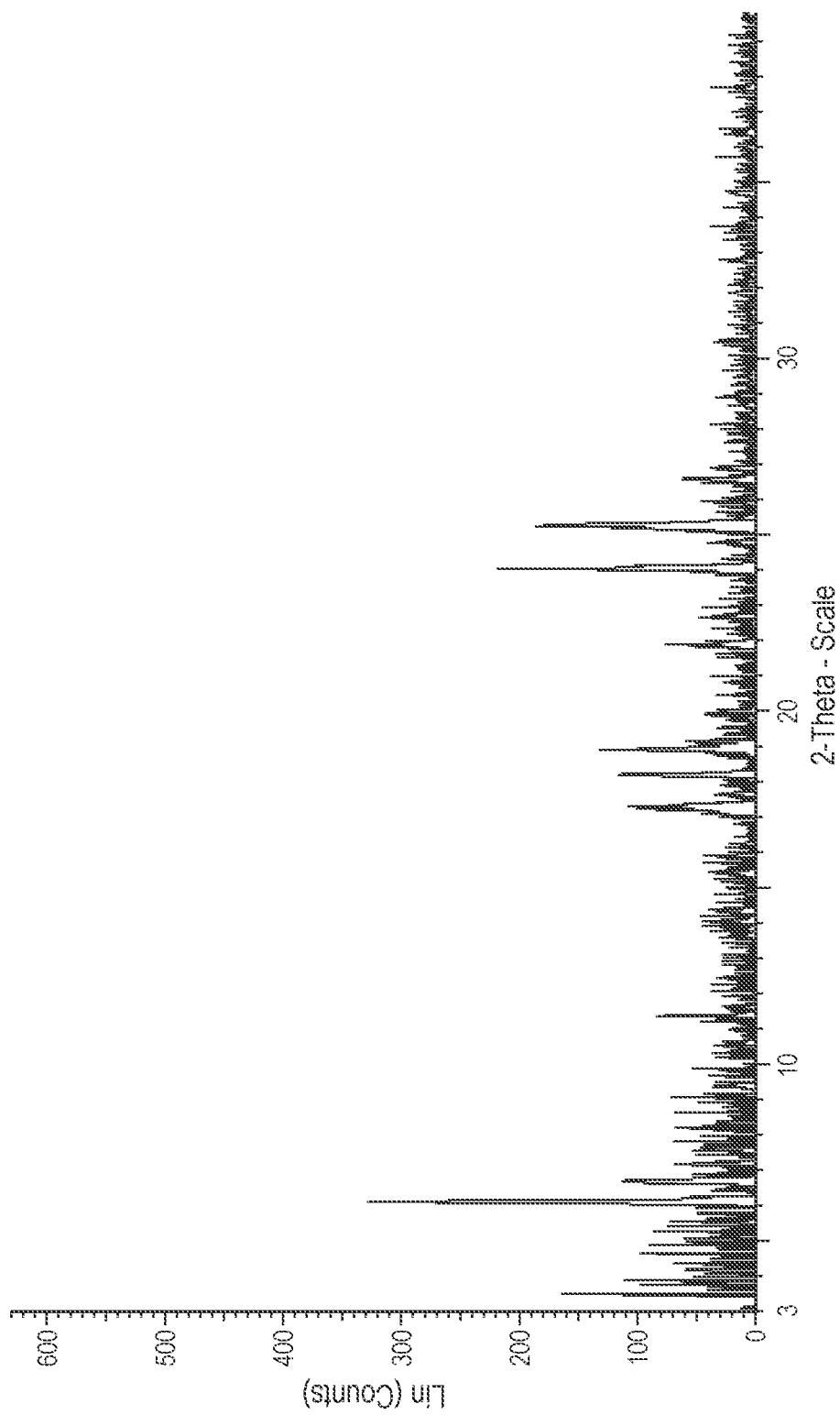
FIG. 24 shows an exemplary XRPD pattern of Pattern 12.

In some embodiments, Pattern 12 exhibits an X-ray powder diffraction pattern substantially the same as depicted in FIG. 24.

Doses and Administration

In some embodiments, the solid form of a compound of Formula II disclosed herein is dosed at least once a week (e.g., once a week, twice a week, three times a week, four times a week, five times a week, or six times a week). In some embodiments, solid form of a compound of Formula II disclosed herein is dosed once a week. In some embodiments, the solid form of a compound of Formula II disclosed herein is dosed twice a week. In some embodiments, the solid form of a compound of Formula II disclosed herein is dosed three times a week.

In some embodiments, the solid form of a compound of Formula II disclosed herein is dosed at about 0.1 mg to about 100 mg (based on free form), e.g., about 0.1 mg to about mg, about 0.1 mg to about 10 mg, about 0.1 mg to about 5 mg, about 0.1 mg to about 4 mg, about 0.1 mg to about 3 mg, about 0.1 mg to about 2 mg, about 0.1 mg to about 1 mg, about 1 mg to about 5 mg, about 1 mg to about 10 mg, about 1 mg to about 20 mg, about 1 mg to about mg, about 1 mg to about 60 mg, about 1 mg to about 80 mg, about 1 mg to about 100 mg, about 10 mg to about 100 mg, about 20 mg to about 100 mg, about 40 mg to about 100 mg, about 60 mg to about 100 mg, or about 80 mg to about 100 mg. In some embodiments, the solid form of a compound of Formula II disclosed herein is dosed at about 0.5 mg to about 10 mg (based on free form) per administration. In some embodiments, the solid form of a compound of Formula II disclosed herein is dosed at about 0.8 mg to about 10 mg (based on free form) per administration. In some embodiments, the solid form of a compound of Formula II disclosed herein is dosed at about 1 mg to about 5 mg (based on free form) per administration. In some embodiments, the solid form of a compound of Formula II disclosed herein is dosed at about 2 mg to about 4 mg (based on free form) per administration. In some embodiments, the solid form of a compound of Formula II disclosed herein is dosed at about 0.1 mg, 0.2 mg, 0.5 mg, 1 mg, 1.5 mg, 3 mg, 4 mg, 5 mg, 10 mg, 15 mg, 20 mg, 25 mg, 30 mg, 35 mg, 40 mg, 45 mg, 50 mg, mg, 70 mg, 75 mg, 80 mg, 85 mg, 90 mg, 95 mg, or 100 mg (based on free form) per administration. In some embodiments, the solid form of a compound of Formula II is dosed at about 4 mg (based on free form) per administration. In some embodiments, the solid form of a compound of Formula II disclosed herein is dosed at about 3.2 mg (based on free form) per administration. In some embodiments, the solid form of a compound of Formula II disclosed herein is administered orally.

In some embodiments, the solid form of a compound of Formula II disclosed herein is dosed as a cycle. In some embodiments, the cycle comprises administering the solid form of a compound of Formula II disclosed herein for three weeks and then not administering the solid form of a compound of Formula II disclosed herein for one week. In some embodiments, the solid form of a compound of Formula II disclosed herein is dosed once a week. In some embodiments, the solid form of a compound of Formula II disclosed herein is dosed twice a week. In some embodiments, the solid form of a compound of Formula II disclosed herein is dosed three times a week. In some embodiments, the solid form of a compound of Formula II disclosed herein is dosed at about 0.8 mg to about 10 mg (based on free form) per administration. In some embodiments, the solid form of a compound of Formula II disclosed herein is dosed at about 1 mg to about 5 mg (based on free form) per administration. In some embodiments, the solid form of a compound of Formula II disclosed herein is dosed at about 2 mg to about 4 mg (based on free form) per administration. In some embodiments, the solid form of a compound of Formula II is dosed at about 4 mg (based on free form) per administration. In some embodiments, the solid form of a compound of Formula II disclosed herein is dosed at about 3.2 mg (based on free form) per administration.

In some embodiments, the solid form of a compound of Formula II disclosed herein is dosed twice a week as a cycle, wherein the cycle comprises administering the solid form of a compound of Formula II disclosed herein for three weeks at a dose of about 0.8 mg to about 10 mg (based on free form) per administration and then not administering the solid form of a compound of Formula II disclosed herein for one week. In some embodiments, the solid form of a compound of Formula II disclosed herein is dosed twice a week as a cycle, wherein the cycle comprises administering the solid form of a compound of Formula II disclosed herein for three weeks at a dose of about 1 mg to about 5 mg (based on free form) per administration and then not administering the solid form of a compound of Formula II disclosed herein for one week. In some embodiments, the solid form of a compound of Formula II disclosed herein is dosed twice a week as a cycle, wherein the cycle comprises administering the solid form of a compound of Formula II disclosed herein for three weeks at a dose of about 2 mg to about 4 mg (based on free form) per administration and then not administering the solid form of a compound of Formula II disclosed herein for one week. In some embodiments, the solid form of a compound of Formula II disclosed herein is dosed twice a week as a cycle, wherein the cycle comprises administering the solid form of a compound of Formula II disclosed herein for three weeks at a dose of 3.2 mg (based on free form) per administration and then not administering the solid form of a compound of Formula II disclosed herein for one week. In some embodiments, the solid form of a compound of Formula II disclosed herein is dosed twice a week as a cycle, wherein the cycle comprises administering the solid form of a compound of Formula II disclosed herein for three weeks at a dose of 4 mg (based on free form) per administration and then not administering the solid form of a compound of Formula II disclosed herein for one week. In some embodiments, the cycle is repeated at least once.

In some embodiments, the solid form of a compound of Formula II disclosed herein is dosed thrice a week as a cycle, wherein the cycle comprises administering the solid form of a compound of Formula II disclosed herein for three weeks at a dose of about 0.8 mg to about 10 mg (based on free form) per administration and then not administering the solid form of a compound of Formula II disclosed herein for one week. In some embodiments, the solid form of a compound of Formula II disclosed herein is dosed thrice a week as a cycle, wherein the cycle comprises administering the solid form of a compound of Formula II disclosed herein for three weeks at a dose of about 1 mg to about 5 mg (based on free form) per administration and then not administering the solid form of a compound of Formula II disclosed herein for one week. In some embodiments, the solid form of a compound of Formula II disclosed herein is dosed thrice a week as a cycle, wherein the cycle comprises administering the solid form of a compound of Formula II disclosed herein for three weeks at a dose of about 2 mg to about 4 mg (based on free form) per administration and then not administering the solid form of a compound of Formula II disclosed herein for one week. In some embodiments, the solid form of a compound of Formula II disclosed herein is dosed thrice a week as a cycle, wherein the cycle comprises administering the solid form of a compound of Formula II disclosed herein for three weeks at a dose of 3.2 mg (based on free form) per administration and then not administering the solid form of a compound of Formula II disclosed herein for one week. In some embodiments, the solid form of a compound of Formula II disclosed herein is dosed thrice a week as a cycle, wherein the cycle comprises administering the solid form of a compound of Formula II disclosed herein for three weeks at a dose of 4 mg (based on free form) per administration and then not administering the solid form of a compound of Formula II disclosed herein for one week. In some embodiments, the cycle is repeated at least once.

In some embodiments, Form 1 is dosed at about 0.1 mg to about 100 mg, e.g., about 0.1 mg to about 50 mg, about 0.1 mg to about 10 mg, about 0.1 mg to about 5 mg, about mg to about 4 mg, about 0.1 mg to about 3 mg, about 0.1 mg to about 2 mg, about 0.1 mg to about 1 mg, about 1 mg to about 5 mg, about 1 mg to about 10 mg, about 1 mg to about 20 mg, about 1 mg to about 40 mg, about 1 mg to about 60 mg, about 1 mg to about 80 mg, about 1 mg to about 100 mg, about 10 mg to about 100 mg, about 20 mg to about 100 mg, about 40 mg to about 100 mg, about 60 mg to about 100 mg, or about 80 mg to about 100 mg, per administration. In some embodiments, Form 1 is dosed at about 0.5 mg to about 10 mg per administration. In some embodiments, Form 1 is dosed at about 0.8 mg to about 10 mg per administration. In some embodiments, Form 1 is dosed at about 1 mg to about 5 mg per administration. In some embodiments, Form 1 is dosed at about 2 mg to about 4 mg per administration. In some embodiments, Form 1 is dosed at about 0.1 mg, 0.2 mg, 0.5 mg, 1 mg, 1.5 mg, 3 mg, 4 mg, 5 mg, 10 mg, 15 mg, 20 mg, 25 mg, 30 mg, 35 mg, 40 mg, 45 mg, 50 mg, mg, 70 mg, 75 mg, 80 mg, 85 mg, 90 mg, 95 mg, or 100 mg per administration. In some embodiments, Form 1 is dosed at about 4.3 mg per administration. In some embodiments, Form 1 is dosed at about 3.5 mg per administration. In some embodiments, Form 1 is administered orally.

In some embodiments, Form 8 is dosed at about 0.1 mg to about 100 mg, e.g., about 0.1 mg to about 50 mg, about 0.1 mg to about 10 mg, about 0.1 mg to about 5 mg, about mg to about 4 mg, about 0.1 mg to about 3 mg, about 0.1 mg to about 2 mg, about 0.1 mg to about 1 mg, about 1 mg to about 5 mg, about 1 mg to about 10 mg, about 1 mg to about 20 mg, about 1 mg to about 40 mg, about 1 mg to about 60 mg, about 1 mg to about 80 mg, about 1 mg to about 100 mg, about 10 mg to about 100 mg, about 20 mg to about 100 mg, about 40 mg to about 100 mg, about 60 mg to about 100 mg, or about 80 mg to about 100 mg, per administration. In some embodiments, Form 8 is dosed at about 0.5 mg to about 10 mg per administration. In some embodiments, Form 8 is dosed at about 0.8 mg to about 10 mg per administration. In some embodiments, Form 8 is dosed at about 1 mg to about 5 mg per administration. In some embodiments, Form 8 is dosed at about 2 mg to about 4 mg per administration. In some embodiments, Form 8 is dosed at about 0.1 mg, 0.2 mg, 0.5 mg, 1 mg, 1.5 mg, 3 mg, 4 mg, 5 mg, 10 mg, 15 mg, 20 mg, 25 mg, 30 mg, 35 mg, 40 mg, 45 mg, 50 mg, mg, 70 mg, 75 mg, 80 mg, 85 mg, 90 mg, 95 mg, or 100 mg per administration. In some embodiments, Form 8 is dosed at about 4.3 mg per administration. In some embodiments, Form 8 is dosed at about 3.5 mg per administration. In some embodiments, Form 8 is administered orally.

In alternative embodiments, the solid form of a compound of Formula II disclosed herein is dosed continuously (i.e., without a period of time, e.g., one week, wherein the solid form of a compound of Formula II disclosed herein is not administered). In some embodiments, the solid form of a compound of Formula II disclosed herein is dosed once a week. In some embodiments, the solid form of a compound of Formula II disclosed herein is dosed twice a week. In some embodiments, the solid form of a compound of Formula II disclosed herein is dosed three times a week.

Pharmaceutical Compositions and Dosage Forms

In an aspect, provided herein is a pharmaceutical composition comprising a solid form of a compound of Formula II disclosed herein and a pharmaceutically acceptable carrier.

In some embodiments, the pharmaceutical composition is suitable for oral administration. In some embodiments the pharmaceutical composition is orally administered in any orally acceptable dosage form including, but not limited to, liqui-gel tablets or capsules, syrups, emulsions and aqueous suspensions. Liqui-gels may include gelatins, plasticizers, or opacifiers, or a combination thereof, as needed to achieve a suitable consistency and may be coated with enteric coatings that are approved for use, e.g., shellacs. Additional thickening agents, for example gums, e.g., xanthan gum, starches, e.g., corn starch, or glutens may be added to achieve a desired consistency of the pharmaceutical composition when used as an oral dosage. If desired, certain sweetening, flavoring, or coloring agents, or a combination thereof, may be added.

In some embodiments, the subject is administered the pharmaceutical composition in a form suitable for oral administration such as a tablet, capsule, pill, powder, sustained release formulations, extended release formulations, delayed release formulations, solution, and suspension. The pharmaceutical composition may be in unit dosage forms suitable for single administration of precise dosages.

For oral administration, the active ingredients, e.g., the solid form of a compound of Formula II disclosed herein can be formulated readily by combining the active ingredients with pharmaceutically acceptable carriers well known in the art. Such carriers enable the active ingredients of the invention to be formulated as tablets, pills, capsules, liquids, gels, syrups, slurries, powders or granules, suspensions or solutions in water or non-aqueous media, and the like, for oral ingestion by a subject. Pharmacological preparations for oral use can be made using a solid excipient, optionally grinding the resulting mixture, and processing the mixture of granules, after adding suitable auxiliaries if desired, to obtain, for example, tablets. Suitable excipients such as diluents, binders or disintegrants may be desirable.

Oral dosage forms may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In an aspect, provided herein is an oral dosage form comprising (a) an effective amount of crystalline Form 1 of a compound of Formula II, wherein Form 1 exhibits an X-ray power diffraction pattern comprising a characteristic XRPD peak at the following diffraction angle (2θ (degrees))=9.0±0.2; and (b) at least one pharmaceutically acceptable carrier. In some embodiments, Form 1 exhibits an X-ray power diffraction pattern comprising peaks at the following diffraction angles (2θ (degrees)) 4.5±0.2, and 9.0±0.2. In some embodiments, Form 1 exhibits an X-ray power diffraction pattern comprising peaks at the following diffraction angles (2θ (degrees)) 4.5±0.2, 9.0±0.2, and 18.1±0.2.

In some embodiments, provided herein is an oral dosage form comprising (a) an effective amount of crystalline Form 1 of a compound of Formula II, wherein Form 1 exhibits an X-ray power diffraction pattern comprising a characteristic XRPD peak at the following diffraction angle (2θ (degrees))=9.0±0.3; and (b) at least one pharmaceutically acceptable carrier. In some embodiments, Form 1 exhibits an X-ray power diffraction pattern comprising peaks at the following diffraction angles (2θ (degrees)) 4.5±0.3, and 9.0±0.3. In some embodiments, Form 1 exhibits an X-ray power diffraction pattern comprising peaks at the following diffraction angles (2θ (degrees)) 4.5±0.3, 9.0±0.3, and 18.1±0.3.

In some embodiments, provided herein is an oral dosage form comprising (a) an effective amount of crystalline Form 1 of a compound of Formula II, wherein Form 1 exhibits an X-ray power diffraction pattern comprising a characteristic XRPD peak at the following diffraction angle (2θ (degrees))=9.0±0.5; and (b) at least one pharmaceutically acceptable carrier. In some embodiments, Form 1 exhibits an X-ray power diffraction pattern comprising peaks at the following diffraction angles (2θ (degrees)) 4.5±0.5, and 9.0±0.5. In some embodiments, Form 1 exhibits an X-ray power diffraction pattern comprising peaks at the following diffraction angles (2θ (degrees)) 4.5±0.5, 9.0±0.5, and 18.1±0.5.

In some embodiments, the oral dosage form is a solid oral dosage form contained within a capsule.

In some embodiments, the oral dosage form comprises about 0.8 mg (based on free form; 0.864 mg based on Form 1) of the solid form of a compound of Formula II. In some embodiments, the oral dosage form comprises about 0.8% w/w (based on free form; 0.864% w/w based on Form 1) of the solid form of a compound of Formula II.

In some embodiments, the pharmaceutically acceptable carrier is a filler. In some embodiments, the filler is mannitol. In some embodiments, the mannitol is a mixture of fine mannitol and granular mannitol.

In some embodiments, the filler (e.g., mannitol) is present in the oral dosage form in an amount of about 90% w/w to about 99% w/w. In some embodiments, the filler (e.g., mannitol) is present in the oral dosage form in an amount of about 95% w/w to about 99% w/w. In some embodiments, the filler (e.g., mannitol) is present in the oral dosage form in an amount of about 97% w/w to about 99% w/w. In some embodiments, the filler (e.g., mannitol) is present in the oral dosage form in an amount of about 97% w/w to about 98% w/w. In some embodiments, the filler (e.g., mannitol) is present in the oral dosage form in an amount of about % w/w. In some embodiments, the filler (e.g., mannitol) is present in the oral dosage form in an amount of about 95% w/w. In some embodiments, the filler (e.g., mannitol) is present in the oral dosage form in an amount of about 97% w/w.

In some embodiments, the oral dosage form further comprises a lubricant. In some embodiments, the lubricant is magnesium stearate.

In some embodiments, the lubricant (e.g., magnesium stearate) is present in the oral dosage form in an amount of about 0.05% w/w to about 3% w/w. In some embodiments, the lubricant (e.g., magnesium stearate) is present in the oral dosage form in an amount of about w/w to about 3% w/w. In some embodiments, the lubricant (e.g., magnesium stearate) is present in the oral dosage form in an amount of about 0.5% w/w to about 3% w/w. In some embodiments, the lubricant (e.g., magnesium stearate) is present in the oral dosage form in an amount of about 1% w/w to about 3% w/w. In some embodiments, the lubricant (e.g., magnesium stearate) is present in the oral dosage form in an amount of about 1% w/w to about 2% w/w. In some embodiments, the lubricant (e.g., magnesium stearate) is present in the oral dosage form in an amount of about 0.05% w/w to about 2% w/w. In some embodiments, the lubricant (e.g., magnesium stearate) is present in the oral dosage form in an amount of about w/w to about 2% w/w. In some embodiments, the lubricant (e.g., magnesium stearate) is present in the oral dosage form in an amount of about 0.5% w/w to about 2% w/w. In some embodiments, the lubricant (e.g., magnesium stearate) is present in the oral dosage form in an amount of about 0.1% w/w to about 3% w/w. In some embodiments, the lubricant (e.g., magnesium stearate) is present in the oral dosage form in an amount of about 0.5% w/w. In some embodiments, the lubricant (e.g., magnesium stearate) is present in the oral dosage form in an amount of about 1% w/w. In some embodiments, the lubricant (e.g., magnesium stearate) is present in the oral dosage form in an amount of about 1.5% w/w. In some embodiments, the lubricant (e.g., magnesium stearate) is present in the oral dosage form in an amount of about 2% w/w. In some embodiments, the lubricant (e.g., magnesium stearate) is present in the oral dosage form in an amount of about 2.5% w/w. In some embodiments, the lubricant (e.g., magnesium stearate) is present in the oral dosage form in an amount of about 3% w/w.

In some embodiments, provided herein is an oral dosage form comprising: (a) about 0.8% w/w (based on free form) of Form 1 of a compound of Formula II, wherein Form 1 exhibits an X-ray power diffraction pattern comprising a characteristic XRPD peak at the following diffraction angles (2θ (degrees))=9.0±0.2; and (b) a pharmaceutically acceptable filler in an amount of about 95% w/w to about 98% w/w; and (c) a pharmaceutically acceptable lubricant in an amount of about 1% to about 2%.

In some embodiments, provided herein is an oral dosage form comprising: (a) about 0.8% w/w (based on free form) of Form 1 of a compound of Formula II, wherein Form 1 exhibits an X-ray power diffraction pattern comprising peaks at the following diffraction angles (2θ (degrees))=4.5±0.2 and 9.0±0.2; and (b) a pharmaceutically acceptable filler in an amount of about 95% w/w to about 98% w/w; and (c) a pharmaceutically acceptable lubricant in an amount of about 1% to about 2%.

In some embodiments, provided herein is an oral dosage form comprising: (a) about 0.8% w/w (based on free form) of Form 1 of a compound of Formula II, wherein Form 1 exhibits an X-ray power diffraction pattern comprising peaks at the following diffraction angles (2θ (degrees))=4.5±0.2, 9.0±0.2, and 18.1±0.2; and (b) a pharmaceutically acceptable filler in an amount of about 95% w/w to about 98% w/w; and (c) a pharmaceutically acceptable lubricant in an amount of about 1% to about 2%.

In some embodiments, provided herein is an oral dosage form comprising: (a) about 0.8% w/w (based on free form) of Form 1 of a compound of Formula II, wherein Form 1 exhibits an X-ray power diffraction pattern comprising a characteristic XRPD peak at the following diffraction angles (2θ (degrees))=9.0±0.3; and (b) a pharmaceutically acceptable filler in an amount of about 95% w/w to about 98% w/w; and (c) a pharmaceutically acceptable lubricant in an amount of about 1% to about 2%.

In some embodiments, provided herein is an oral dosage form comprising: (a) about 0.8% w/w (based on free form) of Form 1 of a compound of Formula II, wherein Form 1 exhibits an X-ray power diffraction pattern comprising peaks at the following diffraction angles (2θ (degrees))=4.5±0.3 and 9.0±0.3; and (b) a pharmaceutically acceptable filler in an amount of about 95% w/w to about 98% w/w; and (c) a pharmaceutically acceptable lubricant in an amount of about 1% to about 2%.

In some embodiments, provided herein is an oral dosage form comprising: (a) about 0.8% w/w (based on free form) of Form 1 of a compound of Formula II, wherein Form 1 exhibits an X-ray power diffraction pattern comprising peaks at the following diffraction angles (2θ (degrees))=4.5±0.3, 9.0±0.3, and 18.1±0.3; and (b) a pharmaceutically acceptable filler in an amount of about 95% w/w to about 98% w/w; and (c) a pharmaceutically acceptable lubricant in an amount of about 1% to about 2%.

In some embodiments, provided herein is an oral dosage form comprising: (a) about 0.8% w/w (based on free form) of Form 1 of a compound of Formula II, wherein Form 1 exhibits an X-ray power diffraction pattern comprising a characteristic XRPD peak at the following diffraction angles (2θ (degrees))=9.0±0.5; and (b) a pharmaceutically acceptable filler in an amount of about 95% w/w to about 98% w/w; and (c) a pharmaceutically acceptable lubricant in an amount of about 1% to about 2%.

In some embodiments, provided herein is an oral dosage form comprising: (a) about 0.8% w/w (based on free form) of Form 1 of a compound of Formula II, wherein Form 1 exhibits an X-ray power diffraction pattern comprising peaks at the following diffraction angles (2θ (degrees))=4.5±0.5 and 9.0±0.5; and (b) a pharmaceutically acceptable filler in an amount of about 95% w/w to about 98% w/w; and (c) a pharmaceutically acceptable lubricant in an amount of about 1% to about 2%.

In some embodiments, provided herein is an oral dosage form comprising: (a) about 0.8% w/w (based on free form) of Form 1 of a compound of Formula II, wherein Form 1 exhibits an X-ray power diffraction pattern comprising peaks at the following diffraction angles (2θ (degrees))=4.5±0.5, 9.0±0.5, and 18.1±0.5; and (b) a pharmaceutically acceptable filler in an amount of about 95% w/w to about 98% w/w; and (c) a pharmaceutically acceptable lubricant in an amount of about 1% to about 2%.

In an aspect, provided herein is a method of manufacturing the oral dosage form comprising: (a) about 0.8% w/w (based on free form) of Form 1 of a compound of Formula II, wherein Form 1 exhibits an X-ray power diffraction pattern comprising a characteristic XRPD peak at the following diffraction angle (2θ (degrees))=9.0±0.2; and (b) pharmaceutically acceptable filler in an amount of about 95% w/w to about 98% w/w; and (c) a pharmaceutically acceptable lubricant in an amount of about 1% to about 2%, the method comprising:
(i) sieving a first portion of the filler via a screen and blending the sieved first portion of the filler;
(ii) sieving Form 1 of a compound of Formula II via a screen and blending the sieved Form 1 with the sieved and blended first portion of the filler of step (i) to form a pre-blend 1;
(iii) sieving a second portion of the filler via a screen and blending the sieved second portion of the filler;
(iv) contacting the pre-blend 1 with the sieved and blended second portion of the filler of step (iii) and blending to form a pre-blend 2;
(v) sieving a third portion of the filler via a screen and blending the sieved third portion of the filler;
(vi) contacting the pre-blend 2 with the sieved and blended third portion of the filler of step (v) and blending to form a blend;
(vii) sieving the lubricant via a screen and blending with the blend of step (vi) to form a final blend; and
(viii) encapsulating the final blend in a capsule shell, thereby forming the oral dosage form.

In some embodiments, Form 1 exhibits an X-ray power diffraction pattern comprising peaks at the following diffraction angles (2θ (degrees))=4.5±0.2, and 9.0±0.2. In some embodiments, Form 1 exhibits an X-ray power diffraction pattern comprising peaks at the following diffraction angles (2θ (degrees)) 4.5±0.2, 9.0±0.2, and 18.1±0.2.

In an aspect, provided herein is a method of manufacturing the oral dosage form comprising: (a) about 0.8% w/w (based on free form) of Form 1 of a compound of Formula II, wherein Form 1 exhibits an X-ray power diffraction pattern comprising a characteristic XRPD peak at the following diffraction angle (2θ (degrees))=9.0±0.3; and (b) pharmaceutically acceptable filler in an amount of about 95% w/w to about 98% w/w; and (c) a pharmaceutically acceptable lubricant in an amount of about 1% to about 2%, the method comprising:
(i) sieving a first portion of the filler via a screen and blending the sieved first portion of the filler;
(ii) sieving Form 1 of a compound of Formula II via a screen and blending the sieved Form 1 with the sieved and blended first portion of the filler of step (i) to form a pre-blend 1;
(iii) sieving a second portion of the filler via a screen and blending the sieved second portion of the filler;
(iv) contacting the pre-blend 1 with the sieved and blended second portion of the filler of step (iii) and blending to form a pre-blend 2;

(v) sieving a third portion of the filler via a screen and blending the sieved third portion of the filler;
(vi) contacting the pre-blend 2 with the sieved and blended third portion of the filler of step (v) and blending to form a blend;
(vii) sieving the lubricant via a screen and blending with the blend of step (vi) to form a final blend; and
(viii) encapsulating the final blend in a capsule shell, thereby forming the oral dosage form.

In some embodiments, Form 1 exhibits an X-ray power diffraction pattern comprising peaks at the following diffraction angles (2θ (degrees))=4.5±0.3, and 9.0±0.3. In some embodiments, Form 1 exhibits an X-ray power diffraction pattern comprising peaks at the following diffraction angles (2θ (degrees)) 4.5±0.3, 9.0±0.3, and 18.1±0.3.

In an aspect, provided herein is a method of manufacturing the oral dosage form comprising: (a) about 0.8% w/w (based on free form) of Form 1 of a compound of Formula II, wherein Form 1 exhibits an X-ray power diffraction pattern comprising a characteristic XRPD peak at the following diffraction angle (2θ (degrees))=9.0±0.5; and (b) pharmaceutically acceptable filler in an amount of about 95% w/w to about 98% w/w; and (c) a pharmaceutically acceptable lubricant in an amount of about 1% to about 2%, the method comprising:
(i) sieving a first portion of the filler via a screen and blending the sieved first portion of the filler;
(ii) sieving Form 1 of a compound of Formula II via a screen and blending the sieved Form 1 with the sieved and blended first portion of the filler of step (i) to form a pre-blend 1;
(iii) sieving a second portion of the filler via a screen and blending the sieved second portion of the filler;
(iv) contacting the pre-blend 1 with the sieved and blended second portion of the filler of step (iii) and blending to form a pre-blend 2;
(v) sieving a third portion of the filler via a screen and blending the sieved third portion of the filler;
(vi) contacting the pre-blend 2 with the sieved and blended third portion of the filler of step (v) and blending to form a blend;
(vii) sieving the lubricant via a screen and blending with the blend of step (vi) to form a final blend; and
(viii) encapsulating the final blend in a capsule shell, thereby forming the oral dosage form.

In some embodiments, Form 1 exhibits an X-ray power diffraction pattern comprising peaks at the following diffraction angles (2θ (degrees))=4.5±0.5, and 9.0±0.5. In some embodiments, Form 1 exhibits an X-ray power diffraction pattern comprising peaks at the following diffraction angles (2θ (degrees)) 4.5±0.5, 9.0±0.5, and 18.1±0.5.

In some embodiments, the blending is performed using a high shear dry blending.

In some embodiments, the first portion of the filler is fine mannitol powder.

In some embodiments, the second portion of the filler is granular mannitol.

In some embodiments, the second portion of the filler is granular mannitol.

In some embodiments, the lubricant is magnesium stearate.

In some embodiments, the capsule shell is a hypromellose capsule shell.

Methods of Treatment

Methods described herein contemplate treating an abnormal cell growth (e.g., cancer) in a subject in need thereof by administering to the subject an effective amount of a solid form of a compound of Formula II or a pharmaceutical composition described herein.

Abnormal Cell Growth

Abnormal cell growth, as used herein and unless otherwise indicated, refers to cell growth that is independent of normal regulatory mechanisms (e.g., loss of contact inhibition). This includes the abnormal growth of: (1) tumor cells (tumors) that proliferate, for example, by expressing a mutated tyrosine kinase or overexpression of a receptor tyrosine kinase; (2) benign and malignant cells of other proliferative diseases, for example, in which aberrant tyrosine kinase activation occurs; (3) any tumors that proliferate, for example, by receptor tyrosine kinases; (4) any tumors mat proliferate, for example, by aberrant serine/threonine kinase activation; and (5) benign and malignant cells of other proliferative diseases, for example, in which aberrant serine/threonine kinase activation occurs. Abnormal cell growth can refer to cell growth in epithelial (e.g., carcinomas, adenocarcinomas): mesenchymal (e.g., sarcomas (e.g. leiomyosarcoma. Ewing's sarcoma)); hematopoetic (e.g., lymphomas, leukemias, myelodysplasias (e.g., pre-malignant)); or other (e.g., melanoma, mesothelioma, and other tumors of unknown origin) cell.

Neoplastic Disorders

Abnormal cell growth can refer to a neoplastic disorder. A "neoplastic disorder" is a disease or disorder characterized by cells that have the capacity for autonomous growth or replication, e.g., an abnormal state or condition characterized by proliferative cell growth. An abnormal mass of tissue as a result of abnormal cell growth or division, or a "neoplasm," can be benign, pre-malignant (carcinoma in situ) or malignant (cancer).

Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Treatment with a solid form of a compound of Formula II disclosed herein may be in an amount effective to ameliorate at least one symptom of the neoplastic disorder, e.g., reduced cell proliferation, reduced tumor mass, etc.

Cancers

The inventive methods of the present invention may be useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer (e.g. Hepatocellular carcinoma), non-small cell carcinoma of the lung, pancreatic (e.g., metastatic pancreatic ductal adenocarcinoma) and cancer of the small intestine.

The cancer can include mesothelioma; neurofibromatosis, e.g., neurofibromatosis type 2, neurofibromatosis type 1; renal cancer; lung cancer, e.g., non-small cell lung cancer, e.g., metastatic NSCLC; lung adenocarcinoma, e.g., NSCLC adenocarcinoma; liver cancer; thyroid cancer; ovarian cancer, e.g., low grade serous ovarian cancer; breast cancer; pancreatic cancer, e.g., pancreatic adenocarcinoma; colorectal cancer, e.g., colorectal adenocarcinoma; uterine endometrioid carcinoma; a gynecologic cancer, e.g., cervical cancer, ovarian cancer, uterine cancer, vaginal cancer, endometrial cancer, or vulvar cancer; liver cancer; prostate cancer; mesothelioma; bladder cancer; melanoma, e.g., unresectable melanoma, metastatic melanoma; thyroid cancer, e.g., papillary thyroid cancer, follicular thyroid cancer, anaplastic thyroid cancer; glioblastoma; renal cancer; a nervous system tumor; schwannoma; meningioma; schwannomatosis; neuroma acoustic; adenoid cystic carcinoma; ependymoma; and ependymal tumors.

In some embodiments, the cancer is lung cancer, e.g., non-small cell lung cancer. In some embodiments, the cancer is ovarian cancer, e.g., low grade serous ovarian cancer.

The cancer can include cancers characterized as comprising cancer stem cells, cancer associated mesenchymal cells, or tumor initiating cancer cells. The cancer can include cancers that have been characterized as being enriched with cancer stem cells, cancer associated mesenchymal cells, or tumor initiating cancer cells (e.g., a tumor enriched with cells that have undergone an epithelial-to-mesenchymal transition or a metastatic tumor).

The cancer can be a primary tumor, i.e., located at the anatomical site of tumor growth initiation. The cancer can also be metastatic, i.e., appearing at least a second anatomical site other than the anatomical site of tumor growth initiation. The cancer can be a recurrent cancer, i.e., cancer that returns following treatment, and after a period of time in which the cancer was undetectable. The recurrent cancer can be anatomically located locally to the original tumor, e.g., anatomically near the original tumor; regionally to the original tumor, e.g., in a lymph node located near the original tumor; or distantly to the original tumor, e.g., anatomically in a region remote from the original tumor.

The cancer can also include for example, but is not limited to, epithelial cancers, breast, lung, pancreatic, colorectal, prostate, head and neck, melanoma, acute myelogenous leukemia, and glioblastoma. Exemplary breast cancers include triple negative breast cancer, basal-like breast cancer, claudin-low breast cancer, invasive, inflammatory, metaplastic, and advanced HER-2 positive or ER-positive cancers resistant to therapy.

The cancer can also include lung adenocarcinoma, colorectal cancer (CRC), uveal melanoma, ovarian cancer, uterine endometrioid carcinoma, bladder urothelial carcinoma, breast invasive lobular carcinoma, cervical squamous cell carcinoma, cutaneous melanoma, endocervical adenocarcinoma, hepatocellular carcinoma, pancreatic adenocarcinoma, biphasic type pleural mesothelioma, renal clear cell carcinoma, renal clear cell carcinoma, stomach adenocarcinoma, tubular stomach adenocarcinoma, uterine carcinosarcoma, or uterine malignant mixed Mullerian tumor.

In some embodiments, the cancer is unresectable or metastatic melanoma, melanoma with lymph node involvement or metastatic disease who have undergone complete resection, metastatic non-small cell lung cancer and progression on or after platinum-based chemotherapy, metastatic small cell lung cancer with progression after platinum-based chemotherapy and at least one other line of therapy, advanced renal cell carcinoma who have received prior antiangiogenic therapy, advanced renal cell carcinoma, classical Hodgkin lymphoma, recurrent or metastatic squamous cell carcinoma of the head and neck with disease progression on or after a platinum-based therapy, locally advanced or metastatic urothelial carcinoma, microsatellite instability-high (MSI-H) or mismatch repair deficient (dMMR) metastatic colorectal cancer, or hepatocellular carcinoma.

In some embodiments, the cancer is melanoma, non-small cell lung cancer, small cell lung cancer, head and neck squamous cell cancer, classical Hodgkin lymphoma, primary mediastinal large B-cell lymphoma, urothelial carcinoma, microsatellite instability-high cancer, gastric cancer, esophageal cancer, cervical cancer, hepatocellular carcinoma, merkel cell carcinoma, renal cell carcinoma, or endometrial carcinoma.

Other cancers include but are not limited to, uveal melanoma, brain, abdominal, esophagus, gastrointestinal, glioma, liver, tongue, neuroblastoma, osteosarcoma, ovarian, retinoblastoma, Wilm's tumor, multiple myeloma, skin, lymphoma, blood and bone marrow cancers (e.g., advanced hematological malignancies, leukemia, e.g., acute myeloid leukemia (e.g., primary or secondary), acute lymphoblastic leukemia, acute lymphocytic leukemia, T cell leukemia, hematological malignancies, advanced myeloproliferative disorders, myelodysplastic syndrome, relapsed or refractory multiple myeloma, advanced myeloproliferative disorders), retinal, bladder, cervical, kidney, endometrial, meningioma, lymphoma, skin, uterine, lung, non small cell lung, nasopharyngeal carcinoma, neuroblastoma, solid tumor, hematologic malignancy, squamous cell carcinoma, testicular, thyroid, mesothelioma, brain vulval, sarcoma, intestine, oral, endocrine, salivary, spermatocyte seminoma, sporadic medulalry thyroid carcinoma, non-proliferating testes cells, cancers related to malignant mast cells, non-Hodgkin's lymphoma, and diffuse large B cell lymphoma.

In some embodiments, the tumor is a solid tumor. In some embodiments, the solid tumor is locally advanced or metastatic, hi some embodiments, the solid tumor is refractory (e.g., resistant) after standard therapy.

Methods described herein can reduce, ameliorate or altogether eliminate the disorder or its associated symptoms, or a combination thereof, to keep it from becoming worse, to slow the rate of progression, or to minimize the rate of recurrence of the disorder once it has been initially eliminated (i.e., to avoid a relapse). A suitable dose and therapeutic regimen may vary depending upon the specific compounds, combinations, or pharmaceutical compositions used and the mode of delivery of the compounds, combinations, or pharmaceutical compositions. In some embodiments, the method increases the average length of survival, increases the average length of progression-free survival, or reduces the rate of recurrence, or a combination thereof, of subjects treated with a solid form of a compound of Formula II described herein in a statistically significant manner.

In some embodiments, the cancer is lung cancer, bone cancer, pancreatic cancer, skin cancer, cancer of the head or neck, cutaneous or intraocular melanoma, uterine cancer, ovarian cancer (e.g., unresectable low-grade ovarian, advanced or metastatic ovarian cancer), rectal cancer, cancer of the anal region, stomach cancer, colon cancer, breast cancer (e.g., triple-negative breast cancer (e.g., breast cancer which does not express the genes for the estrogen receptor, progesterone receptor, and Her2/neu)), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, mesothelioma (e.g., malignant pleural mesothelioma, e.g., surgical resectable malignant pleural mesothelioma) or a combination of one or more of the foregoing cancers. In some embodiments, the cancer is metastatic. In some embodiments, the abnormal cell growth is locally recurring (e.g. the subject has a locally recurrent disease, e.g., cancer).

Additional Therapies

In some embodiments, the methods and compositions described herein is administered together with an additional therapy or additional agent. In one embodiment, a mixture of one or more compounds or pharmaceutical compositions may be administered with an additional therapy or additional agent to a subject in need thereof. In yet another embodiment, one or more compounds or pharmaceutical compositions may be administered with an additional therapy or additional agent for the treatment or avoidance of various diseases, including, for example, cancer, diabetes, neurodegenerative diseases, cardiovascular disease, blood clotting, inflammation, flushing, obesity, aging, stress, etc. In various embodiments, combination therapies comprising a compound or pharmaceutical composition described herein may refer to (1) pharmaceutical compositions that comprise one or more compounds in combination with an additional therapy or additional agent; and (2) co-administration of one or more compounds or pharmaceutical compositions described herein with an additional therapy or additional agent, wherein the compound or pharmaceutical composition described herein have not been formulated in the same compositions. In some embodiments, a solid form of a compound of Formula II described herein is administered with an additional treatment (e.g., an additional cancer treatment). In some embodiments, the additional treatment (e.g., an additional cancer treatment) can be administered simultaneously (e.g., at the same time), in the same or in separate compositions, or sequentially. Sequential administration refers to administration of one treatment before (e.g., immediately before, less than 5, 10, 15, 30, 45, 60 minutes; 1, 2, 3, 4, 6, 8, 10, 12, 16, 20, 24, 48, 72, 96 or more hours; 4, 5, 6, 7, 8, 9 or more days; 1, 2, 3, 4, 5, 6, 7, 8 or more weeks before) administration of an additional, e.g., secondary, treatment (e.g., a compound or therapy). The order of administration of the first and secondary compound or therapy can also be reversed.

Exemplary cancer treatments include, for example: chemotherapy, targeted therapies such as antibody therapies, immunotherapy, and hormonal therapy. Examples of each of these treatments are provided below.

Chemotherapy

In some embodiments, a solid form of a compound of Formula II described herein is administered with chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

In some embodiments, a solid form of a compound of Formula II described herein is administered with one or more chemotherapeutic agent. Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptotnecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Folfirinox, Fotemustine, Gemcitabine, Gliadel implants, Hydroxycarbamide, Hydroxyurea, idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixanlrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time or sequentially. Often, two or more chemotherapy agents are used as combination chemotherapy. In some embodiments, the chemotherapy agents (including combination chemotherapy) can be used in combination with a solid form of a compound of Formula II described herein.

Targeted Therapy

In some embodiments, a solid form of a compound of Formula II described herein is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a solid form of a compound of Formula II described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decay s in the vicinity of the cell. An example of such therapy includes BEXXAR®.

Immunotherapy

In some embodiments, a solid form of a compound of Formula II described herein is administered with an immunotherapy. Cancer immunotherapy refers to a diverse set of therapeutic strategies designed to induce the subject's own immune system to fight the tumor.

Contemporary methods for generating an immune response against tumors include intravesicular BCG immunotherapy for superficial bladder cancer, and use of interferons and other cytokines to induce an immune response in subjects with renal cell carcinoma and melanoma. Allogeneic hematopoietic stem cell transplantation can be considered a form of immunotherapy, since the donor's immune cells will often attack the tumor in a graft-versus-tumor effect. In some embodiments, the immunotherapy agents can be used in combination with a solid form of a compound of Formula II as described herein.

Hormonal Therapy

In some embodiments, a solid form of a compound of Formula II described is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a solid form of a compound of Formula II described herein.

In some embodiments, the additional agent is an agent that modifies ER, PR, or AR, or a combination thereof. For example, the additional agent is an AR antagonist, which includes, but is not limited to, flutamide, bicalutamide and nilutamide. In some embodiments, the additional agent is an agent that blocks estrogen or progesterone, which includes, aromatase inhibitors including but is not limited to, anastrozole, letrozole, and exemestane. In some embodiments, the additional agent is an estrogen receptor modulator including, but not limited to, fulvetrant, tamoxifen and raloxifene.

Radiation Therapy

A solid form of a compound of Formula II described herein can be used in combination with directed energy or particle, or radioisotope treatments, e.g., radiation therapies, e.g., radiation oncology, for the treatment of proliferative disease, e.g., cancer, e.g., cancer associated with cancer stem cells. A solid form of a compound of Formula II described herein may be administered to a subject simultaneously or sequentially along with the directed energy or particle, or radioisotope treatments. For example, the solid form of a compound of Formula II described herein may be administered before, during, or after the directed energy or particle, or radioisotope treatment, or a combination thereof. The directed energy or particle therapy may comprise total body irradiation, local body irradiation, or point irradiation. The directed energy or particle may originate from an accelerator, synchrotron, nuclear reaction, vacuum tube, laser, or from a radioisotope. The therapy may comprise external beam radiation therapy, teletherapy, brachy therapy, sealed source radiation therapy, systemic radioisotope therapy, or unsealed source radiotherapy. The therapy may comprise ingestion of, or placement in proximity to, a radioisotope, e.g., radioactive iodine, cobalt, cesium, potassium, bromine, fluorine, carbon. External beam radiation may comprise exposure to directed alpha particles, electrons (e.g., beta particles), protons, neutrons, positrons, or photons (e.g., radiowave, millimeter wave, microwave, infrared, visible, ultraviolet, X-ray, or gamma-ray photons). The radiation may be directed at any portion of the subject in need of treatment.

Surgery

A solid form of a compound of Formula II described herein can be used in combination with surgery, e.g., surgical exploration, intervention, biopsy, for the treatment of proliferative disease, e.g., cancer, e.g., cancer associated with cancer stem cells. A solid form of a compound of Formula II described herein may be administered to a subject simultaneously or sequentially along with the surgery. For example, a solid form of a compound of Formula II described herein may be administered before (preoperative), during, or after (post-operative) the surgery, or a combination thereof. The surgery may be a biopsy during which one or more cells are collected for further analysis. The biopsy may be accomplished, for example, with a scalpel, a needle, a catheter, an endoscope, a spatula, or scissors. The biopsy may be an excisional biopsy, an incisional biopsy, a core biopsy, or a needle biopsy, e.g., a needle aspiration biopsy. The surgery may involve the removal of localized tissues suspected to be or identified as being cancerous. For example, the procedure may involve the removal of a cancerous lesion, lump, polyp, or mole. The procedure may involve the removal of larger amounts of tissue, such as breast, bone, skin, fat, or muscle. The procedure may involve removal of part of, or the entirety of, an organ or node, for example, lung, throat, tongue, bladder, cervix, ovary, testicle, lymph node, liver, pancreas, brain, eye, kidney, gallbladder, stomach, colon, rectum, or intestine. In one embodiment, the cancer is breast cancer, e.g., triple negative breast cancer, and the surgery is a mastectomy or lumpectomy.

Anti-Inflammatory Agents

A solid form of a compound of Formula II described herein can be administered with an anti-inflammatory agent. Anti-inflammatory agents can include, but are not limited to, non-steroidal anti-inflammatory agents (e.g., Salicylates (Aspirin (acetylsalicylic acid), Diflunisal, Salsalate), Propionic acid derivatives (Ibuprofen, Naproxen, Fenoprofen, Ketoprofen, Flurbiprofen, Oxaprozin, Loxoprofen), Acetic acid derivatives (Indomethacin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives (Fenamates)(Mefenamic acid, Meclofenamic acid, Flufenamic acid. Tolfenamic acid). Selective COX-2 inhibitors (Coxibs) (Ceiecoxib), Sulphonanilides (Nimesulide). Steriods (e.g. Hydrocortisone (Cortisol), Cortisone acetate, Prednisone, Prednisolone, Methylprednisolone, Dexamethasone, Betamethasone, Triamcinolone, Beclometasone, Fludrocortisone acetate, Deoxycorticosterone acetate, Aldosterone).

Analgesic Agents

Analgesics can include but are not limited to, opiates (e.g. morphine, codeine, oxycodone, hydrocodone, dihydromorphine, pethidine, buprenorphine, tramadol, venlafaxine), paracetomal and Nonsteroidal anti-inflammatory agents (e.g., Salicylates (Aspirin (acetylsalicylic acid), Diflunisal, Salsalate), Propionic acid derivatives (Ibuprofen, Naproxen, Fenoprofen, Ketoprofen, Flurbiprofen, Oxaprozin, Loxoprofen), Acetic acid derivatives (Indomethacin, Sulindac, Etodolac, Ketorolac, Diclofenac, Nabumetone), Enolic acid (Oxicam) derivatives (Piroxicam, Meloxicam, Tenoxicam, Droxicam, Lomoxicam, Isoxicam), Fenamic acid derivatives (Fenamates)(Mefenamic acid, Meclofenamic acid, Flufenamic acid. Tolfenamic acid). Selective COX-2 inhibitors (Coxibs) (Ceiecoxib), Sulphonanilides (Nimesulide).

Antiemetic Agents

A solid form of a compound of Formula II described herein can be administered with an antiemetic agent. Antiemetic agents can include, but are not limited to, 5-HT3 receptor antagonists (Dolasetron (Anzemet), Granisetron (Kytril, Sancuso), Ondansetron (Zofran), Tropisetron (Navoban), Palonosetron (Aloxi), Mirtazapine (Remeron)), Dopamine antagonists (Domperidone, Olanzapine, Droperidol, Haloperidol, Chlorpromazine, Promethazine, Prochlorperazine, Metoclopramide (Reglan), Alizapride, Prochlorperazine (Compazine, Stemzine, Buccastem, Stemetil, Phenotil), NK1 receptor antagonist (Aprepitant (Emend), Antihistamines (Cyclizine, Diphenhydramine (Benadryl), Dimenhydrinate (Gravol, Dramamine), Meclozine (Bonine, Antivert), Promethazine (Pentazine, Phenergan, Promacot), Hydroxyzine), benzodiazepines (Lorazepam, Midazolam), Anticholinergics (hyoscine), steroids (Dexamethasone).

Combinations

The phrase, "in combination with," and the terms "co-administration," "co-administering," or "co-providing", as used herein in the context of the administration of a compound described herein or a therapy described herein, means that two (or more) different compounds or therapies are delivered to the subject during the course of the subject's affliction with the disease or disorder (e.g., a disease or disorder as described herein, e.g., cancer), e.g., two (or more) different compounds or therapies are delivered to the subject after the subject has been diagnosed with the disease or disorder (e.g., a disease or disorder as described herein, e.g., cancer) and before the disease or disorder has been cured or eliminated or treatment has ceased for other reasons.

In some embodiments, the delivery of one compound or therapy is still occurring when the delivery of the second begins, so that there is overlap in terms of administration. This is sometimes referred to herein as "simultaneous" or "concurrent delivery." In other embodiments, the delivery of one compound or therapy ends before the delivery of the other compound or therapy begins. In some embodiments of either case, the treatment (e.g., administration of compound, composition, or therapy) is more effective because of combined administration. For example, the second compound or therapy is more effective, e.g., an equivalent effect is seen with less of the second compound or therapy, or the second compound or therapy reduces symptoms to a greater extent, than would be seen if the second compound or therapy were administered in the absence of the first compound or therapy, or the analogous situation is seen with the first compound or therapy. In some embodiments, delivery is such that the reduction in a symptom, or other parameter related to the disorder is greater than what would be observed with one compound or therapy delivered in the absence of the other. The effect of the two compounds or therapies can be partially additive, wholly additive, or great than additive (e.g., synergistic). The delivery can be such that the first compound or therapy delivered is still detectable when the second is delivered.

In some embodiments, the first compound or therapy and second compound or therapy can be administered simultaneously (e.g., at the same time), in the same or in separate compositions, or sequentially. Sequential administration refers to administration of one compound or therapy before (e.g., immediately before, less than 5, 10, 15, 30, 45, 60 minutes; 1, 2, 3, 4, 6, 8, 10, 12, 16, 20, 24, 48, 72, 96 or more hours; 4, 5, 6, 7, 8, 9 or more days; 1, 2, 3, 4, 5, 6, 7, 8 or more weeks before) administration of an additional, e.g., secondary, compound or therapy. The order of administration of the first and secondary compound or therapy can also be reversed.

The combinations described herein can be a first line treatment for abnormal cell growth, e.g., cancer, i.e., it is used in a subject who has not been previously administered another drug intended to treat the cancer; a second line treatment for the cancer, i.e., it is used in a subject in need thereof who has been previously administered another drug intended to treat the cancer; a third or fourth treatment for the cancer, i.e., it is used in a subject who has been previously administered two or three other drugs intended to treat the cancer.

EXAMPLES

The representative examples that follow are intended to help illustrate the invention, and are not intended to, nor should they be construed to, limit the scope of the invention.

List of Abbreviations

1H NMR Proton Nuclear Magnetic Resonance
API Active Pharmaceutical Ingredient
DSC Differential Scanning calorimetry
DVS Dynamic Vapor Sorption
KF Karl Fischer
TGA Thermogravimetric Analysis
XRPD X-Ray Powder Diffraction
RT Room temperature
PLM Polarized Light Microscopy
RH Relative Humidity
SFS Solid Form Screening
NMP N-methyl-2-pyrrolidone
THF Tetrahydrofuran
EtOAc Ethyl acetate
IPAc Isopropyl acetate
MIBK Methyl isobutyl ketone
MEK Methyl ethyl ketone
IPA Isopropyl alcohol
DMSO Dimethyl sulfoxide
DMF Dimethylformamide
MeCN Acetonitrile
MeOH Methanol
TBME Tert-Butyl methyl ether
DCM Dichloromethane Analytical Techniques Differential Scanning Calorimetry (DSC)

Samples were analyzed using a TA Instruments Q2000. Samples of 2-8 mg were hermetically sealed in a Tzero aluminum sample pan with matching lid. The sample was scanned from 25° C. to 300° C. at a rate of 10° C./min under a nitrogen purge of 50 mL/min.

Thermogravimetric Analysis (TGA)

Thermal analysis of the sample was performed using a TA Instruments Q500 TGA equipped with a single position sampler. Samples of 2-10 mg were loaded into a sealed, pre-tared, aluminum DSC pan with a pin hole in the lid to allow gases to escape. The sample was scanned from 25° C. to 350° C. at the rate of 10° C./min coupled with a 60 mL/min nitrogen purge.

Dynamic Vapor Sorption (DVS)

Samples were analyzed using a TA Instruments Q5000SA gravimetric water sorption analyzer. The weight of the sample was continuously monitored and recorded with respect to the relative humidity (RH) and time. Samples of 5-10 mg were placed in a tared, hermetically sealed aluminum DVS pan under ambient conditions. The sample pan was punctured prior to being loaded into the humidity chamber. A moisture sorption isotherm was performed at 25° C. at 10% RH intervals over a 0-90% RH range. Three cycles were carried out. If the mass gain or loss on a sorption step was less than 0.1% over 15 minutes, the next humidity interval would begin. If weight continued to change after 120 minutes at a given step, the step would time out and proceed to the next humidity interval.

X-Ray Powder Diffraction (XRPD)

X-ray powder diffraction patterns were obtained using a Bruker D8 equipped with a Cu Kα radiation (40 kV, 40 mA) source ($\lambda$=1.54° Å), a 9-position sample holder, and a θ-2θ goniometer fitted with a Ge monochromator. The incident beam passes through a 2.0 mm divergence slit followed by a 0.2 mm antiscatter slit. The diffracted beam passes through an 8.0 mm receiving slit with 2.5° Soller slits followed by a LYNXEYE super speed detector. Samples were prepared on polished, zero-background silicon plates and run using a low background, airtight specimen dome.

For initial pattern screening, the Bruker D8 followed a four-minute method and the angular range was 3 to 40° with a step size of 0.014° 2θ at 0.1 seconds per step. For final form collection, the Bruker D8 followed a 30-minute method and angular range was 3 to 40° with a step size of 0.018° 2θ at 0.85 seconds per step. The software used for data collection and analysis was Diffrac Plus XRD Commander and Diffrac Plus EVA, respectively.

Proton Nuclear Magnetic Resonance (1H NMR)

1H NMR data were collected using a Bruker Ascend 600 MHz NMR equipped with TopSpin 4.0.8 software. Samples were prepared by dissolving the compound in deuterated dimethyl sulfoxide with 0.05% (v/v) tetramethylsilane (TMS). Spectra were collected using 16 scans at 298 K.

Polarized Light Microscopy (PLM)

Samples were analyzed using an Olympus BX53 polarized light microscope.

There are four lens options including, 4×, 10×, 25× and 50× magnification.

To capture images the Olympus BX53 is equipped with a PAXcam3 digital microscope camera. The camera has a 3.1-megapixel, 2048×1536-pixel resolution and mounted with camera adapter with 0.5× magnification.

Karl Fischer Titration (KF)

A Mettler Toledo DL39 Coulometric KF Titrator was used to determine the apparent water content in samples. About 90-100 mg of the solid was used for titration. To limit the exposure of the solution to the air, the titrator opening was closed by a stopper immediately after adding samples. HYDRANAL-Coulomat AD was used as the titrant added at 40% speed. The mixing time used was 30 seconds prior to analysis.

Polarized Light Microscopy (UPLC)

The purity of the sample was determined using the method provided by the Analytical Development at JM.

Data were collected using an Agilent 12900 Series UPLC system and analyzed using Chemstation software.

Example 1. Exemplary Preparation of Form 1

An exemplary Form 1 of VS-6766 was prepared according to the synthetic scheme below and Flow Diagram as shown in FIG. 1A, e.g., at a batch size of about 3300 g Compound A.

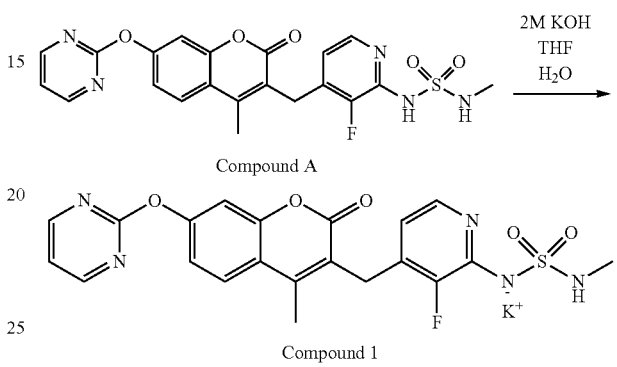

In summary, potassium hydroxide solution was added to a solution of Compound A in THF/Water over about 15 minutes at about 15±5° C., heated to about 55±5° C. and stirred at about 55±5° C. for about 1 hour. The mixture was then cooled to about 20±5° C. and charged with THF gradually. The mixture was further cooled to −5±5° C. then stirred. The resulting precipitate was filtered. The reactor was rinsed with THF/water and filtered over the solid. The reactor was rinsed with THF and then filtered over the solid as a wash. The filtered solid was dried at elevated temperature (e.g., in an oven at about 35° C.) to produce Compound 1 as Form 1.

An exemplary Form 1 produced according to the above method comprises not more than 1.0% of Compound B:

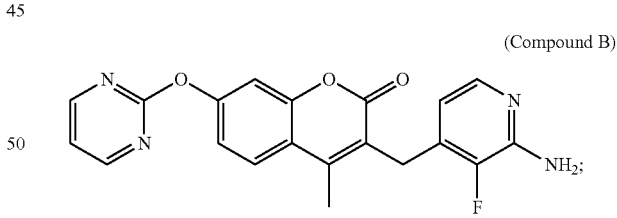

not more than 0.8% of Compound C:

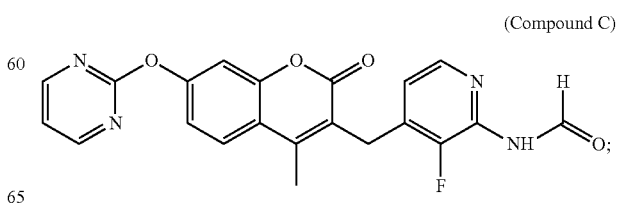

not more than 0.25% of Compound D:

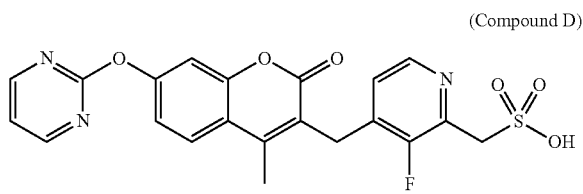 [SMILES: Cc1c(Cc2ccnc(CS(=O)(=O)O)c2F)c(=O)oc2cc(Oc3ncccn3)ccc12]
(Compound D)

as determined by HPLC.

An exemplary Form 1 produced according to the above method comprises not more than 3.0% of total impurities as determined by HPLC. In addition, water content of the exemplary Form 1 was not more than 1.0% as determined by Karl-Fisher (KF) analysis.

Other exemplary batches of Form 1 prepared according the synthetic scheme above to produce about 350 g, 450 g, or 1.3 g of Compound 1 comprised 0.92% total impurities (of which 0.43% was Compound B; 0.42% was Compound C; 0.07% was Compound D) as determined by HPLC and 0.17% water content as determined by Karl-Fisher analysis; 0.94% total impurities (of which 0.36% was Compound B; 0.47% was Compound C; 0.11% was Compound D) as determined by HPLC and 0.12% water content as determined by Karl-Fisher analysis; and 1.2% total impurities (of which 0.47% was Compound B; 0.62% was Compound C; 0.12% was Compound D) as determined by HPLC and 0.3% water content as determined by Karl-Fisher analysis, respectively.

Example 2. Solid Forms of Compound 1

A polymorph screen was performed on Compound 1 including ripening/slurrying at desired temperatures (e.g., RT (room temperature, about 20-25° C.) and 50° C.), heat/cool cycles, cooling of saturated solutions and anti-solvent addition. 10 forms/patterns were observed from screening including two anhydrates (Form 1 and Form 8), a hydrate (Form 10) and seven metastable forms (Patterns 2, 3, 5, 6, 7, 11 and 12).

Figure 4:
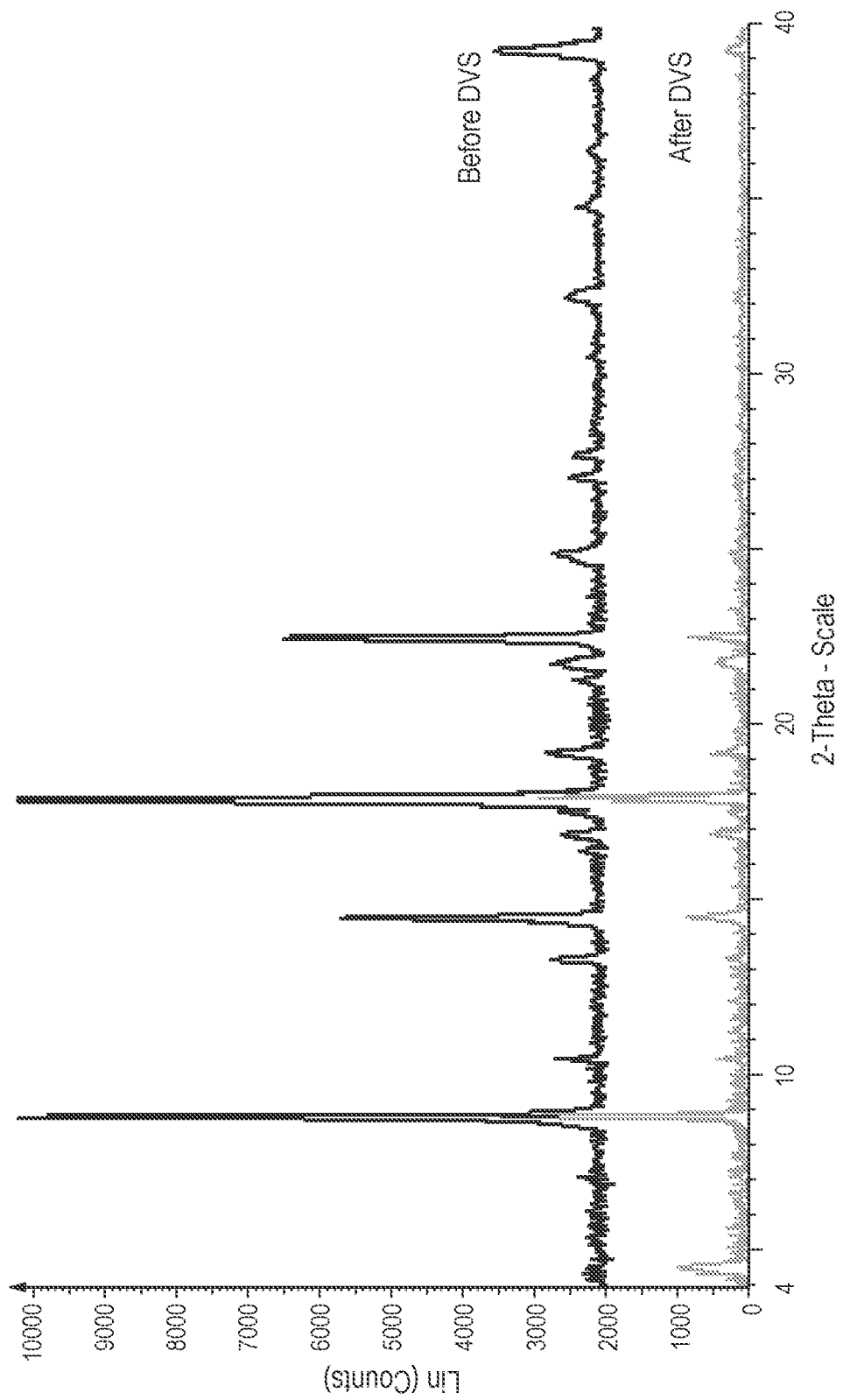
FIG. 4 shows an exemplary XRPD pattern of Form 1 before and after DVS.
Figure 5:
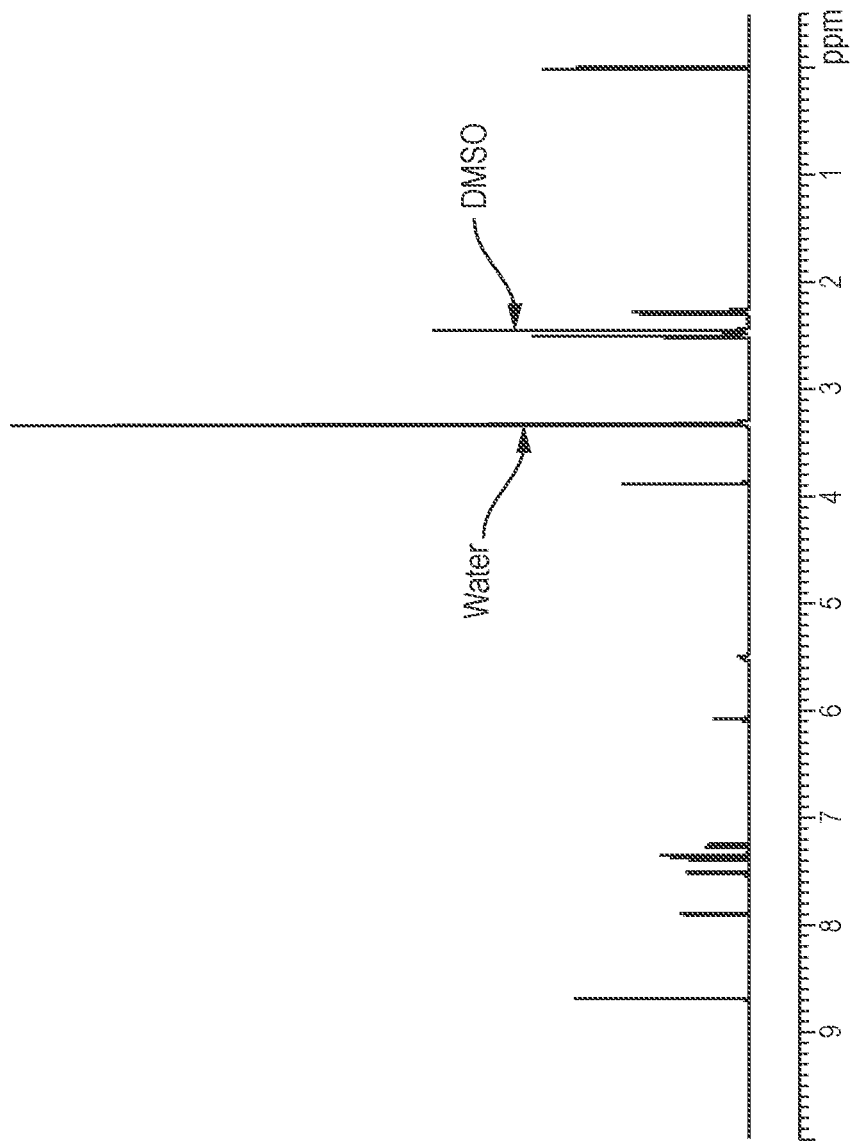
FIG. 5 shows an exemplary 1H NMR spectrum of Form 1 in DMSO-d6.

FIG. 1B shows an exemplary XRPD pattern of Form 1 prepared according to Example 1. DSC and TGA were performed on Form 1. A weight loss of 0.4% was observed by TGA prior to the melt (FIG. 2). DSC shown in FIG. 2 indicates an endotherm starting from 255° C., which indicates the melting of Compound 1. Material was slightly hygroscopic, with about 1.8% weight change between 0-90% RH as shown in FIG. 3. At above 80% RH, significant weight gain was observed (>1% gain observed between 80-90% RH). Weight gain at 90% RH did not stabilize after 120 minutes. FIG. 4 indicates that there was no form change after DVS. The 1H NMR spectrum shown in FIG. 5 was consistent with the structure. No impurities or residual solvents were observed in the sample. Table 1A shows the XRPD peaks of Form 1. Preferred orientation of the crystals can cause variation in peak intensity. Table 1B shows the XRPD peaks of Form 1, corresponding to XRPD pattern of Form 1 (FIG. 1C). Peaks with greater than 3% relative intensity were included.

TABLE 1A

XRPD peak list of Form 1 (FIG. 1B)

| Angle (°2θ) | Intensity % |
| --- | --- |
| 8.8 | 75.9 |
| 10.5 | 6.5 |
| 13.3 | 5.1 |
| 14.5 | 26.7 |
| 16.9 | 4.2 |
| 17.9 | 100.0 |
| 19.2 | 6.3 |
| 21.3 | 3.4 |
| 21.8 | 5.7 |
| 22.5 | 33.0 |
| 24.9 | 6.3 |
| 27.1 | 3.8 |
| 27.8 | 3.2 |
| 32.2 | 4.7 |
| 34.8 | 3.1 |
| 39.3 | 11.8 |

TABLE 1B

XRPD peak list of Form 1 (FIG. 1C)

| Angle (°2θ) | Intensity % |
| --- | --- |
| 4.5 | 97.9 |
| 7.3 | 10.3 |
| 9.0 | 100.0 |
| 10.7 | 8.2 |
| 13.5 | 4.0 |
| 14.7 | 25.0 |
| 16.6 | 3.1 |
| 17.1 | 11.3 |
| 17.7 | 9.8 |
| 18.1 | 71.1 |
| 19.4 | 14.7 |
| 21.9 | 9.7 |
| 22.7 | 22.8 |
| 23.1 | 5.9 |
| 25.1 | 8.8 |
| 27.0 | 4.3 |
| 32.3 | 5.6 |
| 39.4 | 11.3 |

Figure 6:
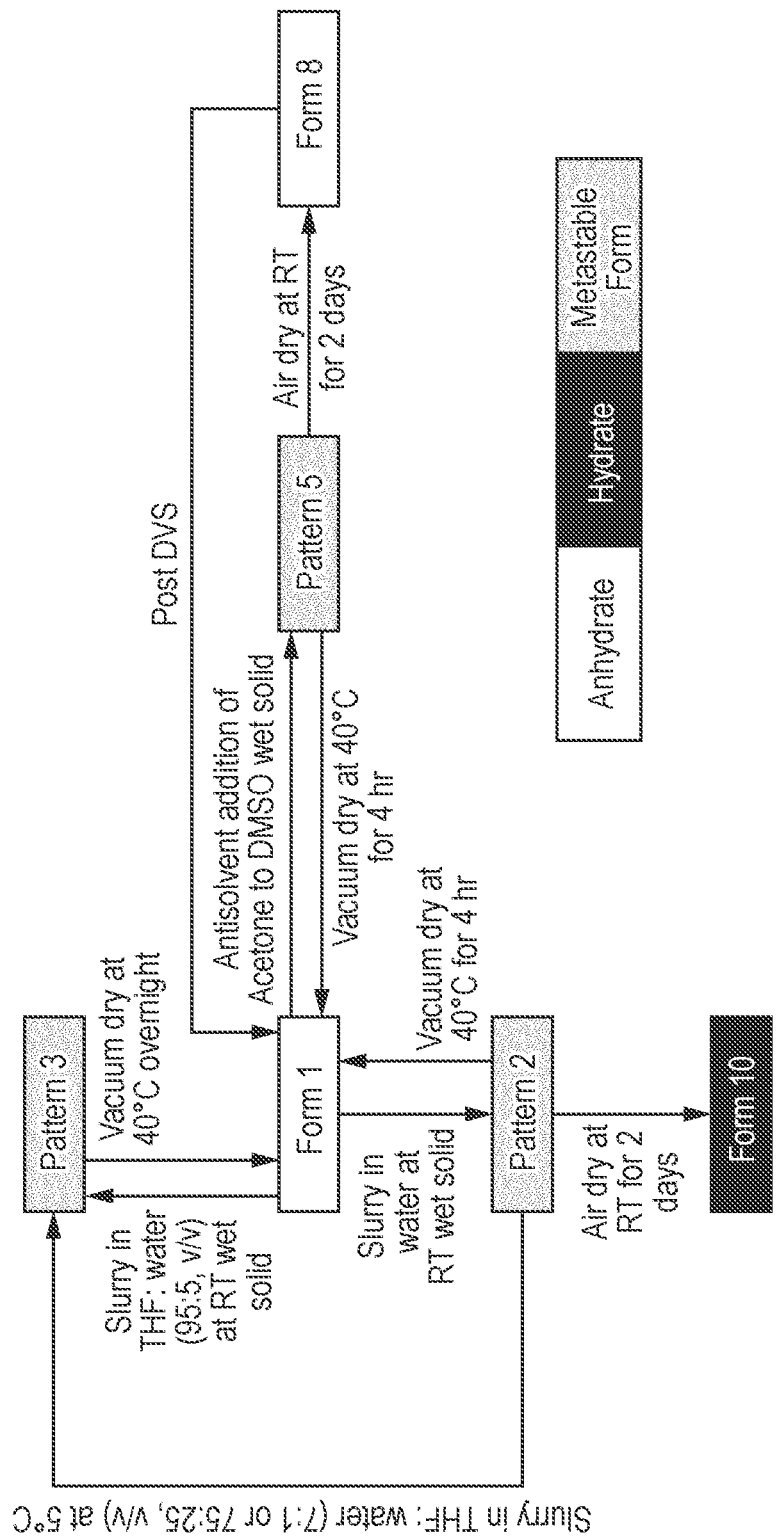
FIG. 6 shows an exemplary form diagram for Compound 1.

FIG. 6 illustrates the relationships among all forms and patterns observed from polymorph screen. Table 2 summarizes the patterns and forms that were observed in the polymorph screening.

TABLE 2

Summary of polymorphs identified during polymorph screen

| Pattern/Form | Method | Polymorphic nature | Conversions (if applicable) |
| --- | --- | --- | --- |
| Form 1 | Prepared according to Example 1 | Anhydrate | — |
| Pattern 2 | Slurry in water at RT wet solid | Metastable | Dry* sample converted to Form 1, however, Pattern 2 ended up with Form |

TABLE 2-continued

Summary of polymorphs identified during polymorph screen

| Pattern/Form | Method | Polymorphic nature | Conversions (if applicable) |
|---|---|---|---|
| Pattern 3 | Slurry in THF:water (95:5, v/v) at RT | Metastable | 10 by air drying for 2 days wet solid Dry* sample converted to Form 1 |
| Pattern 4 | Vacuum drying Pattern 3* | Form 1 | — |
| Pattern 5 | Antisolvent addition of acetone/MEK/THF/toluene to DMSO wet solid | Metastable | Dry* sample converted to Form 1 or Form 8 |
| Pattern 6 | Antisolvent addition of dioxane to DMSO wet solid | Metastable | Dry* sample converted to Form 1 |
| Pattern 7 | Antisolvent addition of DCM/EtOAc/EtOH to DMSO wet solid | Metastable | Dry* sample converted to Form 1 |
| Form 8 | Antisolvent addition of acetone to DMSO dry solid (Dried Pattern 5) | Anhydrate | Post-DVS sample converted to Form 1 |
| Pattern 9 | Antisolvent addition of water to DMF wet and dry solid | — | — |
| Form 10 | Temperature cycling in THF:water (1:1, v/v) dry sample (Air dried Pattern 2) | Hydrate | — |
| Pattern 11 | Temperature cycling in DMF:IPAc (1:2, v/v) or DMF:THF (1:2, v/v) or NMP: Toluene (1:2, v/v) or NMP:IPA (1:2, v/v) | Metastable | Dry* sample converted to Form 1 |
| Pattern 12 | Cooling in DMSO:water (1:1, v/v) or DMSO:MeOH (1:1, v/v) from 50° C. to 5° C. at the rate of 0.1° C./min | Metastable | Dry* sample converted to Form 1 |

*Drying condition: 40° C. under vacuum for 4 hr

Synthesis and Characterization of Pattern 2 and Form 10

Figure 9:
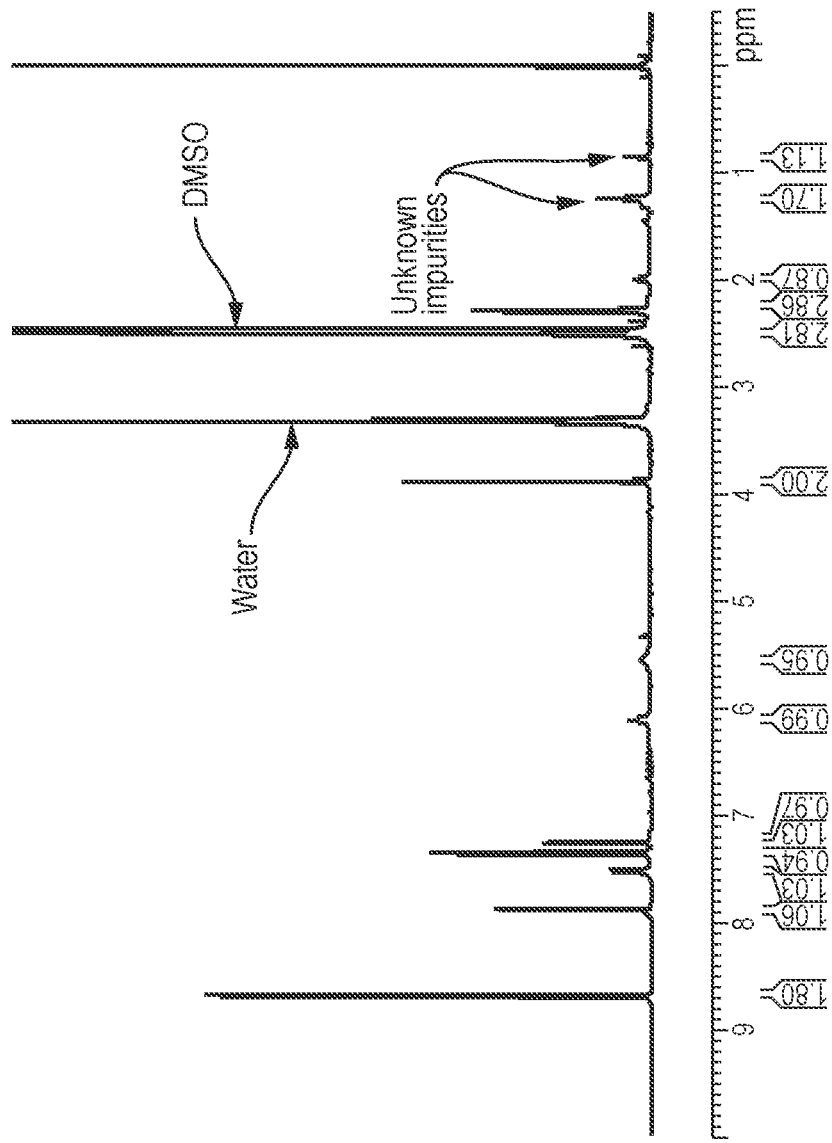
FIG. 9 shows an exemplary 1H NMR spectrum of Form 10.
Figure 11:
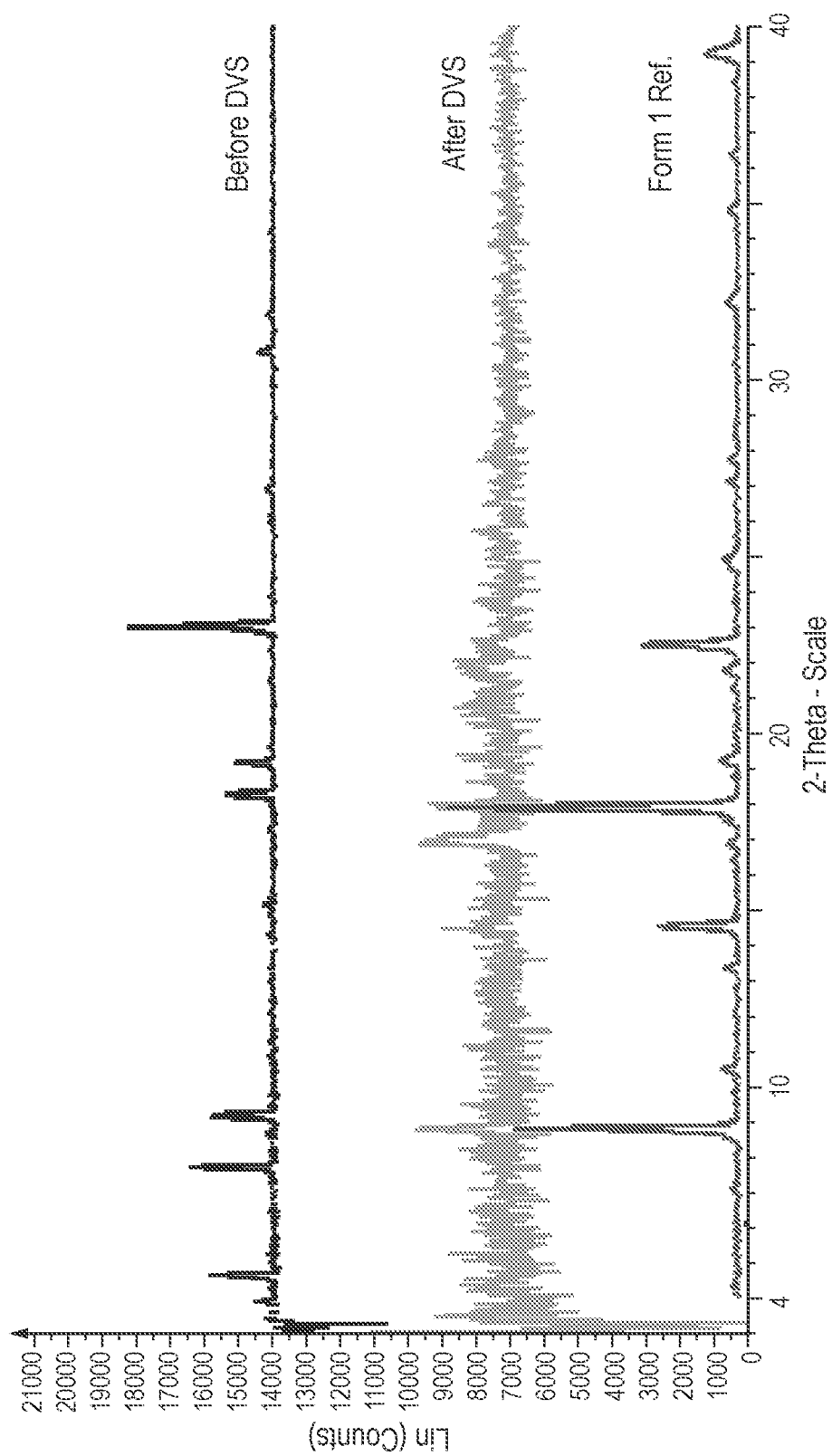
FIG. 11 shows an exemplary XRPD pattern of Form 10 after DVS.

Pattern 2 was generated by stirring (~50 mg) Compound 1 in 0.5 mL water at room temperature (RT) over the weekend. The solid was isolated by centrifuge and analyzed by XRPD (FIG. 7). Pattern 2 converted to Form 1 by vacuum drying at 40° C. for 4 hr, while Pattern 2 converted to Form 10 by air drying (in the isolator) at RT for two days. Form 10 was further characterized. FIG. 7 shows the XRPD of Form 10. In FIG. 8, two endotherms with onset temperatures at 39.4 and 243.4° C. corresponded to dehydration and melting of the API, respectively. TGA thermogram showed a weight loss of 8.5% due to water loss. The NMR spectrum of Form 10 (FIG. 9) was consistent with that of the starting material. Furthermore, KF showed that there was 3.0% water in the sample. FIG. 10 indicated that Form 10 was hygroscopic, with about 5.5% weight change between 0-90% RH. After DVS, Form 10 converted to Form 1 as shown in FIG. 11. Table 3 shows the XRPD peaks of Form 10.

TABLE 3

XRPD peaks of Form 10

| Angle (°2θ) | Intensity % |
|---|---|
| 5.1 | 9.4 |
| 10.4 | 7.6 |
| 11.7 | 79.3 |
| 12.0 | 20.4 |
| 12.5 | 65.7 |
| 13.7 | 9.3 |
| 14.4 | 7.6 |
| 15.3 | 7.3 |
| 16.7 | 28.0 |
| 17.0 | 15.8 |
| 17.3 | 13.5 |
| 17.9 | 19.4 |
| 18.4 | 6.5 |
| 19.0 | 14.4 |
| 19.4 | 19.6 |
| 20.7 | 10.9 |
| 22.5 | 7.7 |
| 23.8 | 41.5 |
| 24.4 | 42.0 |
| 25.5 | 100.0 |
| 27.2 | 8.0 |
| 30.0 | 24.0 |
| 32.6 | 6.9 |
| 38.2 | 7.8 |
| 38.8 | 15.2 |

Synthesis and Characterization of Pattern 3 and Pattern 4

Pattern 3 was generated by stirring (~50 mg) Compound 1 in 0.5 mL THF:water (95:5, v/v) at RT over the weekend. The solid was isolated by centrifuge and analyzed by XRPD (FIG. 12B). Furthermore, Pattern 3 converted to Pattern 4 by vacuum drying at 40° C. for 4 hr. Pattern 4 is consistent with Form 1, when temperature is taken into consideration (FIG. 12A).

Synthesis and Characterization of Pattern 5 and Form 8

Figure 15:
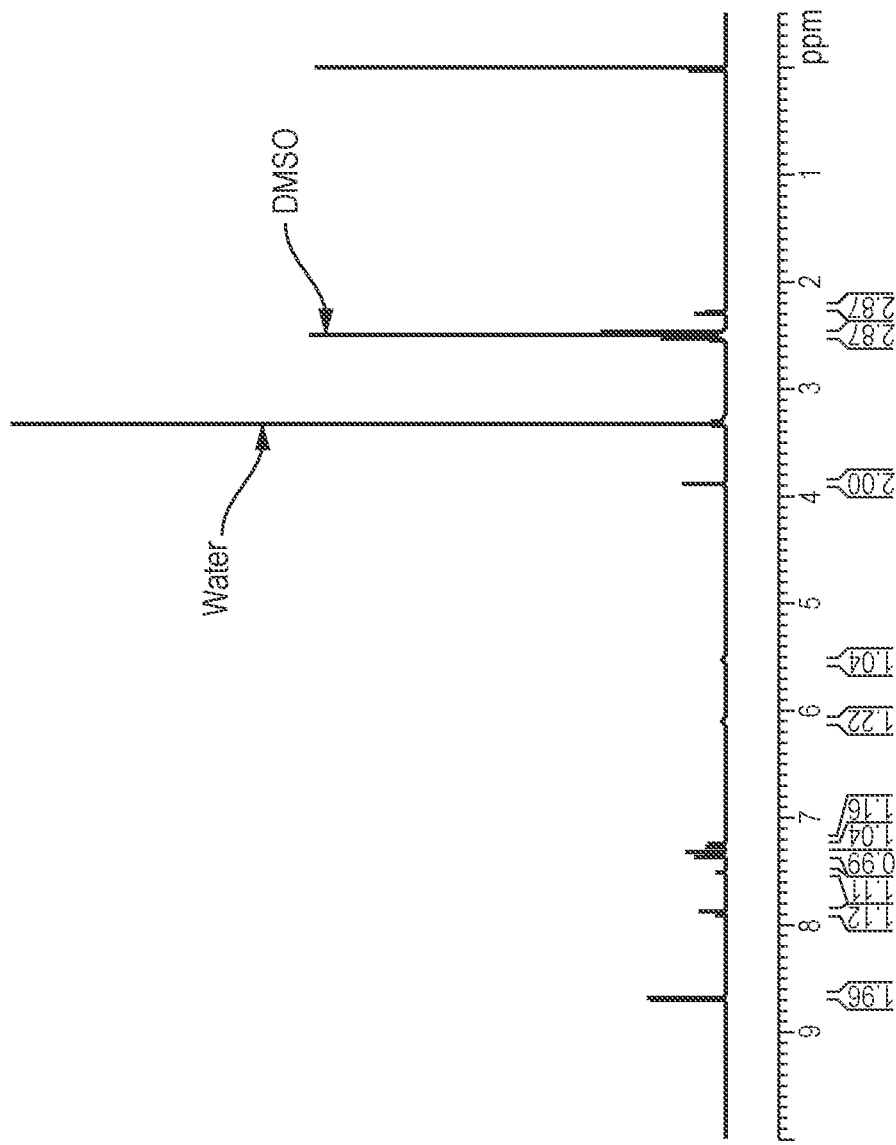
FIG. 15 shows an exemplary 1H NMR spectrum of Form 8.
Figure 16:
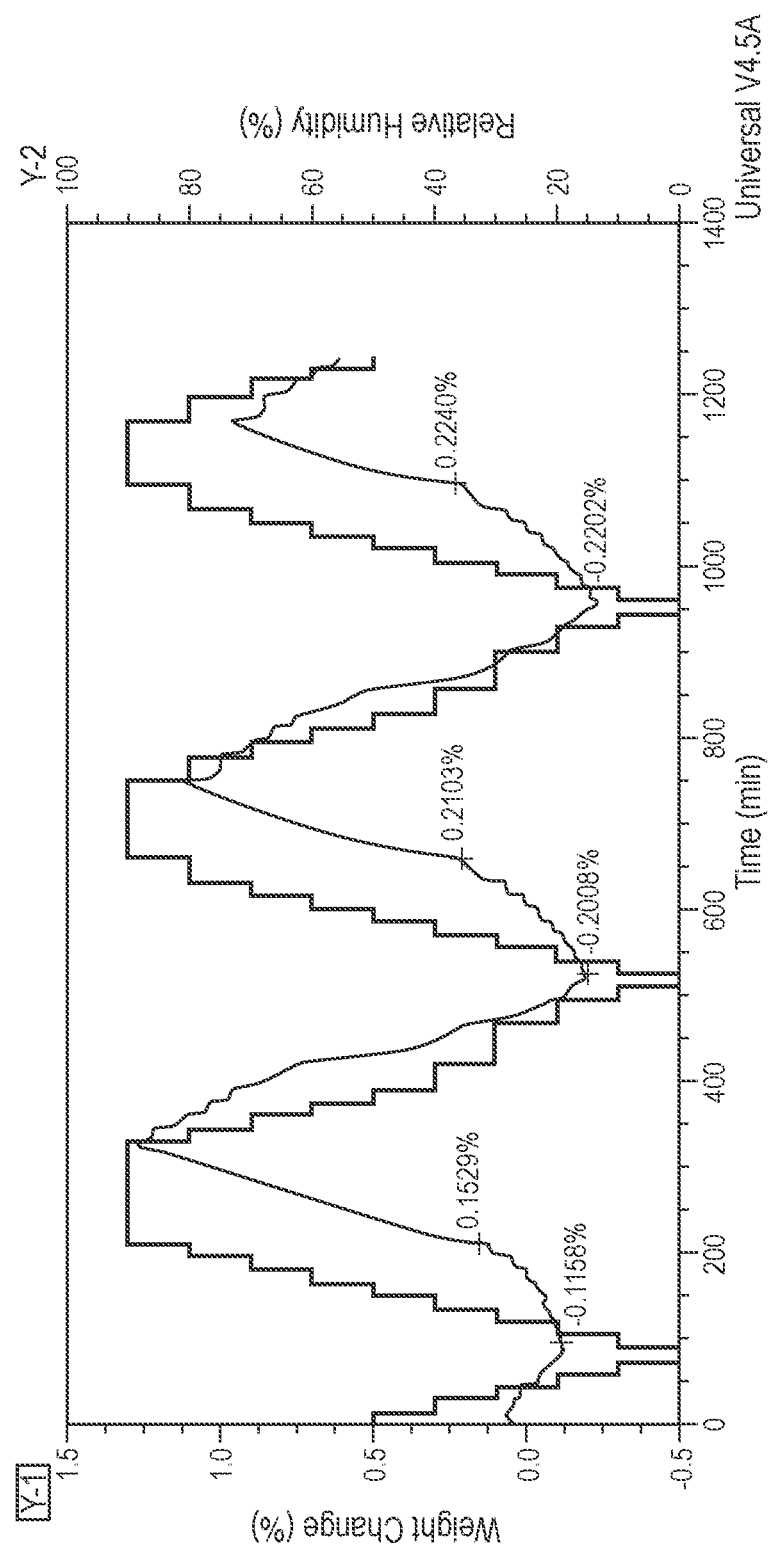
FIG. 16 shows an exemplary DVS pattern of Form 8.
Figure 17:
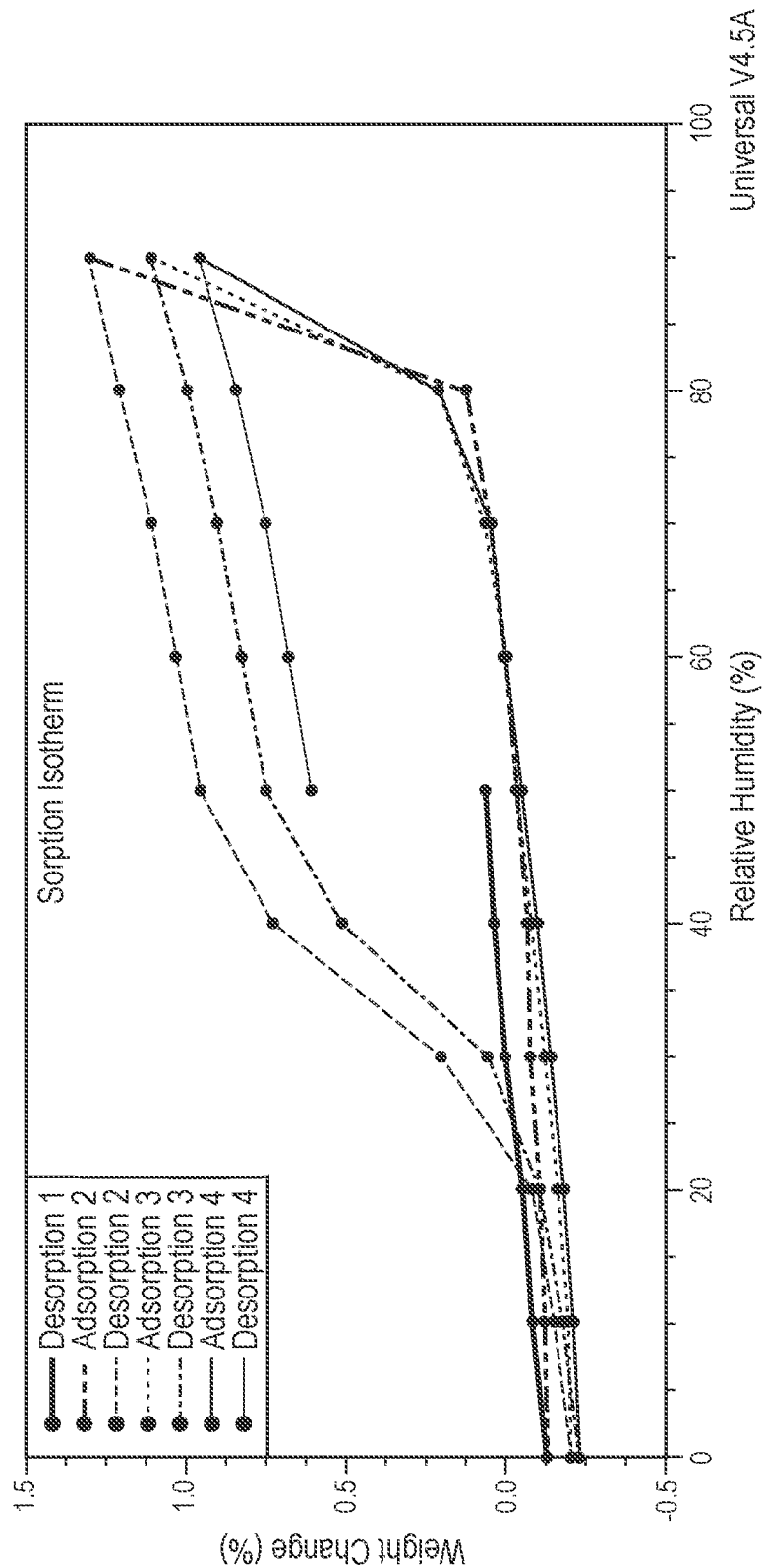
FIG. 17 shows an exemplary sorption isotherm of Form 8.
Figure 18:
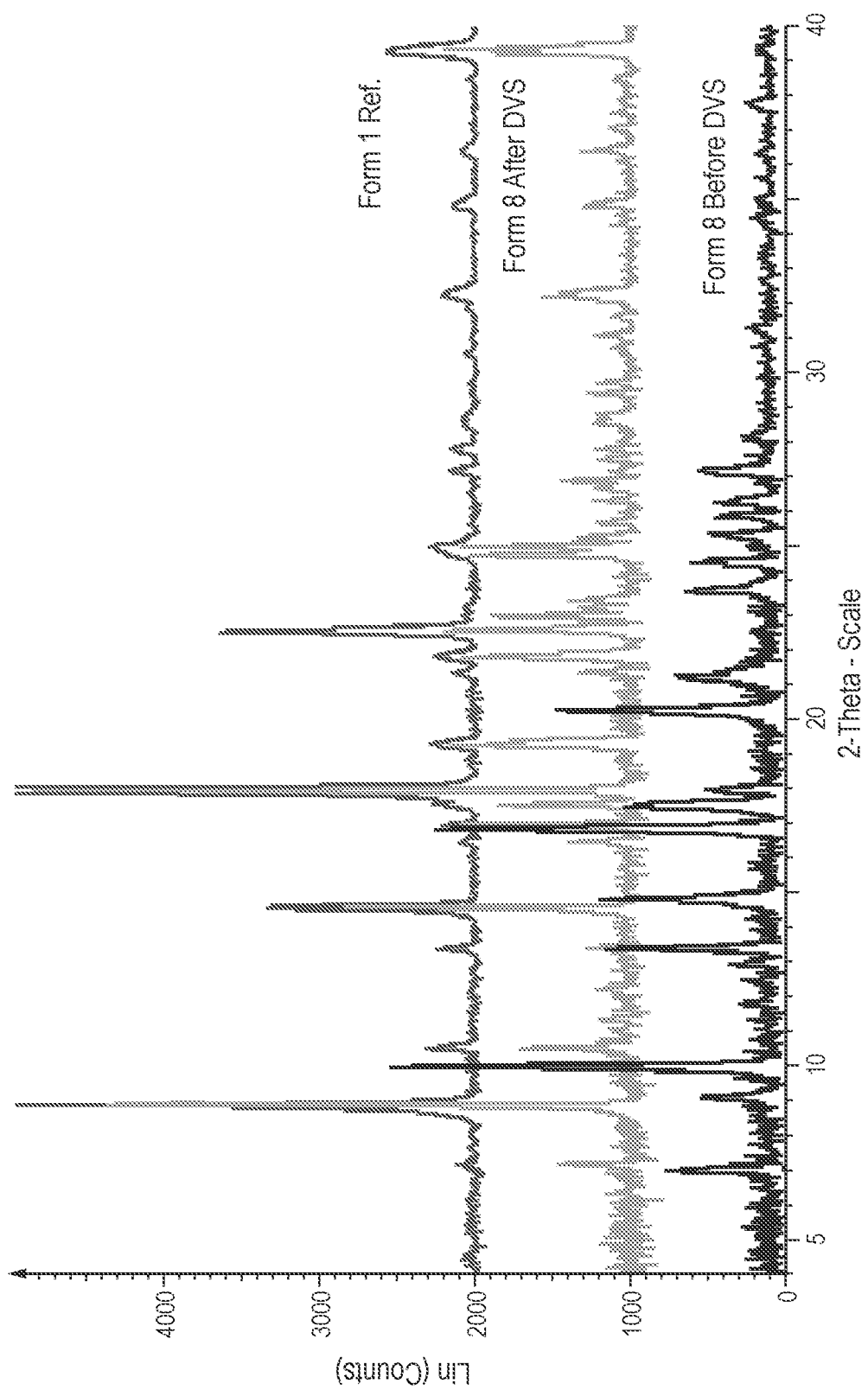
FIG. 18 shows an exemplary XRPD pattern of Form 8 after DVS.

Pattern 5 was generated by antisolvent addition of acetone to a solution of the Compound 1 in DMSO. 575 mg of Compound 1 was dissolved in 5 mL of DMSO at RT. 0.4 mL of DMSO solution was taken and 3.2 mL (8 vol.) of acetone was added to DMSO solution dropwise. Precipitation was observed after acetone was added. The solid was isolated by vacuum filtration and analyzed by XRPD (FIG. 13). Furthermore, Pattern 5 converted to Form 8 by vacuum drying at 40° C. for 4 hr. Form 8 was further characterized. The wet and dry samples from antisolvent addition of acetone to DMSO showed different XRPD patterns as displayed in FIG. 13. In FIG. 14, only one exotherm at 252.7° C. (onset) was observed and TGA thermogram showed a negligible weight loss. The NMR spectrum of Form 10 was consistent with that of the starting material (FIG. 15). Furthermore, KF showed that there was only 0.1% water in the sample. The DVS results (FIG. 16 and FIG. 17) showed that Form 8 was slightly hygroscopic, with up to 0.44% weight change between 0-80% RH. At above 80% RH, at least 1.12% weight gain was observed (>0.27% gain observed between 80-90% RH). After DVS, Form 8 converted to Form 1 as displayed in FIG. 18. Table 4 shows XRPD peaks of Form 8.

TABLE 4

XRPD peak list of Form 8

| Angle (°2θ) | Intensity % |
| --- | --- |
| 4.6 | 6.1 |
| 5.2 | 7.7 |
| 6.9 | 27.8 |
| 7.7 | 6.8 |
| 8.5 | 6.2 |
| 9.0 | 20.0 |
| 9.9 | 100.0 |
| 10.3 | 8.2 |
| 11.7 | 8.6 |
| 12.4 | 8.2 |
| 12.9 | 13.1 |
| 13.3 | 43.5 |
| 14.2 | 6.1 |
| 14.8 | 45.1 |
| 16.8 | 87.7 |
| 17.5 | 40.8 |
| 17.9 | 19.3 |
| 20.2 | 57.6 |
| 21.2 | 26.1 |
| 23.1 | 6.5 |
| 23.7 | 23.2 |
| 24.5 | 20.5 |
| 25.3 | 16.7 |
| 25.8 | 9.9 |
| 26.2 | 15.5 |
| 27.1 | 19.6 |
| 28.2 | 7.7 |
| 31.2 | 7.1 |
| 37.8 | 6.4 |

Synthesis and Characterization of Pattern 6

Pattern 6 was generated by antisolvent addition of dioxane to a solution of the Compound 1 in DMSO. 575 mg of Compound 1 was dissolved in 5 mL of DMSO at RT. 0.4 mL of DMSO solution was taken and 8.0 mL (20 vol.) of acetone was added to DMSO solution dropwise. Precipitation was observed after stirring the samples at RT for about 20 min. The solid was isolated by vacuum filtration and analyzed by XRPD (FIG. 19). Furthermore, Pattern 6 converted to Form 1 by vacuum drying at 40° C. for 4 hr.

Synthesis and Characterization of Pattern 7

Pattern 7 was generated by antisolvent addition of DCM to a solution of the Compound 1 in DMSO. 575 mg of Compound 1 was dissolved in 5 mL of DMSO at RT. 0.4 mL of DMSO solution was taken and 2.4 mL (6 vol.) of DCM was added to the DMSO solution dropwise. Precipitation was observed after DCM has been added. The solid was isolated by vacuum filtration and analyzed by XRPD (FIG. 20). Furthermore, Pattern 7 converted to Form 1 by vacuum drying at 40° C. for 4 hr.

Synthesis and Characterization of Pattern 9

Figure 22:
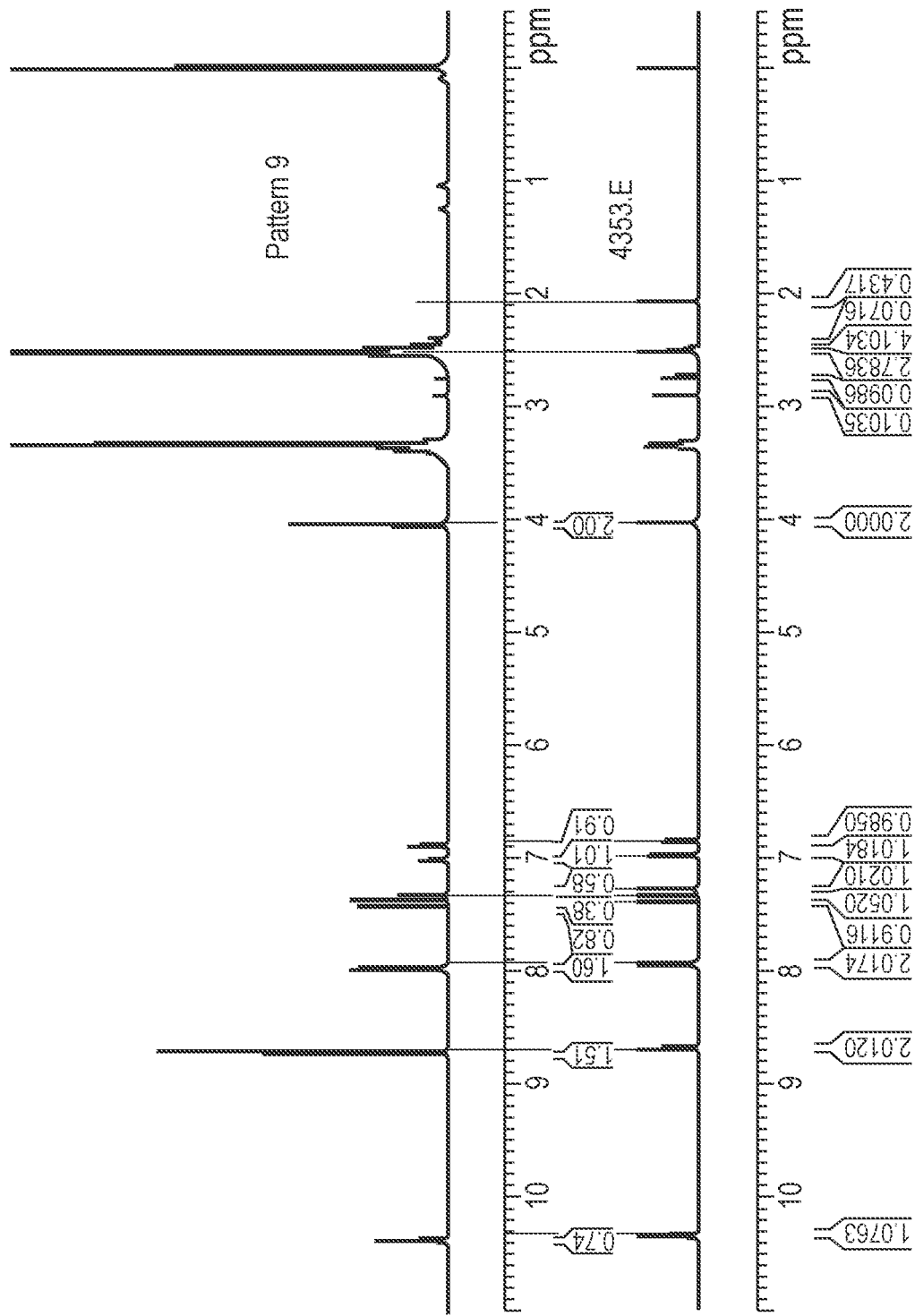
FIG. 22 shows an exemplary 1H NMR spectrum of Pattern 9.

Pattern 9 was generated by antisolvent addition of water to a solution of the Compound 1 in DMF. 547 mg of Compound 1 was dissolved in 14 mL of DMF at RT. 1.0 mL of DMF solution was taken and 12 mL (12 vol.) of water was added to the DMF solution dropwise. Precipitation was observed after stirring the sample at RT for 15 min. The solid was isolated by vacuum filtration and analyzed by XRPD (FIG. 21). Both wet and dry samples yielded Pattern 9, which matched the XRPD pattern of VS-6766 (free form). The NMR spectrum of Pattern 9 (FIG. 22) matched that of VS-6766 (free form).

Synthesis and Characterization of Pattern 11

Pattern 11 was generated by temperature cycling of DMF:IPAc (1:2, v/v) sample: about 50 mg of Compound 1 was charged to 0.3 mL of DMF:IPAc (1:2, v/v) to form a suspension. The suspension was heated to 50° C. at the heating rate of 5° C./min and held for 30 min; and then cooled to 5° C. at the rate of 0.1° C./min and held for 30 min. The heating and cooling steps were repeated once. The solid was isolated by centrifuge for XRPD analysis. The XRPD pattern is shown in FIG. 23. Pattern 11 converted to Form 1 by drying under vacuum for 4 hr.

Synthesis and Characterization of Pattern 12

Pattern 12 was generated by cooling of DMSO:MeOH (1:1, v/v) solution of Compound 1. About 50 mg of Compound 1 was suspended in 1 mL of DMSO:MeOH (1:1, v/v) at 50° C. and stirred for 2 hr. Clear solution was obtained by filtering the suspension using a 0.45 μL PTFE filter. Then the solution was cooled from 50° C. to 5° C. at a cooling rate of 0.1° C./min. Precipitation was observed at 5° C. Solid was isolated by centrifuge and analyzed by XRPD (FIG. 24). Pattern 12 converted to Form 1 by drying under vacuum for 4 hr.

Example 3. Slurry of Compound 1 at Different Temperatures

Approximately 50 mg of Compound 1 was dispersed in 0.5 mL of the given solvent and slurried for two days at 20° C. The solid was obtained by centrifuge and analyzed by XRPD. If no novel XRPD pattern was observed, the remaining solids were slurried again at 50° C. for two days. Form 1, Pattern 2, Pattern 3 and Pattern 4 were observed from slurry experiments as summarized in Table 5.

TABLE 5

Summary of slurries at 20 and 50° C.

| Solvent system (v/v) | XRPD Slurry 20° C. Wet Solid | XRPD Slurry 20° C. Dry Solid | XRPD Slurry 50° C. Wet Solid |
|---|---|---|---|
| n-Heptane | Form 1 | N/A | Form 1 |
| Ethyl acetate | Form 1 | N/A | Form 1 |
| Isopropyl acetate | Form 1 | N/A | Form 1 |
| MIBK | Form 1 | N/A | Form 1 |
| IPA | Form 1 | N/A | Form 1 |
| MEK | Form 1 | N/A | Form 1 |
| Acetone | Form 1 | N/A | Form 1 |
| Ethanol | Form 1 | N/A | Form 1 |
| DMSO | N/A | N/A | N/A |
| Water | Pattern 2 | Form 1 | N/A |
| TBME | Form 1 | N/A | Form 1 |
| 1,4-dioxane | Form 1 | N/A | Form 1 |
| Toluene | Form 1 | N/A | Form 1 |
| THF | Form 1 | N/A | Form 1 |
| DCM | Form 1 | N/A | N/A |
| MeOH | Form 1 | N/A | Form 1 |
| DMF | Form 1 | N/A | Form 1 |
| MeCN | Form 1 | N/A | Form 1 |
| NMP | Form 1 | N/A | N/A |
| THF:water (95:5) | Pattern 3 | Pattern 4 | N/A |
| THF:water (75:25) | Form 1 | N/A | Pattern 2 |
| IPA:water (95:5) | Form 1 | N/A | Form 1 |
| IPA:water (75:25) | Form 1 | N/A | Pattern 2 |
| Acetone:water (95:5) | Form 1 | N/A | Form 1 |

Example 4. Antisolvent Additions to Compound 1

DMSO, NMP and DMF were selected as the solvents to prepare Compound 1 solution. Compound 1 solutions of each solvent were prepared at RT (DMSO: solution concentration of 115 mg/mL; NMP: solution concentration of 59 mg/mL; DMF: solution concentration of 46 mg/mL). The prepared solution was distributed to 10 vials for each antisolvent additions. The details of antisolvent and the corresponding XRPD results are respectively summarized in Table 6.

TABLE 6

Summary of antisolvent additions

| Solvent | Anti-solvent, volume | Polymorphic nature (XRPD wet) | Polymorphic nature (XRPD dry) |
|---|---|---|---|
| DMSO | Acetone, 8 vol | Pattern 5 | Form 8 |
| DMSO | MeCN, 4 vol | Form 1 | N/A |
| DMSO | DCM, 6 vol | Pattern 7 | Form 1 |
| DMSO | Dioxane, 20 vol | Pattern 6 | Form 1 |
| DMSO | EtOAc, 8 vol | Pattern 7 | Form 1 |
| DMSO | EtOH, 8 vol | Pattern 7 | Form 1 |
| DMSO | Water, 4 vol | N/A | N/A |
| DMSO | MEK, 6 vol | Pattern 5 | Form 1 |
| DMSO | THF, 10 vol | Pattern 5 | Form 1 |
| DMSO | Toluene, 6 vol | Pattern 5 | Form 1 |
| NMP | Acetone, 15 vol | Pattern 5 | — |
| NMP | MeCN, 10 vol | Pattern 5 | — |
| NMP | TBME, 2 vol | N/A | — |
| NMP | Dioxane, 15 vol | Pattern 5 | — |
| NMP | IPAc, 3 vol | Pattern 5 | — |
| NMP | MeOH, 15 vol | N/A | — |
| NMP | water, 15 vol | Low crystallinity | — |
| NMP | MEK, 6 vol | Pattern 5 | — |
| NMP | THF, 15 vol | Pattern 5 | — |
| NMP | Toluene, 3 vol | N/A | — |
| DMF | Acetone, 12 vol | Pattern 5 | *Form 1 |

TABLE 6-continued

Summary of antisolvent additions

| Solvent | Anti-solvent, volume | Polymorphic nature (XRPD wet) | Polymorphic nature (XRPD dry) |
|---|---|---|---|
| DMF | MeCN, 12 vol | Pattern 5 | *Form 1 |
| DMF | TBME, 4 vol | Low crystallinity | N/A |
| DMF | Dioxane, 12 vol | Pattern 5 | N/A |
| DMF | EtOAc, 12 vol | Pattern 5 | **Form 1 |
| DMF | EtOH, 12 vol | Pattern 5 | **Form 1 |
| DMF | Water, 12 vol | Pattern 9 | *Pattern 9 |
| DMF | DCM, 12 vol | Pattern 5 | N/A |
| DMF | THF, 12 vol | Pattern 5 | N/A |
| DMF | Toluene, 6 vol | Pattern 5 | N/A |

*Air dry in the isolator for 2 days;
**Vacuum dry at 40° C. for 2 hr

Example 5. Temperature Cycling of Form 1

Approximately 50 mg of Compound 1 was suspended in 0.3 mL of selected solvent systems. The samples were heated to 50° C. at heating rate of 5° C./min and held at 50° C. for 30 min then cooled to 5° C. at the cooling rate of 0.1° C./min and held at 5° C. for 30 min. The heating and cooling steps were repeated and the samples were kept at 5° C. before isolation for XRPD analysis. Table 7 summarizes the results from temperature cycling experiments. Form 1, Pattern 2, Pattern 5, Pattern 11 and low crystallinity were observed.

TABLE 7

Summary of temperature cycling

| Solvent system (v/v) | Polymorphic nature (XRPD wet) | Polymorphic nature (XRPD dry) |
|---|---|---|
| THF:water (1:1) | Pattern 2 | Form 10 |
| IPA:water (1:1) | Pattern 2 | N/A |
| Acetone:water (1:1) | Pattern 2 | Form 10 |
| MeOH:water (1:1) | Pattern 2 | N/A |
| EtOH:water (1:1) | Pattern 2 | N/A |
| MeCN:water (1:1) | Pattern 2 | N/A |
| Dioxane:water (1:1) | Pattern 2 | N/A |
| DMSO:water (1:2) | Pattern 2 | N/A |
| DMF:water (1:2) | Pattern 2 | N/A |
| DMSO:MIBK (1:2) | Form 1 | N/A |
| DMSO:MeCN (1:2) | Low crystallinity | Form 1 |
| DMSO:DCM (1:2) | Low crystallinity | Form 1 |
| DMSO:Dioxane (1:2) | Pattern 5 | N/A |
| DMSO:IPAc (1:2) | Pattern 5 | N/A |
| DMSO:MeOH (1:2) | Form 1 | N/A |
| DMSO:THF (1:2) | Form 1 | N/A |
| DMF:Toluene (1:2) | Form 1 | N/A |
| DMF:MEK (1:2) | Form 1 | N/A |
| DMF:MeCN (1:2) | Form 1 | N/A |
| DMF:Dioxane (1:2) | Form 1 | N/A |
| DMF:IPAc (1:2) | Pattern 11* | Form 1 |
| DMF:THF (1:2) | Pattern 11* | Form 1 |
| NMP:MEK (1:2) | Form 1 | N/A |
| NMP:Toluene (1:2) | Pattern 11* | Form 1 |
| NMP:EtOAc (1:2) | Form 1 | N/A |
| NMP:IPA (1:2) | Pattern 11* | Form 1 |
| NMP:DCM (1:2) | Form 1 | N/A |
| NMP:THF (1:2) | Form 1 | N/A |

*Pattern 11 matches Pattern 2 + XRPD peaks at 16.9, 25.1 and 26.5 2-theta

Example 6. Slow Cooling of Form 1

Suspensions of Compound 1 were prepared at 50° C. and stirred for 2 hr. Clear solutions were obtained by filtering the suspensions with a 0.2 μm PTFE filter and followed by cooling from 50 to 5° C. at a cooling rate 0.1° C./min. The results from slow cooling are shown in Table 8. Form 1, Pattern 2, Form 8 minus some peaks, Pattern 12 and low crystallinity were observed.

TABLE 8

Summary of slow cooling

| Solvent system (v/v) | Polymorphic nature (XRPD wet) | Polymorphic nature (XRPD dry) |
| --- | --- | --- |
| THF:water (1:2) | Pattern 2 | N/A |
| IPA:water (1:2) | Pattern 2 | N/A |
| Acetone:water (1:2) | Pattern 2 | N/A |
| MeCN:water (1:2) | Form 8 | Form 1 |
| Dioxane:water (1:2) | Low crystallinity | Form 1 |
| DMSO:water (1:1) | Low crystallinity | Form 1 |
| DMSO:MIBK (1:1) | Pattern 12 | Form 1 |
| DMSO:MeCN (1:1) | Low crystallinity | Form 1 |
| DMSO:DCM (1:1) | Low crystallinity | Form 1 |
| DMSO:MeOH (1:1) | Pattern 12 | Form 1 |
| DMSO:THF (1:1) | Low crystallinity | Form 1 |
| DMF:Toluene (1:1) | N/A | N/A |
| DMF:MEK (1:1) | N/A | N/A |
| DMF:MeCN (1:1) | N/A | N/A |
| DMF:Dioxane (1:1) | N/A | N/A |
| DMF:IPAc (1:1) | N/A | N/A |
| NMP:Acetone (1:1) | N/A | N/A |
| NMP:EtOAc (1:1) | N/A | N/A |
| NMP:IPA (1:1) | N/A | N/A |
| NMP:DCM (1:1) | N/A | N/A |

Example 7. Stability of Form 1 Under Stressed Conditions

Form 1 solids were stored in 40° C./75% RH or 30° C./65% RH conditions. The XRPD and UPLC purity were measured at week 1 and week 4 time points. The results are summarized in Table 9. The purity determined by UPLC remained statistically unchanged. Additionally, water content was measured by KF at Week 5. The water content was consistent with initial water content.

TABLE 9

Summary of Form 1 stability at stressed conditions

| Conditions | XRPD (Week 1) | Purity (Week 1) | XRPD (Week 4) | Purity (Week 4) | Water content (Week 5) |
| --- | --- | --- | --- | --- | --- |
| 40° C./75% RH | Form 1 | 99.2% | Form 1 | 99.2% | 0.5% |
| 30° C./65% RH | Form 1 | 99.2% | Form 1 | 99.2% | 0.6% |

Example 8. Dosage Forms of VS-6766 Form 1 and Exemplary Manufacturing Process

An exemplary method of manufacturing an oral dosage form of VS-6766 is described. For example, a composition of VS-6766 (0.8 mg based on VS-6766 free form (0.864 mg of VS-6766 corresponds to 0.8 mg of VS-6766 free form), is provided in Table 10.

TABLE 10

Composition of VS-6766 capsules

| Component | Description | Amount per capsule |
| --- | --- | --- |
| VS-6766 | API | 0.864 mg |
| D-mannitol, fine | Filler | 4.136 mg |
| Mannitol, granular | Filler | 93.50 mg |
| Magnesium Stearate | Lubricant | 1.500 mg |
| Hard Hypromellose (HPMC) capsules, capsule size 4 | Capsule shell | 1 capsule |
| | Total without empty capsule | 100.0 mg |
| | Total including empty capsule | 138.0 mg |

Figure 25:
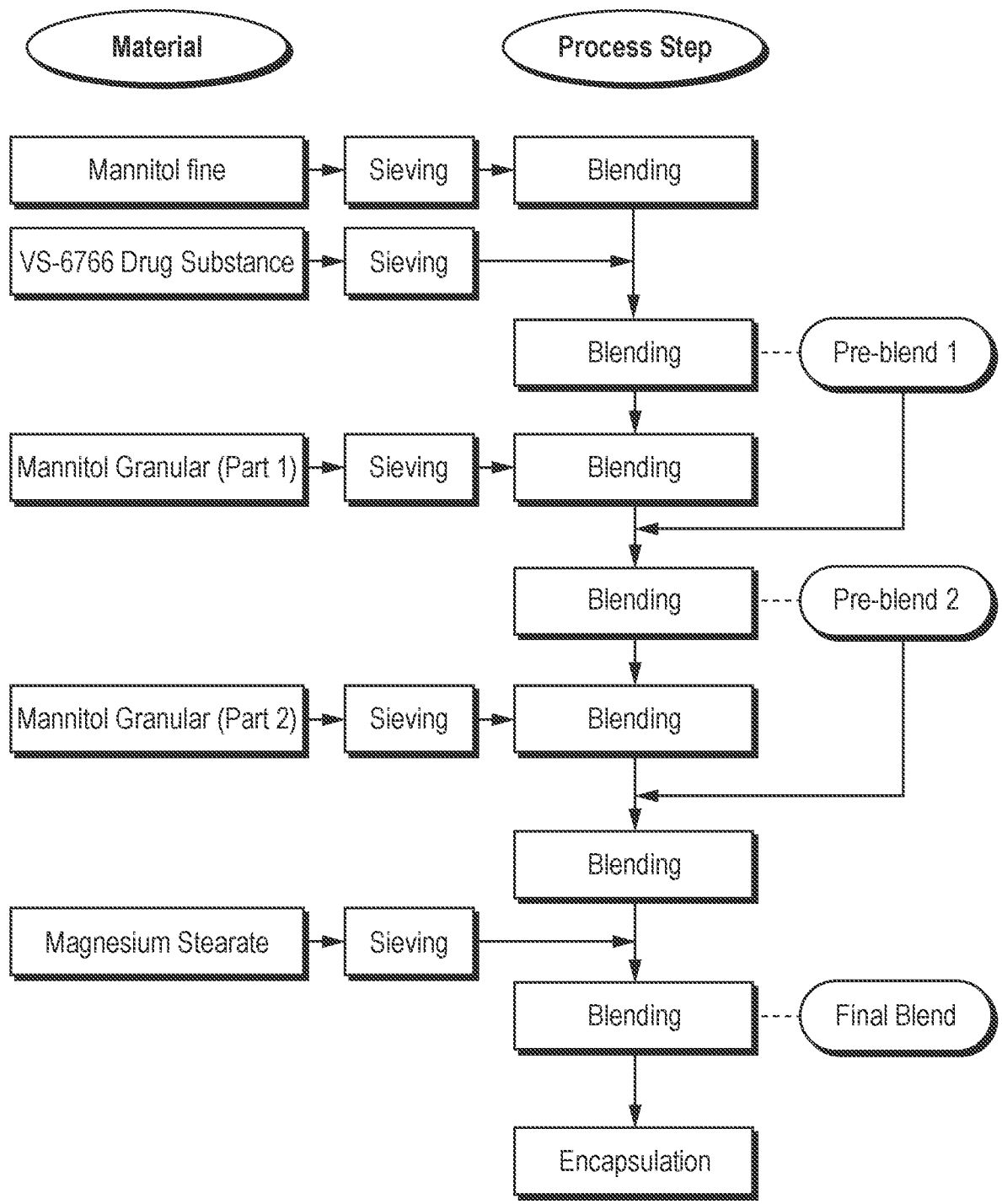
FIG. 25 shows an exemplary flow diagram of the manufacturing process of VS-6766 capsules.

An exemplary manufacturing process of VS-6766 capsules comprises a series of several blending followed by encapsulation of the final blend to produce capsules. Mannitol (fine powder) is sieved via screen 0.150 mm and blended. VS-6766 is sieved and added into blender and blended together with the blend of mannitol (fine) from previous step to yield "pre-blend 1" once blended. Granular mannitol is sieved in two parts (part 1 and part 2) using 0.315 mm screen. The sieved mannitol (part 1) is added to a blender and blended. The pre-blend 1 is added into blender and additionally blended with blended mannitol (part 1) to yield "pre-blend 2" once blended together. The sieved mannitol (part 2) is added to a blender and blended. The pre-blend 2 is added into blender and additionally blended with blended mannitol (part 2). Magnesium stearate is sieved using 0.200 mm screen and added into blender together with the blend (VS-6766, fine mannitol, granular mannitol part 1 and part 2), to yield a "final blend" once blended. Capsules are produced by encapsulating the final blend in size 4 HPMC capsule shells. FIG. 25 shows a flow diagram of the manufacturing process. High-shear blending was employed to blend the materials as conventional blending failed to provide a drug product with suitable content uniformity.

A batch of VS-6766 capsules using a conventional blending (free-fall) approach (Batch A) resulted in fluctuations in blend uniformity during dilution steps, inhomogeneity in the blend after the final lubrication step, low API content in the final blend and in the capsules, and difficulty increasing API content during the end of encapsulation. Another exemplary manufacturing batch (Batch B) using conventional blending approach yielded 40,000 capsules based on 34.56 g of VS-6766. In Batch B, to improve the blend homogeneity and optimize the process compared to Batch A, the API was sandwiched between fine mannitol powder; the screen used for pre-blend 1 was flushed with fine mannitol powder; and pre-blend 1 was sandwiched between granular mannitol to produce pre-blend 2. In addition, the lubricant was not screened onto the complete blend in the blending bin but instead, one aliquot of the blend was taken out of the bin. The lubricant was screened onto this aliquot and then manually blended, and the premixture was added to the remaining blend for lubrication in order to avoid formation of clumps during lubrication. Moreover, the encapsulation was stopped after the powder sensor stopped the machine; no powder was manually transferred in the dosing plate to optimize capsule yield to avoid separation of the blend during encapsulation. For Batch B, pre-blend 1 showed low API content and high RSD (mean 78.8% recovery, RSD 8.8% for n=6). Pre-blend 2 showed low API content (mean 87.1% recovery, RSD 5.5% for n=18). For the final blend, wider fluctuations in blending uniformity across samples were observed (mean 85.74% recovery, RSD 22.4%). The mean API content was below the target, with RSD of over 20% (target: mean assay target, RSD of individual values≤5%).

Assay and content uniformity: Assay and content uniformity were determined via HPLC. Assay (%) for Batches C and D (made using high-shear blending, rather than conventional, direct blending) were 95.1 and 98.2%, respectively, whereas assay (%) for Batches A and B were 79.7 and 80.2%, respectively. Content uniformity samples were taken, for example, every 10 mins during the encapsulation run. The results for content uniformity testing confirmed low API content found during assay testing for Batch A (content uniformity: mean 86.70%, RSD 7.60%) and Batch B (content uniformity: mean 80.48%, RSD 3.47%).

Figure 26:
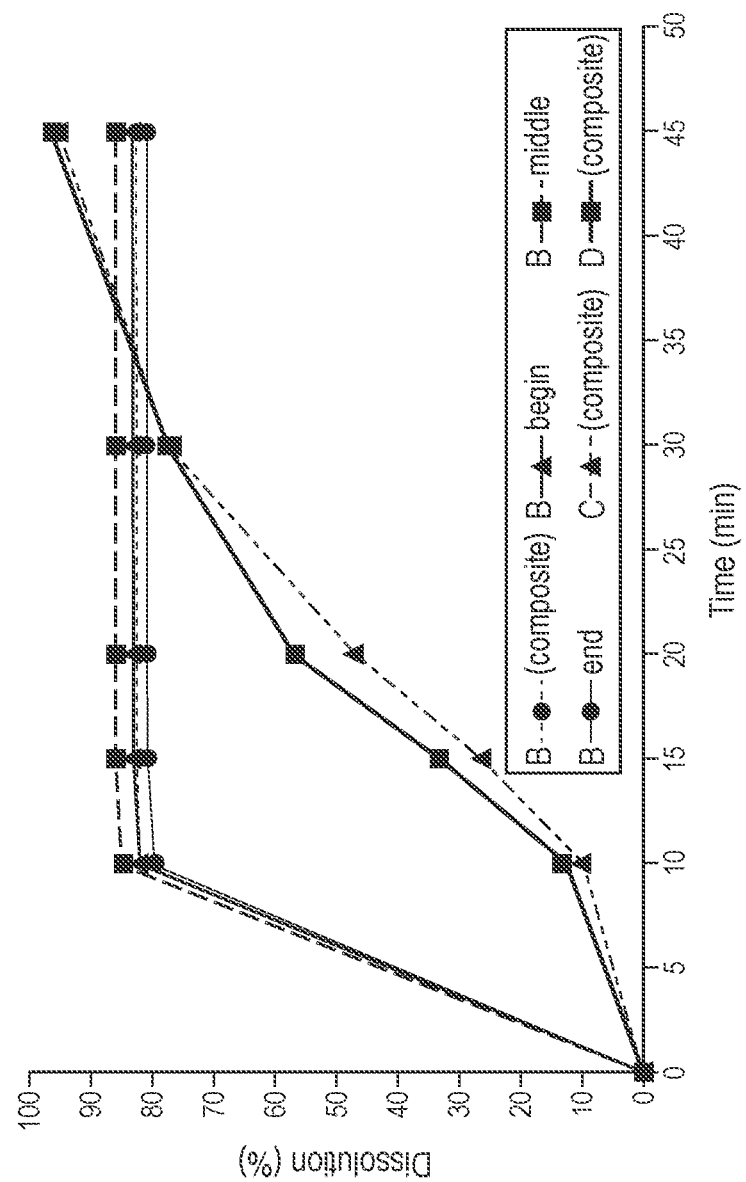
FIG. 26 shows exemplary dissolution profiles of VS-6766 batches.

Dissolution: Compared to Batches C and D, a relatively faster dissolution was observed for Batches A and B. For example, FIG. 26 shows the dissolution profiles of Batches B, C, and D.

Example 9. Single Crystal of Form 1

Single Crystal Growth and Sample Preparation

Form 1 was analyzed by single crystal X-ray diffraction. The crystal was obtained from a DMF solution of Form 1 followed by slow evaporation. The crystal structure was determined at 100(2) K.

Results

Figure 27:
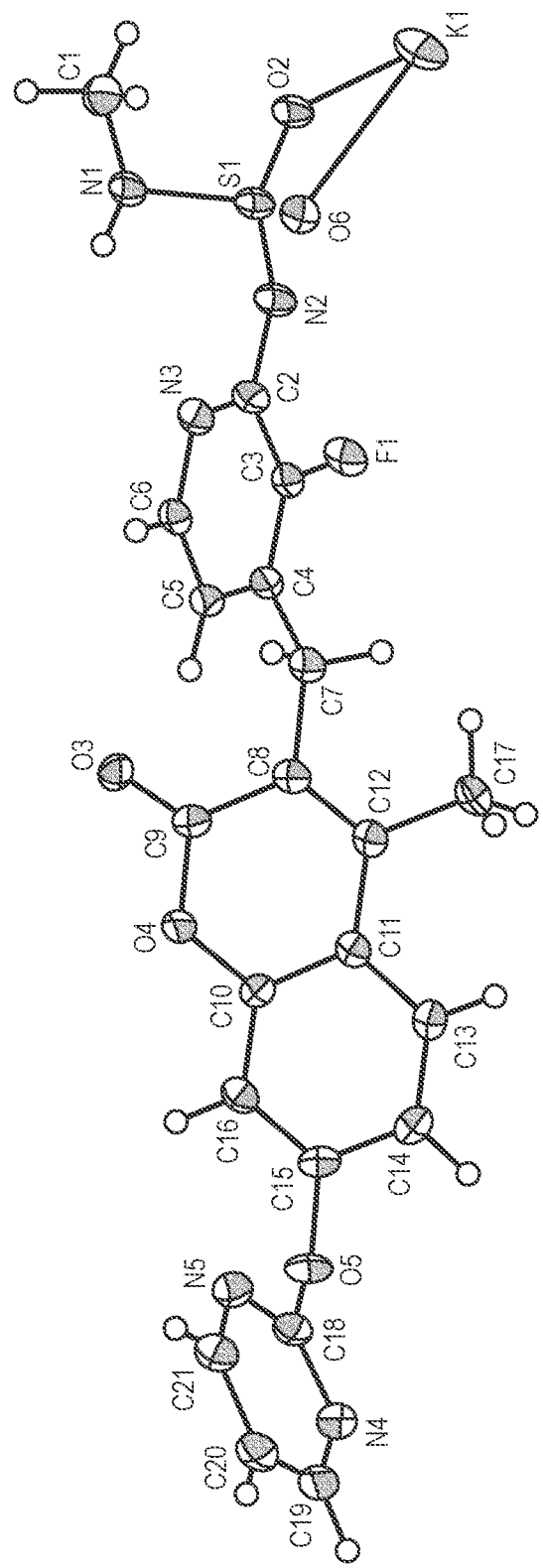
FIG. 27 shows a view of Form 1 from the single crystal X-ray structure showing the atom numbering scheme. Anisotropic atomic displacement ellipsoids for the non-hydrogen atoms are shown at the 50% probability level. Hydrogen atoms are displayed with an arbitrarily small radius.
Figure 28:
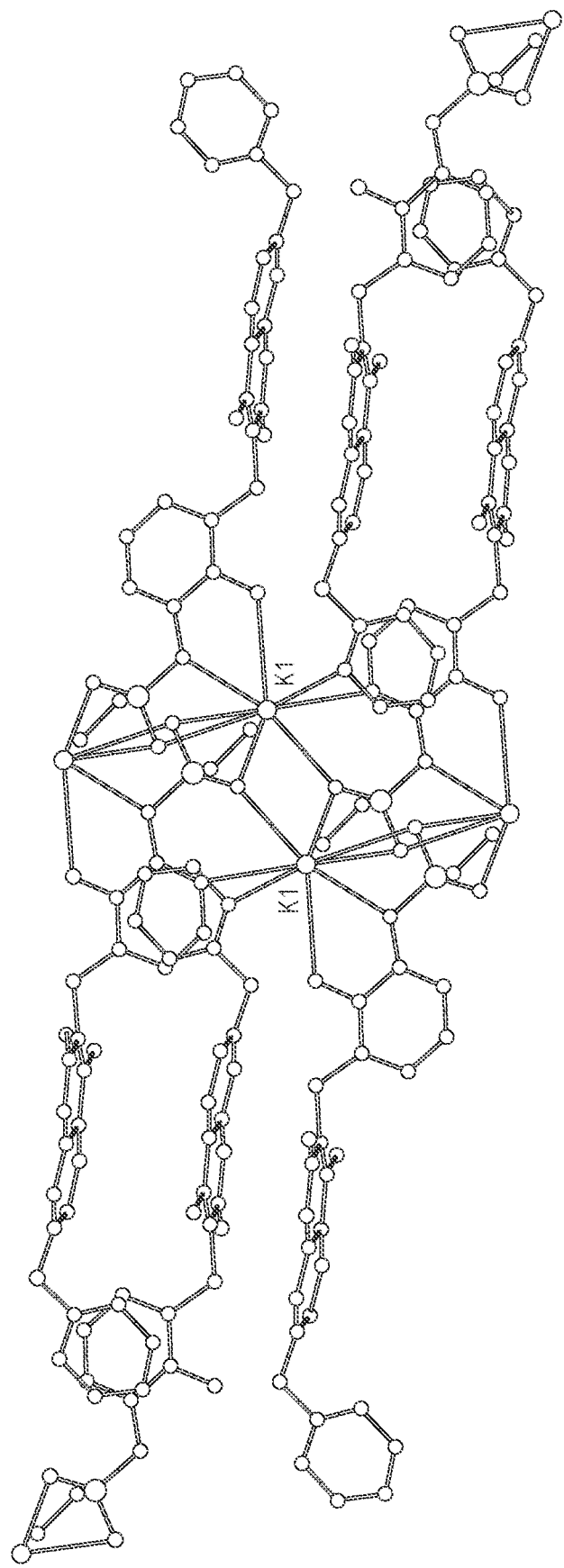
FIG. 28 shows the coordination around potassium cation in the structure of Compound 1 based on single crystal X-ray diffraction of Form 1.
Figure 29:
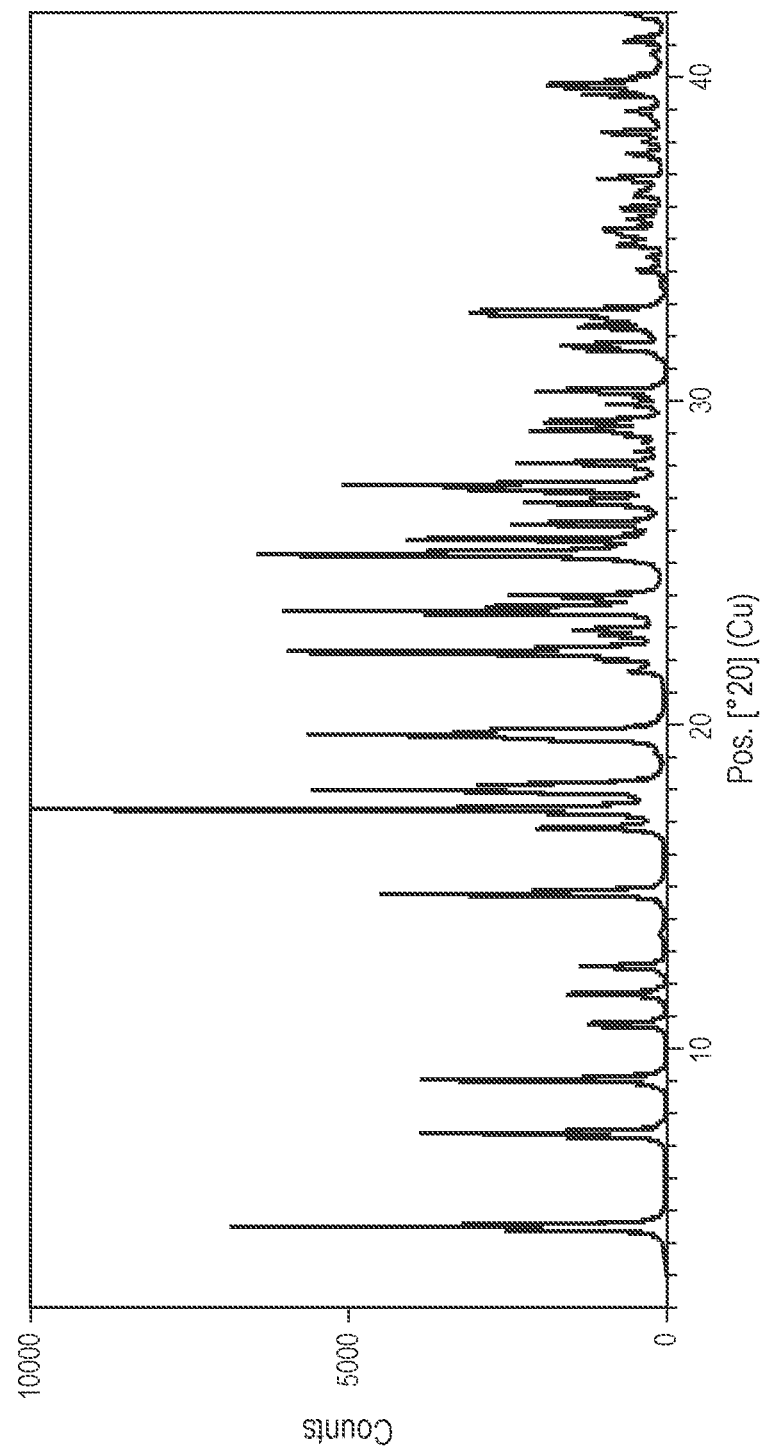
FIG. 29 shows a simulated XRPD pattern of Form 1 at 100K based on the single crystal X-ray diffraction.

The crystal is monoclinic, space group P21/c with the final R1 [I>2σ(I)]=4.37%. The structure was identified as depicted in FIG. 27 and the asymmetric unit found to contain 1 molecule of Compound 1. The structure of Compound 1 is a coordination polymer where the potassium cation is coordinated by four ligands (FIG. 28). Table 11 summarizes sample and crystal data for Form 1. Simulated XRPD pattern at 100K is shown in FIG. 29.

TABLE 11

Sample and crystal data for Form 1.

| | |
|---|---|
| Empirical formula | C21H17FKN5O5S |
| Formula weight | 509.55 |
| Temperature | 100(2) K |
| Wavelength | 1.54184 Å |
| Crystal size | 0.140 × 0.120 × 0.010 mm |
| Crystal habit | colorless plate |
| Crystal system | Monoclinic |
| Space group | P21/c |
| Unit cell dimensions | a = 19.5421(9) Å  α = 90° |
| | b = 15.1329(6) Å  β = 90.579(4)° |
| | c = 6.9265(3) Å  γ = 90° |
| Volume | 2048.27(15) Å$^3$ |
| Z | 4 |
| Density (calculated) | 1.652 Mg/m$^3$ |
| Absorption coefficient | 3.740 mm$^{-1}$ |
| F(000) | 1048 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements or features, some embodiments of the invention or aspects of the invention consist, or consist essentially of, such elements or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any embodiment? of the present invention that falls within the prior art may be explicitly excluded from any one or more of the claims. Because such embodiments are deemed to be known to one of ordinary skill in the art, they may be excluded even if the exclusion is not set forth explicitly herein. Any embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A solid oral dosage form comprising a composition comprising:
(a) crystalline Form 1 of a compound of Formula II:

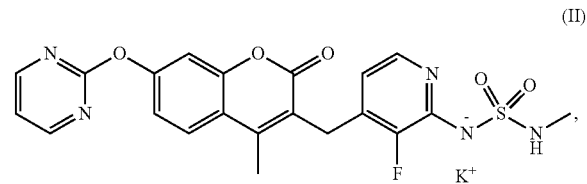 [SMILES: CNS(=O)(=O)Nc1nccc(Cc2c(C)c3ccc(Oc4ncccn4)cc3oc2=O)c1F ; [K+]]

(II)

wherein Form 1 exhibits an X-ray power diffraction (XRPD) pattern comprising characteristic XRPD peaks at the following diffraction angles (2θ (degrees)): 4.5±0.2, 9.0±0.2, and 18.1±0.2; and (b) a pharmaceutically acceptable carrier.

2. The oral dosage form of claim 1, wherein Form 1 exhibits an X-ray power diffraction pattern further comprising at least one characteristic XRPD peak selected from the following diffraction angles (2θ (degrees))=14.7±0.2 and 22.7±0.2.

3. The oral dosage form of claim 1, wherein Form 1 exhibits an X-ray powder diffraction pattern substantially the same as depicted in FIG. 1C.

4. The oral dosage form of claim 1, wherein Form 1 exhibits an endotherm starting from about 255° C. based on differential scanning calorimetry.

5. The oral dosage form of claim 1, wherein Form 1 exhibits a differential scanning calorimetry curve substantially the same as shown in FIG. 2.

6. The oral dosage form of claim 1, wherein Form 1 exhibits a dynamic vapor sorption plot substantially the same as shown in FIG. 3.

7. The oral dosage form of claim 1, wherein Form 1 is an anhydrate.

8. The oral dosage form of claim 1, wherein the oral dosage form is substantially free of other solid forms or patterns of the compound of Formula II.

9. The oral dosage form of claim 1, wherein the oral dosage form is substantially free of an impurity selected from the group consisting of Compound B, Compound C, and Compound D:

(Compound B)
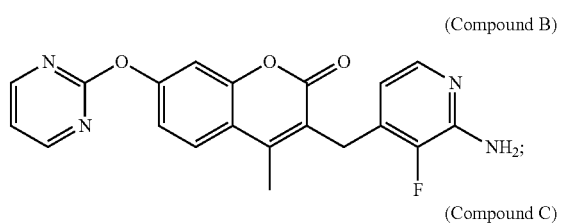

(Compound C)
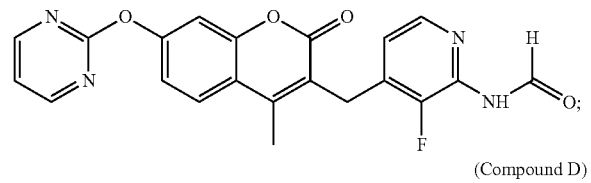

(Compound D)

as determined by HPLC.

10. A method of treating cancer in a subject in need thereof, comprising administering to the subject an effective amount of the oral dosage form of claim 1.

11. The method of claim 10, wherein the cancer is selected from the group consisting of melanoma, lung cancer, ovarian cancer, pancreatic cancer, and colorectal cancer.

12. The method of claim 11, wherein the ovarian cancer is low grade serous ovarian cancer.

13. The method of claim 11, wherein the lung cancer is non-small cell lung cancer.

14. The oral dosage form of claim 1, wherein Form 1 exhibits an X-ray powder diffraction pattern further comprising characteristic XRPD peaks at the following diffraction angles (2θ (degrees))=14.7±0.2 and 22.7±0.2.

15. The oral dosage form of claim 1, wherein Form 1 exhibits an X-ray power diffraction pattern further comprising at least one characteristic XRPD peak selected from the following diffraction angles (2θ (degrees)): 7.3±0.2, 14.7±0.2, 17.1±0.2, 19.4±0.2, and 22.7±0.2.

16. The oral dosage form of claim 1, wherein Form 1 exhibits an X-ray power diffraction pattern further comprising characteristic XRPD peaks at the following diffraction angles (2θ (degrees)): 7.3±0.2, 14.7±0.2, 17.1±0.2, 19.4±0.2, and 22.7±0.2.

17. The oral dosage form of claim 1, wherein Form 1 exhibits an X-ray power diffraction pattern further comprising characteristic XRPD peaks at the following diffraction angles (2θ (degrees)): 7.3±0.2, 10.7±0.2, 13.5±0.2, 14.7±0.2, 16.6±0.2, 17.1±0.2, 17.7±0.2, 19.4±0.2, 21.9±0.2, and 22.7±0.2.

18. The oral dosage form of claim 1, wherein the composition comprises less than 5% by weight of other solid forms or patterns of the compound of Formula II.

19. The oral dosage form of claim 1, wherein the composition comprises less than 1% by weight of other solid forms or patterns of the compound of Formula II.

20. The oral dosage form of claim 1, wherein the composition comprises less than 0.5% by weight of other solid forms or patterns of the compound of Formula II.

21. The oral dosage form of claim 1, wherein the composition comprises less than 0.1% by weight of other solid forms or patterns of the compound of Formula II.

22. The oral dosage form of claim 1, wherein the composition comprises less than 3% by weight of an impurity selected from the group consisting of Compound B, Compound C, and Compound D:

(Compound B)
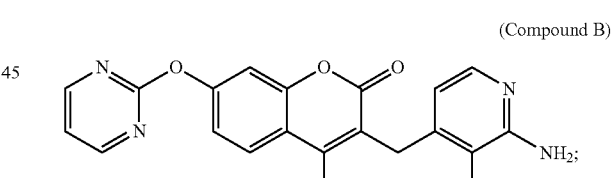

(Compound C)
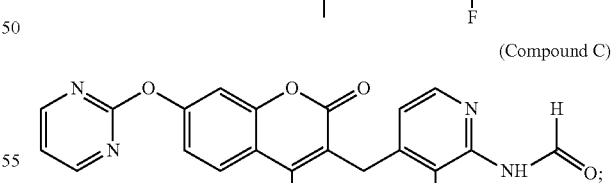

(Compound D)
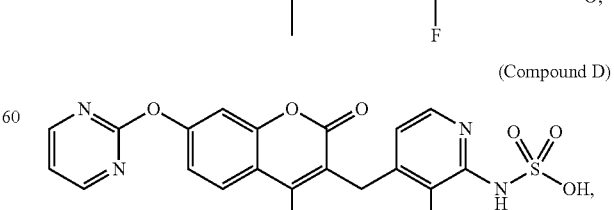

as determined by HPLC.

23. The oral dosage form of claim 1, wherein the composition comprises less than 2% by weight of an impurity selected from the group consisting of Compound B, Compound C, and Compound D:

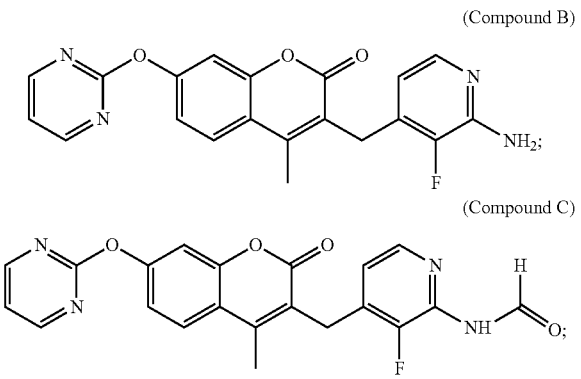

(Compound B)

(Compound C)

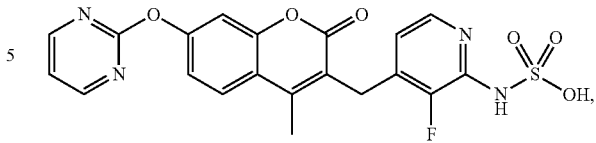

(Compound D)

as determined by HPLC.

24. The oral dosage form of claim 1, wherein the pharmaceutically acceptable carrier is mannitol.

25. The oral dosage form of claim 24, wherein mannitol is a mixture of fine mannitol and granular mannitol.

26. The oral dosage form of claim 1, wherein the composition further comprises a lubricant.

27. The oral dosage form of claim 26, wherein the lubricant is magnesium stearate.

* * * * *